US008969335B2

(12) United States Patent
Hoelzemann et al.

(10) Patent No.: US 8,969,335 B2
(45) Date of Patent: Mar. 3, 2015

(54) BENZONITRILE DERIVATIVES AS KINASE INHIBITORS

(75) Inventors: Guenter Hoelzemann, Seeheim-Jugenheim (DE); Dieter Dorsch, Ober-Ramstadt (DE); Hans-Michael Eggenweiler, Darmstadt (DE)

(73) Assignee: MERCK PATENT GmbH, Darmstadt (DE)

( * ) Notice: Subject to any disclaimer, the term of this patent is extended or adjusted under 35 U.S.C. 154(b) by 0 days.

(21) Appl. No.: 14/342,911

(22) PCT Filed: Aug. 13, 2012

(86) PCT No.: PCT/EP2012/003449
§ 371 (c)(1),
(2), (4) Date: Mar. 5, 2014

(87) PCT Pub. No.: WO2013/034238
PCT Pub. Date: Mar. 14, 2013

(65) Prior Publication Data
US 2014/0228340 A1    Aug. 14, 2014

(30) Foreign Application Priority Data
Sep. 9, 2011    (DE) .......................... 10 2011 112 978

(51) Int. Cl.
| | | |
|---|---|---|
| A61K 31/506 | (2006.01) | |
| A61K 31/4523 | (2006.01) | |
| A61K 31/4427 | (2006.01) | |
| C07D 401/04 | (2006.01) | |
| C07D 401/12 | (2006.01) | |
| C07D 401/14 | (2006.01) | |
| C07D 403/04 | (2006.01) | |
| C07D 403/12 | (2006.01) | |
| C07D 403/14 | (2006.01) | |
| C07D 405/14 | (2006.01) | |
| C07D 413/14 | (2006.01) | |
| C07D 417/14 | (2006.01) | |
| C07D 471/04 | (2006.01) | |
| C07D 491/10 | (2006.01) | |
| A61K 31/4439 | (2006.01) | |
| A61K 31/444 | (2006.01) | |
| A61K 31/4545 | (2006.01) | |
| A61K 31/497 | (2006.01) | |
| A61K 31/501 | (2006.01) | |
| A61K 31/5377 | (2006.01) | |
| A61K 45/06 | (2006.01) | |
| C07D 491/107 | (2006.01) | |

(52) U.S. Cl.
CPC ............ *C07D 401/12* (2013.01); *C07D 401/14* (2013.01); *C07D 405/14* (2013.01); *C07D 413/14* (2013.01); *C07D 417/14* (2013.01); *C07D 471/04* (2013.01); *C07D 491/10* (2013.01); *A61K 31/4439* (2013.01); *A61K 31/444* (2013.01); *A61K 31/4545* (2013.01); *A61K 31/497* (2013.01); *A61K 31/501* (2013.01); *A61K 31/506* (2013.01); *A61K 31/5377* (2013.01); *A61K 45/06* (2013.01); *C07D 491/107* (2013.01)
USPC .................. 514/210.18; 514/275; 514/235.8; 514/210.2; 514/252.02; 514/236.5; 544/122; 544/331; 544/120; 546/268.1

(58) Field of Classification Search
None
See application file for complete search history.

(56) References Cited

U.S. PATENT DOCUMENTS

| | | |
|---|---|---|
| 7,304,071 B2 | 12/2007 | Cochran et al. |
| 8,486,941 B2 | 7/2013 | Burns et al. |
| 8,530,480 B2 | 9/2013 | Kamenecka et al. |
| 2004/0106615 A1 | 6/2004 | Cochran et al. |
| 2007/0021419 A1 | 1/2007 | Wang et al. |
| 2008/0153822 A1 | 6/2008 | Augustin et al. |
| 2010/0197671 A1 | 8/2010 | Burns et al. |
| 2010/0298312 A1 | 11/2010 | Kamenecka et al. |
| 2012/0238540 A1 | 9/2012 | Holcomb et al. |
| 2013/0231336 A1 | 9/2013 | Kamenecka et al. |
| 2013/0267491 A1 | 10/2013 | Perrior et al. |
| 2014/0005180 A1 | 1/2014 | Burns et al. |
| 2014/0011803 A1 | 1/2014 | Burns et al. |
| 2014/0288044 A1* | 9/2014 | Holcomb et al. ........ 514/210.18 |

FOREIGN PATENT DOCUMENTS

| | | |
|---|---|---|
| WO | 2004016597 A2 | 2/2004 |
| WO | 2005012262 A1 | 2/2005 |
| WO | 2008065155 A1 | 6/2008 |
| WO | 2008109943 A1 | 9/2008 |
| WO | 2009032861 A1 | 3/2009 |
| WO | 2010151747 A1 | 12/2010 |
| WO | 2011046970 A1 | 4/2011 |
| WO | 2012010826 A1 | 1/2012 |
| WO | 2012062704 A1 | 5/2012 |

OTHER PUBLICATIONS

International Search Report from PCT/EP2012/003449 dated Oct. 25, 2012.

* cited by examiner

*Primary Examiner* — Michael Barker
(74) *Attorney, Agent, or Firm* — Millen, White, Zelano & Branigan, P.C.

(57) ABSTRACT

Compounds of the formula I, in which $R^1$, $R^2$, X and Y have the meanings indicated in Claim 1, are inhibitors of TBK1 and IKKε and can be employed, inter alia, for the treatment of cancer and inflammatory diseases.

1 Claim, No Drawings

BENZONITRILE DERIVATIVES AS KINASE INHIBITORS

BACKGROUND OF THE INVENTION

The object of the invention was to find novel compounds having valuable properties, in particular those which can be used for the preparation of medicaments.

The present invention relates to benzonitrile compounds which are capable of inhibiting one or more kinases. The compounds are used in the treatment of a multiplicity of disorders, including cancer, septic shock, primary open angle glaucoma (POAG), hyperplasia, rheumatoid arthritis, psoriasis, atherosclerosis, retinopathy, osteoarthritis, endometriosis, chronic inflammation and/or neurodegenerative diseases, such as Alzheimer's disease.

The present invention relates to compounds and to the use of compounds in which the inhibition, regulation and/or modulation of signal transduction by receptor kinases plays a role, furthermore to pharmaceutical compositions which comprise these compounds and to the use of the compounds for the treatment of kinase-induced diseases.

Since protein kinases regulate virtually every cellular process, including metabolism, cell proliferation, cell differentiation and cell survival, they are attractive targets for therapeutic intervention in the case of various conditions. For example, cell-cycle control and angiogenesis, in which protein kinases play a key role, are cell processes associated with numerous conditions, such as, but not limited to, cancer, inflammatory diseases, abnormal angiogenesis and diseases related thereto, atherosclerosis, macular degeneration, diabetes, obesity and pain.

In particular, the present invention relates to compounds and to the use of compounds in which the inhibition, regulation and/or modulation of signal transduction by TBK1 and IKKε plays a role.

One of the principal mechanisms by which cell regulation is effected is through the transduction of extracellular signals across the membrane, which in turn modulate biochemical pathways in the cell. Protein phosphorylation represents one process by which intracellular signals are propagated from molecule to molecule, finally resulting in a cell response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a widespread process in cells and since cell phenotypes are mostly influenced by the activity of these pathways, it is currently thought that a number of conditions and/or diseases are attributable to either aberrant activation or functional mutations in the molecular components of kinase cascades. Consequently, considerable attention has been paid to the characterisation of these proteins and compounds which are able to modulate their activity (review articles see: Weinstein-Oppenheimer et al. Pharma. &. Therap., 2000, 88, 229-279).

IKKε and TBK1 are serine/threonine kinases which are highly homologous to one another and to other IkB kinases. The two kinases play an integral role in the innate immune system. Double-stranded RNA viruses are recognised by the Toll-like receptors 3 and 4, and the RNA helicases RIG-I and MDA-5 and result in activation of the TRIF-TBK1/IKKε-IRF3 signalling cascade, which results in a type I interferon response.

In 2007, Boehm et al. described IKKε as a novel breast cancer oncogene [J. S. Boehm et al., Cell 129, 1065-1079, 2007]. 354 kinases were investigated with respect to their ability to recapitulate the Ras-transforming phenotype together with an activated form of the MAPK kinase Mek. IKKε was identified here as a cooperative oncogene. In addition, the authors were able to show that IKKε is amplified and overexpressed in numerous breast cancer cell lines and tumour samples. The reduction in gene expression by means of RNA interference in breast cancer cells induces apoptosis and impairs the proliferation thereof. Eddy et al. obtained similar findings in 2005, which underlines the importance of IKKε in breast cancer diseases [S. F. Eddy et al., Cancer Res. 2005; 65 (24), 11375-11383].

A protumorigenic effect of TBK1 was reported for the first time in 2006. In a screening of a 251,000 cDNA gene library, Korherr et al. identified precisely three genes, TRIF, TBK1 and IRF3, that are typically involved in the innate immune defence as proangiogenic factors [C. Korherr et al., PNAS, 103, 4240-4245, 2006]. In 2006, Chien et al. [Y. Chien et al., Cell 127, 157-170, 2006] published that TBK1–/– cells can only be transformed to a limited extent using oncogenic Ras, which suggests an involvement of TBK1 in the Ras-mediated transformation. Furthermore, they were able to show that an RNAi-mediated knockdown of TBK1 triggers apoptosis in MCF-7 and Panc-1 cells. Barbie et al. recently published that TBK1 is of essential importance in numerous cancer cell lines with mutated K-Ras, which suggests that TBK1 intervention could be of therapeutic importance in corresponding tumours [D. A. Barbie et al., Nature Letters 1-5, 2009].

Diseases caused by protein kinases are characterised by anomalous activity or hyperactivity of such protein kinases. Anomalous activity relates to either: (1) expression in cells which do not usually express these protein kinases; (2) increased kinase expression, which results in undesired cell proliferation, such as cancer; (3) increased kinase activity, which results in undesired cell proliferation, such as cancer, and/or in hyperactivity of the corresponding protein kinases. Hyperactivity relates either to amplification of the gene which encodes for a certain protein kinase or the generation of an activity level which can be correlated with a cell proliferation disease (i.e. the severity of one or more symptoms of the cell proliferation disease increases with increasing kinase level) the bioavailability of a protein kinase may also be influenced by the presence or absence of a set of binding proteins of this kinase.

IKKε and TBK1 are highly homologous Ser/Thr kinases which play a crucial role in the innate immune response through induction of type 1 interferons and other cytokines. These kinases are stimulated in response to viral/bacterial infection. Immune response to viral and bacterial infections involves the binding of antigens, such as bacterial lipopolysaccharide (LPS), viral double-stranded RNA (dsRNA), to Toll-like receptors, subsequent activation of the TBK1 pathway. Activated TBK1 and IKKε phosphorylate IRF3 and IRF7, which triggers the dimerisation and nuclear translocation of these interferon-regulating transcription factors, ultimately inducing a signalling cascade leading to IFN production.

Recently, IKKε and TBK1 have also been implicated in cancer. It has been shown that IKKε cooperates with activated MEK to transform human cells. In addition, IKKε is frequently amplified/overexpressed in breast cancer cell lines and tumours originating from patients. TBK1 is induced under hypoxic conditions and expressed at significant levels in many solid tumours. Furthermore, TBK1 is necessary to support oncogenic Ras transformation, and TBK1 kinase activity is increased in transformed cells and is necessary for their survival in culture. It has likewise been found that TBK1 and NF-kB signalling are essential in KRAS-mutated tumours. TBK1 has been identified as a synthetic lethal partner of oncogenic KRAS.

Lit.:

Y.-H. Ou et al., Molecular Cell 41, 458-470, 2011;

D. A. Barbie et al., Nature, 1-5, 2009.

WO 2011/046970 A1 describes the use of TBK1 and/or IKKε inhibitors for the treatment of various diseases, such as rheumatoid arthritis (RA), systemic lupus erythematosus (SLE), Sjörgren's syndrome, Aicardi-Goutières syndrome chilblain lupus, retinal vasculopathy and cerebral leukodystrophy (RVCL), systemic sclerosis, myositis, psoriasis, chronic obstructive pulmonary disease (CPD), inflammatory bowel disease (IBD), obesity, insulin resistance, type 2 diabetes (NIDDM), metabolic syndrome, cancer diseases, Accordingly, the compounds according to the invention or a pharmaceutically acceptable salt thereof are administered for the treatment of cancer, including solid carcinomas, such as, for example, carcinomas (for example of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The compounds are furthermore useful in the treatment of immune deficiency induced by HIV-1 (Human Immunodeficiency Virus Type 1).

Cancer-like hyperproliferative diseases are to be regarded as brain cancer, lung cancer, squamous epithelial cancer, bladder cancer, stomach cancer, pancreatic cancer, liver cancer, renal cancer, colorectal cancer, breast cancer, head cancer, neck cancer, oesophageal cancer, gynecological cancer, thyroid cancer, lymphomas, chronic leukaemia and acute leukaemia. In particular, cancer-like cell growth is a disease which represents a target of the present invention. The present invention therefore relates to compounds according to the invention as medicaments and/or medicament active compounds in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an antiproliferative action. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both the prevention of diseases and the treatment of pre-existing conditions. The prevention of proliferation/vitality is achieved by administration of the compounds according to the invention prior to the development of overt disease, for example for preventing tumour growth. Alternatively, the compounds are used for the treatment of chronic diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined.

The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

There are many diseases associated with deregulation of cell proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, perianastomatic prosthetic restenosis, restenosis after angioplasty or stent placement, and the like.

In addition, the compounds according to the invention can be used to achieve additive or synergistic effects in certain existing cancer chemotherapies and radiotherapies and/or to restore the efficacy of certain existing cancer chemotherapies and radiotherapies.

The term "method" refers to manners, means, techniques and procedures for accomplishing a given task, including, but not limited to, those manners, means, techniques and procedures which are either known to the person skilled in the art in the chemical, pharmacological, biological, biochemical and medical area or can easily be developed by him from known manners, means, techniques and procedures b.

The term "administration" as used here refers to a method for bringing a compound of the present invention and a target kinase together in such a way that the compound is able to affect the enzyme activity of the kinase either directly, i.e. by interaction with the kinase itself, or indirectly, i.e. by interaction with another molecule on which the catalytic activity of the kinase is dependent. As used here, administration can be carried out either in vitro, i.e. in a test tube, or in vivo, i.e. in cells or tissues of a living organism.

The term "treatment" here encompasses abrogation, substantial inhibition, slowing or reversal of the progress of a disease or disorder, substantial amelioration of the clinical symptoms of a disease or disorder or substantial prevention of the occurrence of clinical symptoms of a disease or disorder.

The term "prevention" here refers to a method for blocking an organism from acquiring a disorder or disease in the first place.

For any desired compound used in this invention, a therapeutically effective amount, also referred to here as a therapeutically effective dose, can be calculated initially from cell culture assays. For example, a dose can be formulated in animal models to achieve a circulating concentration range that includes the IC50 or the IC100 as determined in cell cultures. This information can be used to determine useful doses for humans more accurately. Initial dosages can also be calculated from in-vivo data. Using these initial guidelines, an average person skilled in the art could determine an effective dosage for humans.

Moreover, the toxicity and therapeutic efficacy of the compounds described here can be determined by standard pharmaceutical procedures on cell cultures or experimental animals, for example by determining the LD50 and the ED50. The dose ratio between toxic and therapeutic effect is the therapeutic index and can be expressed as the ratio between LD50 and ED50. Compounds which exhibit a high therapeutic index are preferred. The data obtained from these cell culture assays and animal studies can be used to formulate a dosage range which is not toxic for human use. The dosage of such compounds is preferably in bloodstream concentration ranges which include the ED50 with little or no toxicity. The dosage may vary within this range depending on the dosage form employed and the route of administration used. The precise formulation, route of administration and dosage can be selected by the individual physician taking into account the patient's condition (see, for example, Fingl et al., 1975, in: The Pharmacological Basis of Therapeutics, Chapter 1, page 1).

Dosage amount and interval may be adjusted individually to provide plasma levels of the active compound which are sufficient to obtain a therapeutic effect. Usual patient dosages for oral administration are in the range from about 50-2000 mg/kg/day, generally from about 100-1000 mg/kg/day, preferably from about 150-700 mg/kg/day and particularly preferably from about 250-500 mg/kg/day.

Therapeutically effective serum levels are preferably achieved by administration of multiple doses per day. In the case of local administration or selective uptake, the effective local concentration of the medicament may not be related to the plasma concentration. The person skilled in the art will be able to optimise therapeutically effective local dosages without undue experimentation.

Preferred diseases or disorders for the prevention, treatment and/or investigation of which the compounds described here may be useful are cell proliferative disorders, in particular cancer, such as, but not limited to, papilloma, blastoglioma, Kaposi's sarcoma, melanoma, lung cancer, ovarian cancer, prostate cancer, squamous cell carcinoma, astrocytoma, head cancer, neck cancer, skin cancer, liver cancer, bladder cancer, breast cancer, lung cancer, uterine cancer, prostate cancer, testicular carcinoma, colorectal cancer, thyroid cancer, pancreatic cancer, stomach cancer, hepatocellular carcinoma, leukaemia, lymphoma, Hodgkin's disease and Burkitt's disease.

PRIOR ART

Other benzonitrile derivatives are described as TBK1 and/or IKKε inhibitors in WO 2011/046970 A1 and in WO 2012/010826 A1.

Further heterocyclic derivatives and their use as antitumour agents have been described in WO 2007/129044.

Further pyridine and pyrazine derivatives have been described in the use for the treatment of cancer in WO 2009/053737 and for the treatment of other diseases in WO 2004/055005.

Further heterocyclic derivatives have been disclosed as IKKε inhibitors in WO 2009/122180.

Pyrrolopyrimidines have been described as IKKε and TBK1 inhibitors in WO 2010/100431.

Pyrimidine derivatives have been described as IKKε and TBK1 inhibitors in WO 2009/030890.

SUMMARY OF THE INVENTION

The invention relates to compounds of the formula I

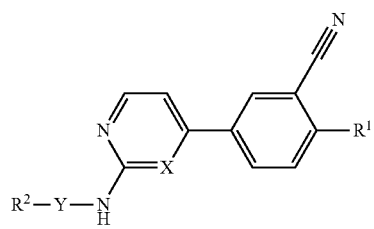

in which
X denotes CH or N,
Y denotes Het²-diyl,
R¹ denotes $O(CH_2)_n Het^1$, $NH(CH_2)_n Het^1$, OA, NHA, $NA_2$, $O(CH_2)_n Cyc$ or $NH(CH_2)_n Cyc$,
R² denotes H, A, Ar¹, $(CH_2)_n Het^3$, CN, $(CH_2)_n Cyc$, $CONH_2$, COOA, $(CH_2)_n OH$, $(CH_2)_n OA$, $(CH_2)_n NH_2$, $(CH_2)_n NHA$ or $(CH_2)_n NA_2$,
Ar¹ denotes phenyl which is unsubstituted or mono-, di- or trisubstituted by Hal, A, OH, OA, COOH, COOA, CN, $CONH_2$, $NHSO_2A$ and/or $SO_2A$,
Het¹ denotes dihydropyrrolyl, pyrrolidinyl, azetidinyl, tetrahydroimidazolyl, dihydropyrazolyl, tetrahydropyrazolyl, dihydropyridyl, tetrahydropyridyl, piperidinyl, morpholinyl, hexahydropyridazinyl, hexahydropyrimidinyl, 1,3-dioxolanyl, tetrahydropyranyl or piperazinyl, each of which is unsubstituted or monosubstituted by OH, COOA, $CONH_2$, COA and/or A,
Het² denotes furyl, thienyl, pyrrolyl, imidazolyl, pyrazolyl, oxazolyl, isoxazolyl, thiazolyl, triazolyl, pyridyl, pyrimidyl, pyridazinyl, pyrazinyl, indolyl, isoindolyl, benzimidazolyl, indazolyl, quinolyl, 1,3-benzodioxolyl, benzothiophenyl, benzofuranyl, imidazopyridyl, 5,6,7,8-tetrahydropyrido[4,3-d]pyrimidin-2-yl or furo[3,2-b]pyridyl, each of which is unsubstituted or monosubstituted by Hal, A, OH, =O, OA, CN, COOA, COOH, $CONH_2$ and/or NHCOA,
Het³ denotes dihydropyrrolyl, pyrrolidinyl, azetidinyl, tetrahydroimidazolyl, tetrahydrofuranyl, dihydropyrazolyl, tetrahydropyrazolyl, dihydropyridyl, tetrahydropyridyl, piperidinyl, morpholinyl, hexahydropyridazinyl, hexahydropyrimidinyl, 1,3-dioxolanyl, dihydropyranyl, tetrahydropyranyl, piperazinyl, furyl, thienyl, pyrrolyl, imidazolyl, pyrazolyl, oxazolyl, isoxazolyl, thiazolyl, triazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or mono- or disubstituted by Hal, A, OH, OA, CN, COOA, COOH, $CONH_2$, CONHA, $CONA_2$, COA, $COCH_2NH_2$, $COCH_2NHA$, $COCH_2NA_2$, $(CH_2)_nCyc$ and/or NHCOA, A denotes unbranched or branched alkyl having 1-10 C atoms, in which one or two non-adjacent CH and/or $CH_2$ groups may be replaced by N, O and/or S atoms and/or, in addition, 1-7H atoms may be replaced by F and/or Cl, Cyc denotes cyclic alkyl having 3, 4, 5, 6 or 7 C atoms which is unsubstituted or monosubstituted by CN, $(CH_2)_nOH$ or A, Hal denotes F, Cl, Br or I, n denotes 0, 1, 2, 3 or 4, and pharmaceutically usable salts, tautomers and stereoisomers thereof, including mixtures thereof in all ratios.

The invention also relates to the optically active forms (stereoisomers), salts, the enantiomers, the racemates, the diastereomers and the hydrates and solvates of these compounds. Solvate of the compounds are taken to mean adductions of inert solvent molecules onto the compounds which form owing to their mutual attractive force. Solvate are, for example, mono- or dihydrates or alcoholates. The invention naturally also relates to the solvates of the salts.

Pharmaceutically usable derivatives are taken to mean, for example, the salts of the compounds according to the invention and also so-called prodrug compounds. Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I and pharmaceutically usable salts, tautomers and stereoisomers thereof, characterised in that a) a compound of the formula II, $$R^2—Y—NH_2 \quad \quad II$$

in which Y and $R^2$ have the meanings indicated in claim 1, is reacted with a compound of the formula III

III in which X and $R^1$ have the meanings indicated in claim 1 and L denotes F, Cl, Br or I, and/or a base or acid of the formula I is converted into one of its salts.

Above and below, the radicals $R^1$, $R^2$, X and Y have the meanings indicated for the formula I, unless expressly indicated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

One or two CH and/or $CH_2$ groups in A may also be replaced by N, O or S atoms. Thus, A also denotes, for example, 2-methoxyethyl.

A particularly preferably denotes unbranched or branched alkyl having 1-8 C atoms, in which, in addition, one or two non-adjacent CH and/or $CH_2$ groups may be replaced by N and/or O atoms and/or 1-7H atoms may be replaced by F.

$Ar^1$ denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-methylaminosulfonylphenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or p-acetylphenyl, o-, m- or p-formylphenyl, o-, m- or p-cyanophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl.

$Ar^1$ particularly preferably denotes phenyl which is unsubstituted or mono-, di- or trisubstituted by A.

$Het^1$ preferably denotes pyrrolidinyl, piperidinyl, morpholinyl or tetrahydropyranyl, each of which is unsubstituted or monosubstituted by COA.

$Het^2$ preferably denotes thienyl, pyrazolyl, oxazolyl, isoxazolyl, pyridyl, pyrazinyl, pyridazinyl, thiazolyl, pyrimidyl, indolyl, 5,6,7,8-tetrahydropyrido[4,3-d]pyrimidin-2-yl or benzofuranyl, each of which is unsubstituted or monosubstituted by =O or OA.

Het³ preferably denotes pyrrolidinyl, azetidinyl, tetrahydrofuranyl, dihydropyranyl, tetrahydropyranyl, dihydropyridyl, tetrahydropyridyl, piperidinyl, piperazinyl, morpholinyl, furyl, thienyl, pyrazolyl, benzofuranyl or pyridyl, each of which is unsubstituted or monosubstituted by A.

Hal preferably denotes F, Cl or Br, but also I, particularly preferably F or Cl.

X preferably denotes CH.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ig, which conform to the formula I and in which the radicals not designated in greater detail have the meaning indicated for the formula I, but in which in Ia R¹ denotes O(CH₂)ₙHet¹ or O(CH₂)ₙCyc;

in Ib Ar¹ denotes phenyl which is unsubstituted or mono-, di- or trisubstituted by A;

in Ic Het¹ denotes pyrrolidinyl, piperidinyl, morpholinyl or tetrahydropyranyl, each of which is unsubstituted or monosubstituted by COA;

in Id Het² denotes thienyl, pyrazolyl, oxazolyl, isoxazolyl, pyridyl, pyrazinyl, pyridazinyl, thiazolyl, pyrimidyl, indolyl, 5,6,7,8-tetrahydropyrido[4,3-d]pyrimidin-2-yl or benzofuranyl, each of which is unsubstituted or monosubstituted by =O or OA;

in Ie Het³ denotes pyrrolidinyl, azetidinyl, tetrahydrofuranyl, dihydropyranyl, tetrahydropyranyl, dihydropyridyl, tetrahydropyridyl, piperidinyl, piperazinyl, morpholinyl, furyl, thienyl, pyrazolyl, benzofuranyl or pyridyl, each of which is unsubstituted or monosubstituted by A;

in If A denotes unbranched or branched alkyl having 1-8 C atoms, in which one or two non-adjacent CH and/or CH₂ groups may be replaced by N and/or O atoms and/or, in addition, 1-7H atoms may be replaced by F;

in Ig X denotes CH or N,
Y denotes Het²-diyl,
R¹ denotes O(CH₂)ₙHet¹ or O(CH₂)ₙCyc,
R² denotes H, A, Ar¹, (CH₂)ₙHet³, CN, (CH₂)ₙCyc, CONH₂, COOA, (CH₂)ₙOH, (CH₂)ₙOA, (CH₂)ₙNH₂, (CH₂)ₙNHA or (CH₂)ₙNA₂,
Ar¹ denotes phenyl which is unsubstituted or mono-, di- or trisubstituted by A,
Het¹ denotes unsubstituted pyrrolidinyl, piperidinyl, morpholinyl or tetrahydropyranyl,
Het² denotes thienyl, pyrazolyl, oxazolyl, isoxazolyl, pyridyl, pyrazinyl, pyridazinyl, thiazolyl, pyrimidyl, indolyl, 5,6,7,8-tetrahydropyrido[4,3-d]pyrimidin-2-yl or benzofuranyl, each of which is unsubstituted or monosubstituted by =O or OA,
Het³ denotes pyrrolidinyl, azetidinyl, tetrahydrofuranyl, dihydropyranyl, tetrahydropyranyl, dihydropyridyl, tetrahydropyridyl, piperidinyl, morpholinyl, furyl, thienyl, pyrazolyl, benzofuranyl or pyridyl, each of which is unsubstituted or monosubstituted by A,
A denotes unbranched or branched alkyl having 1-8 C atoms, in which one or two non-adjacent CH and/or CH₂ groups may be replaced by N and/or O atoms and/or, in addition, 1-7H atoms may be replaced by F,
Cyc denotes cyclic alkyl having 3, 4, 5, 6 or 7 C atoms which is unsubstituted or monosubstituted by CN or A,
n denotes 0, 1, 2, 3 or 4,
and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], GeorgThieme-Verlag, Stuttgart), to be precise under reaction conditions which are known and suitable for the said reactions. Use can also be made here of variants known per se which are not mentioned here in greater detail.

Compounds of the formula I can preferably be obtained by reacting compounds of the formula II with a compound of the formula III.

The compounds of the formula II and of the formula III are generally known. If they are novel, however, they can be prepared by methods known per se.

The reaction is carried out under Buchwald-Hartwig conditions, which are known to the person skilled in the art.

Depending on the conditions used, the reaction time is between a few minutes and 14 days, the reaction temperature is between about −10° and 160°, normally between 20° and 150°, particularly preferably between 80° and about 150°.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to dioxane.

In the compounds of the formula III, L preferably denotes Cl, Br or I, particularly preferably Cl.

The cleavage of an ether is carried out under methods known to the person skilled in the art.

A standard method of ether cleavage, for example of a methyl ether, is the use of boron tribromide.

Hydrogenolytically removable groups, for example the cleavage of a benzyl ether, can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar.

Esters can be hydrolysed, for example, using acetic acid or using NaOH or KOH in water, water/THF or water/dioxane at temperatures between 0 and 100°.

Alkylations on the nitrogen are carried out under standard conditions, as are known to the person skilled in the art.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine(benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine(tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound of the formula I in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

The invention furthermore relates to medicaments comprising at least one compound of the formula I and/or pharmaceutically usable salts, tautomers and stereoisomers thereof, including mixtures thereof in all ratios, and optionally excipients and/or adjuvants.

Pharmaceutical formulations can be administered in the form of dosage units which comprise a predetermined amount of active compound per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and pharmaceutically usable salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and pharmaceutically usable salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-compound solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or as well as pharmaceutically usable salts, tautomers and stereoisomers thereof, including mixtures thereof in all ratios, and at least one further medicament active compound.

The invention also relates to a set (kit) consisting of separate packs of (a) an effective amount of a compound of the formula I and/or pharmaceutically usable salts, tautomers and stereoisomers thereof, including mixtures thereof in all ratios, and (b) an effective amount of a further medicament active compound.

The set comprises suitable containers, such as boxes, individual bottles, bags or ampoules. The set may, for example, comprise separate ampoules, each containing an effective amount of a compound of the formula I and/or pharmaceutically usable salts, tautomers and stereoisomers thereof, including mixtures thereof in all ratios, and an effective amount of a further medicament active compound in dissolved or lyophilised form.

Isotopes

It is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug thereof or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^3$H or $^{14}$C, has been incorporated is suitable for medicament and/or substrate tissue distribution assays. These radioisotopes, i.e. tritium ($^3$H) and carbon-14 ($^{14}$C), are particularly preferred owing to their simple preparation and excellent detectability. Incorporation of heavier isotopes, for example deuterium ($^2$H), into a compound of the formula I has therapeutic advantages owing to the higher metabolic stability of this isotope-labelled compound. Higher metabolic stability translates directly into an increased in-vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant with a readily available isotope-labelled reactant.

In order to manipulate the oxidative metabolism of the compound by way of the primary kinetic isotope effect, deuterium ($^2$H) can also be incorporated into a compound of the formula I. The primary kinetic isotope effect is a change in the rate of a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom in a non-exchangeable position, rate differences of $k_M/k_D=2$-$7$ are typical. If this rate difference is successfully applied to a compound of the formula I that is susceptible to oxidation, the profile of this compound in vivo can thereby be drastically modified and result in improved pharmacokinetic properties.

When discovering and developing therapeutic agents, the person skilled in the art attempts to optimise pharmacokinetic parameters while retaining desirable in-vitro properties. It is reasonable to assume that many compounds with poor pharmacokinetic profiles are susceptible to oxidative metabolism. In-vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of the compounds of the formula I are thereby obtained and can be expressed quantitatively in terms of increases in the in-vivo half-life (T/2), concentration at maximum therapeutic effect ($C_{max}$), area under the dose response curve (AUC), and F; and in terms of reduced clearance, dose and costs of materials.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the undesired metabolite, even if the particular oxidation is not a rate-determining step. Further information on the state of the art with respect to deuterium-hydrogen exchange is given, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al., Biochemistry 33(10), 2927-2937, 1994, and Jarman et al., Carcinogenesis 16(4), 683-688, 1993.

Use

The invention relates to the compounds of the formula I for use for the treatment of cancer, septic shock, primary open angle glaucoma (POAG), hyperplasia, rheumatoid arthritis, psoriasis, atherosclerosis, retinopathy, osteoarthritis, endometriosis, chronic inflammation and/or neurodegenerative diseases, such as Alzheimer's disease.

The invention relates to the use of compounds of the formula I for the preparation of a medicament for the treatment of cancer, septic shock, primary open angle glaucoma (POAG), hyperplasia, rheumatoid arthritis, psoriasis, atherosclerosis, retinopathy, osteoarthritis, endometriosis, chronic inflammation and/or neurodegenerative diseases, such as Alzheimer's disease.

The invention relates to a method for the treatment of a mammal suffering from a disease selected from cancer, septic shock, primary open angle glaucoma (POAG), hyperplasia, rheumatoid arthritis, psoriasis, atherosclerosis, retinopathy, osteoarthritis, endometriosis, chronic inflammation and/or neurodegenerative diseases, such as Alzheimer's disease, where the method comprises the administration of a therapeutically effective amount of a compound of the formula I to a mammal.

The invention furthermore relates to the compounds of the formula I for use for the treatment of cancer, septic shock, primary open angle glaucoma (POAG), hyperplasia, atherosclerosis, retinopathy, osteoarthritis, endometriosis, chronic inflammation, neurodegenerative diseases, rheumatoid arthritis (RA), systemic lupus erythematosus (SLE), Sjörgren's syndrome, Aicardi-Goutières syndrome chilblain lupus, retinal vasculopathy, cerebral leukodystrophy (RVCL), systemic sclerosis, myositis, psoriasis, chronic obstructive pulmonary disease (CPD), inflammatory bowel disease (IBD), obesity, insulin resistance, type 2 diabetes (NIDDM) and/or metabolic syndrome The present compounds are suitable as pharmaceutical active compounds for mammals, in particular for humans, in the treatment and combating of cancer diseases and inflammatory diseases.

The host or patient can belong to any mammalian species, for example a primate species, particularly humans; rodents, including mice, rats and hamsters; rabbits; horses, cows, dogs, cats, etc. Animal models are of interest for experimental investigations, providing a model for the treatment of a human disease.

The susceptibility of a particular cell to treatment with the compounds according to the invention can be determined by in vitro tests. Typically, a culture of the cell is combined with a compound according to the invention at various concentrations for a period of time which is sufficient to make it possible for the active agents, such as anti-IgM, to induce a cell response, such as expression of a surface marker, usually between about one hour and one week. In vitro testing can be carried out using cultivated cells from blood or a biopsy sample. The amount of expressed surface marker is assessed by flow cytometry using specific antibodies which recognise the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-Gonzalez, R. and Glenney, Jr., J. R. 1992, J. Biol. Chem. 267, page 14535).

For the identification of kinase inhibitors, various assay systems are available. In scintillation proximity assay (Sorg et al., J. of Biomolecular Screening, 2002, 7, 11-19) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTRFRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

The present invention encompasses the use of the compounds of the formula I and/or physiologically acceptable salts, tautomers and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma bowel cancer. A further group of preferred forms of cancer are monocytic leukaemia, lung adenocarcinoma, small-cell lung carcinomas, pancreatic cancer, glioblastomas and breast carcinoma.

Likewise encompassed is the use of the compounds of the formula I and/or physiologically acceptable salts, tautomers and solvates thereof for the preparation of a medicament for the treatment and/or control of a tumour-induced disease in a mammal, in which to this method a therapeutically effective amount of a compound according to the invention is administered to a sick mammal in need of such treatment. The therapeutic amount varies according to the particular disease and can be determined by the person skilled in the art without undue effort.

Particular preference is given to the use for the treatment of a disease, where the cancer disease is a solid tumour.

The solid tumour is preferably selected from the group of tumours of the squamous epithelium, the bladder, the stomach, the kidneys, of head and neck, the esophagus, the cervix, the thyroid, the intestine, the liver, the brain, the prostate, the urogenital tract, the lymphatic system, the stomach, the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention furthermore relates to the use of the compounds according to the invention for the treatment of bone pathologies, where the bone pathology originates from the group osteosarcoma, osteoarthritis and rickets.

The compounds of the formula I may also be administered at the same time as other well-known therapeutic agents that are selected for their particular usefulness against the condition that is being treated.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cisretinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[diamineplatinum(II)]bis[diamine(chloro)platinum(II)]tetrachloride, diarisidinyl-spermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]-quinolin-7-one and dimesna.

"Antiproliferative agents" include antisense RNA and DNA oligonucleotides such as G3139, ODN698, RVASK-RAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

The medicaments from Table 1 below are preferably, but not exclusively, combined with the compounds of the formula I.

TABLE 1

| Alkylating agents | Cyclophosphamide | Lomustine |
|---|---|---|
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | |
| | Ormiplatin | BBR-3464 (Hoffmann-La Roche) |
| | Iproplatin | |
| | | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |

TABLE 1-continued

| | | |
|---|---|---|
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxycamptothecin | |
| | Topotecan | TAS-103 (Taiho) |
| | Dexrazoxanet (TopoTarget) | Elsamitrucin (Spectrum) |
| | Pixantrone (Novuspharma) | J-107088 (Merck & Co) |
| | Rebeccamycin analogue (Exelixis) | BNP-1350 (BioNumerik) |
| | | CKD-602 (Chong Kun Dang) |
| | BBR-3576 (Novuspharma) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | |
| | Idarubicin | Bleomycinic acid |
| | Rubidazon | Bleomycin A |
| | Plicamycinp | Bleomycin B |
| | Porfiromycin | Mitomycin C |
| | Cyanomorpholinodoxorubicin | MEN-10755 (Menarini) |
| | Mitoxantron (Novantron) | GPX-100 (Gem Pharmaceuticals) |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | Cemadotin (BASF) | ER-86526 (Eisai) |
| | RPR 109881A (Aventis) | Combretastatin A4 (BMS) |
| | TXD 258 (Aventis) | Isohomohalichondrin-B (PharmaMar) |
| | Epothilone B (Novartis) | |
| | T 900607 (Tularik) | ZD 6126 (AstraZeneca) |
| | T 138067 (Tularik) | PEG-Paclitaxel (Enzon) |
| | Cryptophycin 52 (Eli Lilly) | AZ10992 (Asahi) |
| | Vinflunine (Fabre) | !DN-5109 (Indena) |
| | Auristatin PE (Teikoku Hormone) | AVLB (Prescient NeuroPharma) |
| | BMS 247550 (BMS) | Azaepothilon B (BMS) |
| | BMS 184476 (BMS) | BNP-7787 (BioNumerik) |
| | BMS 188797 (BMS) | CA-4-prodrug (OXiGENE) |
| | Taxoprexin (Protarga) | Dolastatin-10 (NrH) |
| | | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | |
| | BAY-43-9006 (Bayer) | Perillyl alcohol (DOR BioPharma) |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |

TABLE 1-continued

| | | |
|---|---|---|
| Histone acetyl-transferase inhibitors | Tacedinaline (Pfizer)<br>SAHA (Aton Pharma)<br>MS-275 (Schering AG) | Pivaloyloxymethyl butyrate (Titan)<br>Depsipeptide (Fujisawa) |
| Metalloproteinase inhibitors | Neovastat (Aeterna Laboratories)<br>Marimastat (British Biotech) | CMT-3 (CollaGenex)<br>BMS-275291 (Celltech) |
| Ribonucleoside reductase inhibitors | Gallium maltolate (Titan)<br>Triapin (Vion) | Tezacitabine (Aventis)<br>Didox (Molecules for Health) |
| TNF-alpha agonists/antagonists | Virulizin (Lorus Therapeutics)<br>CDC-394 (Celgene) | Revimid (Celgene) |
| Endothelin-A receptor antagonists | Atrasentan (Abbot)<br>ZD-4054 (AstraZeneca) | YM-598 (Yamanouchi) |
| Retinic acid receptor agonists | Fenretinide (Johnson & Johnson)<br>LGD-1550 (Ligand) | Alitretinoin (Ligand) |
| Immunomodulators | Interferon<br>Oncophage (Antigenics)<br>GMK (Progenics)<br>Adenocarcinoma vaccine (Biomira)<br>CTP-37 (AVI BioPharma)<br>JRX-2 (Immuno-Rx)<br>PEP-005 (Peplin Biotech)<br>Synchrovax vaccines (CTL Immuno)<br>Melanoma vaccine (CTL Immuno)<br>p21-RAS vaccine (GemVax) | Dexosome therapy (Anosys)<br>Pentrix (Australian Cancer Technology)<br>JSF-154 (Tragen)<br>Cancer vaccine (Intercell)<br>Norelin (Biostar)<br>BLP-25 (Biomira)<br>MGV (Progenics)<br>!3-Alethin (Dovetail)<br>CLL-Thera (Vasogen) |
| Hormonal and antihormonal agents | Oestrogens<br>Conjugated oestrogens<br>Ethynyloestradiol<br>chlorotrianisene<br>Idenestrol<br>Hydroxyprogesterone caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (EntreMed)<br>Arzoxifen (Eli Lilly) |
| Photodynamic agents | Talaporfin (Light Sciences)<br>Theralux (Theratechnologies)<br>Motexafin-Gadolinium (Pharmacyclics) | Pd-bacteriopheophorbide (Yeda)<br>Lutetium-Texaphyrin (Pharmacyclics)<br>Hypericin |
| Tyrosine kinase inhibitors | Imatinib (Novartis)<br>Leflunomide (Sugen/Pharmacia)<br>ZDI839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmithKline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various agents | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-IOO (gal3 antagonist, GlycoGenesys)<br>G17DT immunogen (gastrin | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF- |

TABLE 1-continued

| | |
|---|---|
| inhibitor, Aphton) | kappaB inhibitor, Encore) |
| Efaproxiral (oxygenator, Allos Therapeutics) | 3CPA (NF-kappaB inhibitor, Active Biotech) |
| PI-88 (heparanase inhibitor, Progen) | Seocalcitol (vitamin D receptor agonist, Leo) |
| Tesmilifen (histamine antagonist, YM BioSciences) | 131-I-TM-601 (DNA antagonist, TransMolecular) |
| Histamine (histamine H2 receptor agonist, Maxim) | Eflornithin (ODC inhibitor, ILEX Oncology) |
| Tiazofurin (IMPDH inhibitor, Ribapharm) | Minodronic acid (osteoclast inhibitor, Yamanouchi) |
| Cilengitide (integrin antagonist, Merck KGaA) | Indisulam (p53 stimulant, Eisai) |
| SR-31747 (IL-1 antagonist, Sanofi-Synthelabo) | Aplidine (PPT inhibitor, PharmaMar) |
| CCI-779 (mTOR kinase inhibitor, Wyeth) | Rituximab (CD20 antibody, Genentech) |
| Exisulind (PDE-V inhibitor, Cell Pathways) | Gemtuzumab (CD33 antibody, Wyeth Ayerst) |
| CP-461 (PDE-V inhibitor, Cell Pathways) | PG2 (haematopoiesis promoter, Pharmagenesis) |
| AG-2037 (GART inhibitor, Pfizer) | Immunol ™ (triclosan mouthwash, Endo) |
| WX-UK1 (plasminogen activator inhibitor, Wilex) | Triacetyluridine (uridine prodrug, Wellstat) |
| PBI-1402 (PMN stimulant, ProMetic LifeSciences) | SN-4071 (sarcoma agent, Signature BioScience) |
| Bortezomib (proteasome inhibitor, Millennium) | TransMID-107 ™ (immunotoxin, KS Biomedix) |
| SRL-172 (T-cell stimulant, SR Pharma) | PCK-3145 (apoptosis promoter, Procyon) |
| TLK-286 (glutathione-S transferase inhibitor, Telik) | Doranidazole (apoptosis promoter, Pola) |
| PT-100 (growth factor agonist, Point Therapeutics) | CHS-828 (cytotoxic agent, Leo) |
| Midostaurin (PKC inhibitor, Novartis) | trans-Retinic acid (differentiator, NIH) |
| Bryostatin-1 (PKC stimulant, GPC Biotech) | MX6 (apoptosis promoter, MAXIA) |
| CDA-II (apoptosis promoter, Everlife) | Apomine (apoptosis promoter, ILEX Oncology) |
| SDX-101 (apoptosis promoter, Salmedix) | Urocidine (apoptosis promoter, Bioniche) |
| Ceflatonin (apoptosis promoter, ChemGenex) | Ro-31-7453 (apoptosis promoter, La Roche) |
| | Brostallicin (apoptosis promoter, Pharmacia) |

A combined treatment of this type can be achieved with the aid of simultaneous, consecutive or separate dispensing of the individual components of the treatment. Combination products of this type employ the compounds according to the invention.

Test for the Inhibition of IKKε

IKKε—Kinase Assay (IKKepsilon)
Summary

The kinase assay is performed as 384-well flashplate assay (for example for Topcount measurement).

1 nM IKKε, 800 nM biotinylated IκBα(19-42) peptide (Biotin-C6-C6-GLKKERLLDDRHDSGLDSMKDEE) and 10 μM ATP (spiked with 0.3 μCi of $^{33}$P-ATP/well) are incubated at 30° C. for 2 hours in a total volume of 50 μl (10 mM MOPS, 10 mM Mg acetate, 0.1 mM EGTA, 1 mM dithiothreitol, 0.02% of Brij35, 0.1% of BSA, 0.1% of BioStab, pH 7.5) with or without test compound. The reaction is stopped using 25 μl of 200 mM EDTA. After 30 min at room temperature, the liquid is removed, and each well is washed three times with 100 μl of 0.9% sodium chloride solution. Non-specific reaction is determined in the presence of 3 μM MSC2119074 (BX-795). The radioactivity is measured using a Topcount (PerkinElmer). The results (for example IC$_{50}$ values) are calculated using program tools provided by the IT Department (for example AssayExplorer, Symyx).

Test for the Inhibition of TBK1

Enzyme Test
Summary

The kinase assay is performed as 384-well flashplate assay (for example for Topcount measurement).

0.6 nM TANK binding kinase (TBK1), 800 nM biotinylated MELK-derived peptide (Biotin-Ah-Ah-AKP-KGNKDYHLQTCCGSLAYRRR) and 10 μM ATP (spiked with 0.25 μCi of $^{33}$P-ATP/well) are incubated at 30° C. for 120 min in a total volume of 50 μl (10 mM MOPS, 10 mM Mg acetate, 0.1 mM EGTA, 1 mM DTT, 0.02% of Brij35, 0.1% of BSA, pH 7.5) with or without test compound. The reaction is stopped with 25 μl of 200 mM EDTA. After 30 min at room temperature, the liquid is removed, and each well is washed three times with 100 μl of 0.9% sodium chloride solution.

Non-specific reaction is measured in the presence of 100 nM staurosporine. The radioactivity is measured in a Topcount (PerkinElmer). The results (for example $IC_{50}$ values) are calculated using program tools provided by the IT Department (for example AssayExplorer, Symyx).

Cell Test

Dose Response Inhibition of Phospho-IRF3 @ Ser 386 Cell/MDAMB468/INH/PHOS/IMAG/pIRF3

1. Scope

Although TBK1 and IKKε are mainly known as key substances in the innate immune response, recent findings have indicated a role for TBK1 and IKKε in Ras-induced oncogenic transformation. TBK1 was identified as RalB effector in the Ras-like (Rap-guanine nucleotide exchange factor (GEF) pathway that is required for Ras-induced transformation. TBK1 directly activates IRF3 which, on phosphorylation, homodimerises and translocates to the nucleus, where it activates processes associated with inflammation, immune regulation, cell survival and proliferation.

This assay has been developed in order to assess the efficacy/potency of TBK1/IKKε inhibitor compounds based on the immunocytochemical detection of nucleus-localised phospho-IRF3, a target directly downstream of TBK1. Treatment with polyinosine-polycytidylic acid (poly(I:C), a synthetic analogue of double-stranded RNA (dsRNA), a molecular pattern associated with viral infection and recognised by Toll-like receptor 3 (TLR3) is used to induce TBK1/IKKε activity and IRF3 phosphorylation at Ser386.

2. Assay Overview

Day 1: MDA-MB-468 cells are detached using HyQ-Tase, counted and sown into a 384-well plate with TC surface and clear bottom in a density of 10,000 cells per well in a total volume of 35 μl of complete medium. Alternatively, the cells are sown directly from frozen glass vials.

Day 2: The cells are pre-treated with inhibitor compounds for 1 h prior to poly(I:C) stimulation. After incubation for 2 h with poly(I:C), the cells are fixed in (para)formaldehyde (PFA) and permeabilised using methanol (MeOH). The cells are then blocked and incubated with an anti-pIRF3 antibody at 4° C. overnight.

Day 3: The primary antibody is washed off, an AlexaFluor488-conjugated secondary antibody is added, the cells are contrast-stained with propidium iodide, followed by image acquisition on an IMX ultra-high content reader.

3. Reagents, Materials

Cells:
  ATCC HTB 132, Burger Lab (MP-CB 2010-327 or MDA-MB-468/10)
Plating Medium=Culture Medium:
  RPMI 1640, Invitrogen #31870
  10% of FCS, Invitrogen #10270-106
    2 mM Glutamax, Invitrogen #35050-038
    1 mM sodium pyruvate, Invitrogen #11360
    1% of Pen/Strep
  37° C., 5% of $CO_2$
Plates:
  384-well bottom cell culture plates with black/clear bottom, Falcon #35 3962 or Greiner #781090
Subcultivation:
  HyQ-Tase, Thermo Scientific (HyClone) # SV30030.01
Other Reagents:
  Poly(I:C) (LMW), Invitrogen # tlrl-picw (prepare 20 mg/ml stock solution in sterile PBS, denature 30 min 55° C. in a water bath, slowly cool to RT, store at −20° C. in aliquots)
Reference inhibitor: MSC2119074A-4=BX-795 (IC50: 200-800 nM)
  Inhibitory control: 10 μM MSC2119074A-4=BX-795
  Neutral control: 0.5% of DMSO
  a 10-point dose-response curve with MSC2119074A-4=BX-795 is included in each experiment
Hepes, Merck #1.10110
PBS 1×DPBS, Invitrogen #14190
Formaldehyde (methanol-free, 16%, ultrapure EM grade), Polysciences #18814 (storage RT), final conc.: 4%
Methanol, Merck #1.06009.1011 (−20° C. pre-cooled)
Goat serum, PAA # B15-035 (storage 4° C., long term −20° C.), final conc.: 10%
BSA (IgG- and protease-free, 30%), US-Biological # A1317 (storage 4° C., long term −20° C.), final conc.: 2%
Tween 20 detergent, Calbiochem #655204 (storage RT), (prepare 10% stock solution in water; final conc.: 0.1%)
Anti-pIRF-3 rabbit mAb, Epitomics #2526-B (storage −20° C.), final conc.: 1:2000 in PBS/2% of BSA
Alexa Fluor goat-anti-rabbit-488, Invitrogen # A11034 or # A11008 (storage 4° C., dark), final conc.: 1:2000 in PBS/2% of BSA/0.1% of Tween
Propidium iodide (PI), Fluka #81845, 1 mg/ml in $H_2O$ (storage 4° C., dark), final conc.: 0.2 μg/ml 4. Sequence Sow 10,000 cells/well/35 μl of complete RPMI + 10% FCS into 384-well bottom cell culture plates with black/clear bottom

↓

Incubate for 2 h at room temperature on the bench, followed by further incubation for 22 h at 37° C., 5 % of $CO_2$ and 90% RH

↓

Treatment of the compound: add 5 μl of prediluted compounds, standard or control reagents
(8-fold conc.)
Cmpd. dilution of DMSO stock solutions in 20 mM Hepes pH 7.2;
final DMSO conc.: 0.5%
Serial dilution of the cmpds. from 10 mM stock solution (Remp) 10 steps, 3.16-fold in DMSO
30 μM 9.49 μM 3 μM 0.95 μM 0.3 μM 0.095 μM 0.03 μM 0.0095 μM 0.003 μM 0.00095 μM
Incubate for 60 minutes at 37° C., 5% of $CO_2$ and 90% rH

↓

Stimulation treatment: add 10 μl of poly(I:C) to all wells except for unstimulated controls so that a final concentration of 100 μg/ml is achieved
(stock solution 20 mg/ml → 1:40 in PBS) (5-fold conc.)
Incubate for 120 minutes at 37° C., 5 % of $CO_2$ and 90% RH

↓

Completely remove supernatant by suction

↓

Fix cells: add 100 μl of 4% paraformaldehyde in PBS
Incubate for 15 minutes at RT

↓

-continued

Wash 3x with 80 µl of PBS (Tecan powerwasher),
completely aspirate supernatant
Put plate on ice

Permeabilise cells: quickly add 100 µl of MeOH at -20° C.
(pre-cool reservoir)
Incubate for 10 minutes at RT or 4° C.

Wash once with 80 µl of PBS (Tecan powerwasher),
completely remove supernatant by
suction

Block non-specific binding: add 30 µl of
10% goat serum in PBS/2% of BSA
Shake on Multidrop Combi (17 seconds)
Incubate for 60 minutes at 37° C.

Completely remove supernatant by suction

Primary staining: add 25 µl of primary
antibody diluted 1:2000 in PBS/2% BSA
Shake on Multidrop Combi (17 seconds)
Incubate overnight at 4° C.

Wash 3x with 80 µl of PBS (Tecan powerwash), completely remove
supernatant by suction

Secondary staining and nuclear staining: add 25 µl of secondary
antibody (1:2000) and
0.2 µg/ml of propidium iodide in PBS/2% BSA/0.1% Tween
Shake on Multidrop Combi (17 seconds)
Incubate for 75 minutes at 37° C.

Wash 3x with 80 µl of PBS (Tecan powerwash), completely remove
supernatant by suction

Dispense 80 µl of PBS into all wells

Seal plates with transparent adhesive seal

Image acquisition on IMX Ultra (Metaexpress 3.1. scan settings
TBK_10x_pin8)

-continued

Image analysis (Metaexpress 3.1. <cell scoring>, TBK1 cell scoring)

↓

Data analysis and reporting using Assay Explorer

HPLC/HPLC-MS Conditions

The retention time $R_t$ [min] is determined by HPLC:

Column: Chromolith SpeedROD RP-18e, 50×4.6 mm$^2$

Gradient: A:B=96:4 to 0:100

Flow rate: 2.4 ml/min

Eluent A: water+0.05% of formic acid,

Eluent B: acetonitrile+0.04% of formic acid

Wavelength: 220 nm

MS: positive mode

EXAMPLES

Synthesis Scheme 1

General synthetic route for compounds of the formula I in which X=CH.

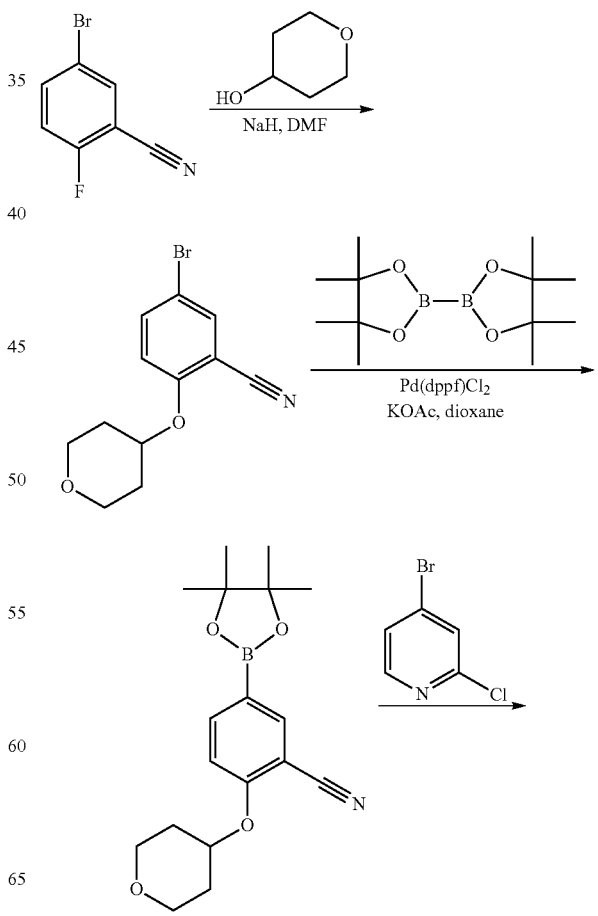

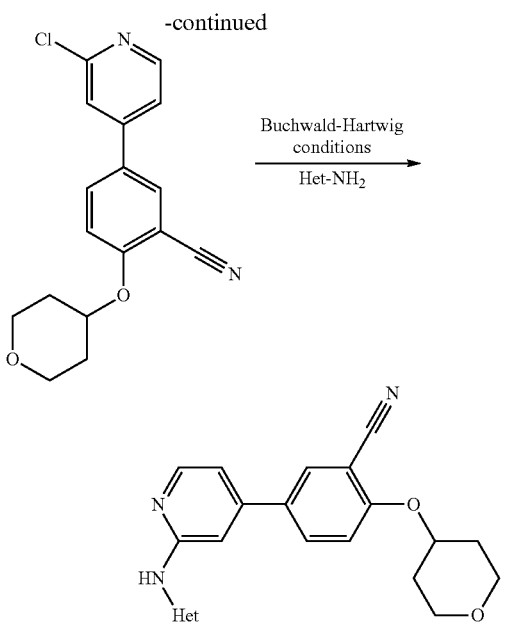

2-(Tetrahydropyran-4-yloxy)-5-(4,4,5,5-tetramethyl-1,3,2-dioxaborolan-2-yl)benzonitrile is prepared as described in WO 2011/046970 A1.

Synthesis of 5-(2-chloropyridin-4-yl)-2-(tetrahydropyran-4-yloxy)benzonitrile 2-(Tetrahydropyran-4-yloxy)-5-(4,4,5,5-tetramethyl-1,3,2-dioxaborolan-2-yl)benzonitrile (3.645 mmol; 1.20 g) and 4-bromo-2-chloropyridine (3.645 mmol; 779 mg) are dissolved in 10 ml of dioxane and 4 ml of water in a 100 ml three-necked flask under $N_2$. 1.008 g of potassium carbonate and 211 mg of tetrakis(triphenylphosphine)palladium(0) are added. The yellow-brown solution is stirred at 90° C. for 2.5 h.

For work-up, the reaction mixture is cooled to room temperature and diluted with water and ethyl acetate and extracted. The combined organic phases are washed with saturated NaCl solution, dried, filtered and evaporated, giving 1.965 g of crude product. For purification, the crude mixture is chromatographed on silica gel with petroleum ether/ethyl acetate, giving 968 mg of the desired product;

HPLC-MS Rt. [min] 2.225; HPLC-MS [M+H] 315;
$^1$H NMR (500 MHz, DMSO-$d_6$) δ [ppm]
General Procedure for the Buchwald-Hartwig Reaction:
5-(2-Chloropyridin-4-yl)-2-(tetrahydropyran-4-yloxy)benzonitrile (100 mg; 0.318 mmol), 1.1 equivalents of the heterocyclic amino component, tris(dibenzylideneacetone)dipalladium(0), 99% (5.8 mg; 0.006 mmol), 9,9-dimethyl-4,5-bis(diphenylphosphino)xanthene, 99% (36.8 mg; 0.064 mmol), caesium carbonate (207 mg; 0.635 mmol), and 2-dicyclohexylphosphino-2',4',6'-triisopropyl-1,1'-biphenyl (3.8 mg; 0.008 mmol) are dissolved in 10 ml of dioxane in a 100 ml three-necked flask under $N_2$. The reaction mixture is then warmed at 140° C. for 4 h and stirred at room temperature overnight.

For work-up, the solvent is removed. The residue is diluted with water and extracted with dichloromethane. The combined organic phases are washed with water, dried, filtered and evaporated. The residue is, if necessary, purified by chromatography.

Preparation of Compounds of the Formula I in Accordance with the General Procedure for the Buchwald-Hartwig Reaction 2-(Tetrahydropyran-4-yloxy)-5-{2-[1-(3-trifluoromethylphenyl)-1H-pyrazol-4-yl-amino]pyridin-4-yl}benzonitrile ("A1")

With 1-[3-(trifluoromethyl)phenyl]-1H-pyrazol-4-amine, the desired product is obtained in a yield of 44%; HPLC-MS Rt. [min] 2.345; HPLC-MS [M+H] 506;
$^1$H NMR (500 MHz, DMSO-$d_6$) δ [ppm] 9.47 (s, 1H), 9.02 (s, 1H), 8.35 (d, J=2.4, 1 H), 8.23 (m, 2H), 8.14 (dd, J=9.0, 2.4, 1H), 8.08 (d, J=6.6, 1H), 8.02 (s, 1H), 7.81 (t, J=8.3, 1H), 7.72 (d, J=7.7, 1H), 7.56 (d, J=9.1, 1H), 7.5-7.43 (m, 2H), 4.97 (tt, J=7.8, 3.7, 1H), 3.93-3.85 (m, 2H), 3.58 (m, 2H), 2.11-2.01 (m, 2H), 1.72 (m, 2H).

5-{2-[1-(1-Methylpiperidin-4-yl)-1H-pyrazol-4-yl-amino]pyridin-4-yl}-2-(tetrahydropyran-4-yloxy)benzonitrile ("A2")

With 1-(1-methylpiperidin-4-yl)-1H-pyrazol-4-ylamine hydrochloride, the desired product is obtained in a yield of 6.7%; HPLC-MS Rt. [min] 1.235; HPLC-MS [M+H] 459;
$^1$H NMR (500 MHz, DMSO-$d_6$) δ [ppm] 9.49 (s, 1H), 8.27 (d, J=2.4, 1H), 8.12-8.06 (m, 2H), 8.01 (d, J=6.4, 1H), 7.73 (d, J=4.0, 1H), 7.52 (d, J=9.2, 1H), 7.41-7.37 (m, 2H), 4.96 (m, 1H), 4.61-4.50 (m, 1H), 3.96-3.87 (m, 2H), 3.69-3.52 (m, 5H), 3.33-3.16 (m, 2H), 2.90 (s, 3H), 2.39-2.18 (m, 4H), 2.08 (m, 2H), 1.76 (m, 2H).

5-[2-([3,3']Bipyridinyl-6-ylamino)pyridin-4-yl]-2-(tetrahydropyran-4-yloxy)benzonitrile ("A3")

With [3,3']bipyridinyl-6-ylamine, the desired product is obtained in quantitative yield; HPLC-MS Rt. [min] 1.492; HPLC-MS [M+H] 450;
$^1$H NMR (500 MHz, DMSO-$d_6$) δ [ppm] 11.36 (s, 1H), 9.06 (d, J=1.9, 1H), 8.77 (d, J=2.4, 1H), 8.70 (dd, J=5.0, 1.4, 1H), 8.41 (d, J=6.0, 1H), 8.38-8.30 (m, 2H), 8.25 (d, J=2.4, 1H), 8.10 (dd, J=8.9, 2.4, 1H), 7.79 (d, J=0.8, 1H), 7.71 (dd, J=8.0, 5.0, 1H), 7.64 (d, J=8.8, 1H), 7.61-7.52 (m, 2H), 4.96 (m, 1H), 3.88 (m, 2H), 3.6 (m, 2H), 2.11-1.98 (m, 2H), 1.77-1.63 (m, 2H).

5-[2-(5-Methylisoxazol-3-ylamino)pyridin-4-yl]-2-(tetrahydropyran-4-yloxy)benzonitrile ("A4")

With 5-methylisoxazol-3-ylamine, the desired product is obtained in 30% yield; HPLC-MS Rt. [min] 1.934; HPLC-MS [M+H] 377;
$^1$H NMR (500 MHz, DMSO-$d_6$) δ [ppm] 9.81 (s, 1H), 8.26 (d, J=5.3, 1H), 8.08 (d, J=2.4, 1H), 7.96 (dd, J=8.9, 2.4, 1H), 7.64 (m, 1H), 7.51 (d, J=9.1, 1H), 7.22 (dd, J=5.3, 1.6, 1H), 6.38 (d, J=0.6, 1H), 4.90 (m, 1H), 3.93-3.81 (m, 2H), 3.55 (m, 2H), 2.03 (m, 2H), 1.68 (m, 2H).

5-[2-(1-Methyl-1H-pyrazol-3-ylamino)pyridin-4-yl]-2-(tetrahydropyran-4-yloxy)benzonitrile ("A5")

With 1-methyl-1H-pyrazol-3-amine, the desired product is obtained in quantitative yield; HPLC-MS Rt. [min] 1.558; HPLC-MS [M+H] 376;
$^1$H NMR (500 MHz, DMSO-$d_6$) δ [ppm] 11.08 (br, 1H), 8.28-8.22 (m, 2H), 8.07 (dd, J=9.0, 2.4, 1H), 7.76 (d, J=2.2, 1H), 7.57 (d, J=9.1, 1H), 7.50 (d, J=1.3, 1H), 7.44-7.36 (m, 1H), 6.20 (d, J=2.3, 1H), 5.00-4.88 (m, 1H), 3.94-3.81 (m, 5H), 3.56 (m, 2H), 2.10-1.97 (m, 2H), 1.77-1.63 (m, 2H).

5-[2-(2-Furan-2-ylmethyl-2H-pyrazol-3-ylamino) pyridin-4-yl]-2-(tetrahydropyran-4-yloxy)benzonitrile ("A6")

With 2-furan-2-ylmethyl-2H-pyrazol-3-ylamine, the desired product is obtained in 55% yield; HPLC-MS Rt. [min] 1.908; HPLC-MS [M+H] 442;
$^1$H NMR (500 MHz, DMSO-$d_6$) δ [ppm] 8.87 (s, 1H), 8.17 (d, J=5.3, 1H), 8.06 (d, J=2.4, 1H), 7.93 (dd, J=8.9, 2.4, 1H), 7.52 (dd, J=1.8, 0.8, 1H), 7.48 (d, J=9.1, 1 H), 7.39 (d, J=6.9, 1H), 7.11 (dd, J=5.4, 1.6, 1H), 6.97 (s, 1H), 5.28 (s, 2H), 4.95-4.83 (m, 1H), 3.94-3.83 (m, 2H), 3.59-3.51 (m, 2H), 2.08-1.95 (m, 2H), 1.72-1.60 (m, 2H).

5-[2-(5-Morpholin-4-ylpyridin-2-ylamino)pyridin-4-yl]-2-(tetrahydropyran-4-yloxy)benzonitrile ("A7")

With 5-morpholin-4-ylpyridin-2-ylamine, the desired product is obtained in 23% yield; HPLC-MS Rt. [min] 1.682; HPLC-MS [M+H] 458;
$^1$H NMR (500 MHz, DMSO-$d_6$) δ [ppm] 11.33 (s, 1H), 8.34 (d, J=6.3, 1H), 8.24 (t, J=7.8, 1H), 8.08 (dd, J=9.0, 2.4, 1H), 7.95 (d, J=2.9, 1H), 7.81 (d, J=7.2, 1H), 7.58 (d, J=9.1, 1H), 7.55-7.46 (m, 2H), 7.33 (d, J=9.2, 1H), 5.01-4.88 (m, 1H), 3.93-3.83 (m, 2H), 3.81-3.71 (m, 4H), 3.61-3.51 (m, 4H), 3.20-3.11 (m, 2H), 2.10-1.99 (m, 2H), 1.74-1.63 (m, 2H).

5-[2-(1-Phenyl-1H-pyrazol-4-ylamino)pyridin-4-yl]-2-(tetrahydropyran-4-yloxy)benzonitrile ("A8")

With 1-phenyl-1H-pyrazol-4-amine, the desired product is obtained in 46% yield; HPLC-MS Rt. [min] 1.977; HPLC-MS [M+H] 438;
$^1$H NMR (500 MHz, DMSO-$d_6$) δ [ppm] 9.45 (s, 1H), 8.70 (s, 1H), 8.17 (dd, J=5.5, 4.3, 2H), 8.01 (dd, J=8.9, 2.2, 1H), 7.85 (s, 1H), 7.82 (d, J=7.8, 2H), 7.54-7.47 (m, 3H), 7.30 (t, J=7.4, 1H), 7.17-7.05 (m, 2H), 4.99-4.86 (m, 1H), 3.93-3.80 (m, 2H), 3.60-3.49 (m, 2H), 2.11-1.97 (m, 2H), 1.75-1.61 (m, 2H).

5-{2-[5-(1H-Pyrazol-4-yl)pyridin-2-ylamino]pyridin-4-yl}-2-(tetrahydropyran-4-yloxy)benzonitrile ("A9")

With tert-butyl 4-(6-aminopyridin-3-yl)pyrazole-1-carboxylate, the desired product is obtained in 16% yield; HPLC-MS Rt. [min] 1.648; HPLC-MS [M+H] 439.

5-[2-(5-tert-Butyl-1H-pyrazol-3-ylamino)pyridin-4-yl]-2-(tetrahydropyran-4-yloxy)benzonitrile ("A10")

With 5-tert-butyl-1H-pyrazol-3-ylamine, the desired product is obtained in 8% yield; HPLC-MS Rt. [min] 1.778; HPLC-MS [M+H] 418;
$^1$H NMR (500 MHz, DMSO-$d_6$) δ [ppm] 12.39 (br, 1H), 10.73 (br, 1H), 8.27 (d, J=6.3, 1H), 8.22 (s, 1H), 8.05 (dd, J=8.9, 2.3, 1H), 7.56 (d, J=9.0, 2H), 7.34 (s, 1H), 5.96 (s, 1H), 5.00-4.88 (m, 1H), 3.95-3.80 (m, 2H), 3.61-3.53 (m, 2H), 2.10-1.97 (m, 2H), 1.77-1.62 (m, 2H), 1.31 (s, 9H).

6-{4-[3-Cyano-4-(tetrahydropyran-4-yloxy)phenyl] pyridin-2-ylamino}nicotinonitrile ("A11")

With 6-aminonicotinonitrile, the desired product is obtained in 94% yield; HPLC-MS Rt. [min] 1.738; HPLC-MS [M+H] 398;
$^1$H NMR (500 MHz, DMSO-$d_6$) δ [ppm] 10.37 (s, 1H), 8.67 (dd, J=2.3, 0.7, 1H), 8.36 (d, J=5.3, 1H), 8.12 (d, J=2.4, 1H), 8.07 (dd, J=8.9, 2.3, 1H), 7.99 (dd, J=5.9, 3.0, 1H), 7.97-7.90 (m, 2H), 7.52 (d, J=9.1, 1H), 7.36 (dd, J=5.3, 1.6, 1H), 4.99-4.83 (m, 1H), 3.96-3.82 (m, 2H), 3.63-3.46 (m, 2H), 2.10-1.96 (m, 2H), 1.78-1.57 (m, 2H).

5-[2-(5-Cyclopropyl-2H-pyrazol-3-ylamino)pyridin-4-yl]-2-(tetrahydropyran-4-yloxy)benzonitrile ("A12")

With 5-amino-3-cyclopropyl-1H-pyrazole, the desired product is obtained in 5% yield; HPLC-MS Rt. [min] 1.674; HPLC-MS [M+H] 402;
$^1$H NMR (500 MHz, DMSO-$d_6$) δ [ppm] 10.79 (br, 1H), 8.26 (d, J=6.3, 1H), 8.21 (d, J=2.0, 1H), 8.04 (dd, J=8.9, 2.4, 1H), 7.56 (d, J=9.1, 1H), 7.50 (s, 1H), 7.37 (d, J=5.1, 1H), 5.87 (s, 1H), 4.94 (m, 1H), 3.87 (m, 2H), 3.55 (m, 2H), 2.13-1.87 (m, 3H), 1.69 (m, 2H), 1.07-0.94 (m, 2H), 0.83-0.67 (m, 2H).

2-(Tetrahydropyran-4-yloxy)-5-[2-(5-trifluoromethylpyridin-2-ylamino)pyridin-4-yl]-benzonitrile ("A13")

With 5-trifluoromethylpyridin-2-ylamine, the desired product is obtained in 34% yield; HPLC-MS Rt. [min] 1.917; HPLC-MS [M+H] 441;
$^1$H NMR (500 MHz, DMSO-$d_6$) δ [ppm] 10.25 (s, 1H), 8.60 (s, 1H), 8.34 (d, J=5.3, 1H), 8.13 (d, J=2.4, 1H), 8.04-7.95 (m, 4H), 7.52 (d, J=9.1, 1H), 7.32 (dd, J=15.1, 7.5, 1H), 4.99-4.84 (m, 1H), 3.92-3.80 (m, 2H), 3.61-3.50 (m, 2H), 2.10-1.98 (m, 2H), 1.75-1.61 (m, 2H).

5-[2-(Pyrimidin-2-ylamino)pyridin-4-yl]-2-(tetrahydropyran-4-yloxy)benzonitrile ("A14")

With pyrimidin-2-ylamine, the desired product is obtained in 95% yield; HPLC-MS Rt. [min] 1.508; HPLC-MS [M+H] 374;
$^1$H NMR (500 MHz, DMSO-$d_6$) δ [ppm] 9.89 (s, 1H), 8.58 (d, J=4.8, 2H), 8.51 (d, J=0.8, 1H), 8.34 (d, J=5.2, 1H), 8.13 (d, J=2.4, 1H), 8.01 (dd, J=8.9, 2.4, 1H), 7.51 (d, J=9.0, 1H), 7.33 (dd, J=5.2, 1.6, 1H), 6.97 (t, J=4.8, 1H), 4.97-4.85 (m, 1H), 3.91-3.82 (m, 2H), 3.61-3.49 (m, 2H), 2.09-1.97 (m, 2H), 1.76-1.63 (m, 2H).

5-[2-(5-Hydroxymethylpyridin-2-ylamino)pyridin-4-yl]-2-(tetrahydropyran-4-yloxy)benzonitrile ("A15")

With (6-aminopyridin-3-yl)methanol, the desired product is obtained in 31% yield; HPLC-MS Rt. [min] 1.536; HPLC-MS [M+H] 403;
$^1$H NMR (500 MHz, DMSO-$d_6$) δ [ppm] 11.41 (br, 1H), 8.42 (d, J=6.0, 1H), 8.31 (d, J=1.2, 1H), 8.25 (d, J=2.3, 1H), 8.08 (dd, J=8.9, 2.4, 1H), 8.00 (d, J=8.5, 1H), 7.63-7.54 (m, 3H), 7.45 (d, J=8.6, 1H), 5.04-4.90 (m, 1H), 4.56 (s, 2H), 3.94-3.84 (m, 2H), 3.62-3.51 (m, 2H), 2.11-2.00 (m, 2H), 1.77-1.62 (m, 2H).

5-[2-(1-Piperidin-4-yl-1H-pyrazol-4-ylamino)pyridin-4-yl]-2-(tetrahydropyran-4-yloxy)benzonitrile ("A16")

With tert-butyl 4-(4-aminopyrazol-1-yl)piperidine-1-carboxylate, tert-butyl 4-(4-{4-[3-cyano-4-(tetrahydropyran-4- yloxy)phenyl]pyridin-2-ylamino}pyrazol-1-yl)piperidine-1-carboxylate is obtained in 40% yield.

87 mg of the resultant tert-butyl ester are dissolved in 3 ml of dried dioxane, and 3 ml of 4 molar HCl in dioxane are added. The slightly yellow solution is left to stir at RT for 1 h.

The reaction solution is evaporated in a rotary evaporator, and the powdery residue is triturated with petroleum ether and ethyl acetate and filtered off with suction. The substance is freeze-dried a number of times, giving 38.8 mg of the desired product; HPLC-MS Rt. [min] 1.244; HPLC-MS [M+H] 445;

$^1$H NMR (500 MHz, DMSO-d$_6$) δ [ppm] 8.78 (s, 1H), 8.15 (d, J=5.4, 1H), 8.04 (d, J=4.5, 1H), 7.97 (d, 1H), 7.92 (dt, J=17.9, 8.9, 1H), 7.51-7.43 (m, 2H), 6.93 (dd, J=5.4, 1.5, 1H), 6.86 (s, 1H), 4.96-4.84 (m, 1H), 4.22-4.08 (m, 1H), 3.95-3.82 (m, 2H), 3.59-3.47 (m, 2H), 3.10-3.02 (m, 2H), 2.61 (td, J=12.3, 2.1, 2H), 2.08-1.98 (m, 2H), 1.98-1.89 (m, 2H), 1.84-1.73 (m, 2H), 1.73-1.61 (m, 2H).

2-{4-[3-Cyano-4-(tetrahydropyran-4-yloxy)phenyl]pyridin-2-ylamino}-isonicotinonitrile ("A17")

With 2-aminoisonicotinonitrile, the desired product is obtained in 9% yield; HPLC-MS Rt. [min] 1.719; HPLC-MS [M+H] 398;

$^1$H NMR (500 MHz, DMSO-d$_6$) δ [ppm] 10.34 (s, 1H), 8.49 (d, J=5.1, 1H), 8.36 (d, J=5.5, 1H), 8.25 (s, 1H), 8.13 (d, J=2.3, 1H), 8.00 (dd, J=8.9, 2.4, 1H), 7.80 (d, J=0.9, 1H), 7.53 (d, J=9.0, 1H), 7.39-7.33 (m, 1H), 7.31 (dd, J=5.1, 0.9, 1H), 4.92 (tt, J=7.8, 3.8, 1H), 3.91-3.82 (m, 2H), 3.56 (ddd, J=11.5, 8.4, 3.1, 2H), 2.08-1.98 (m, 2H), 1.74-1.63 (m, 2H).

5-[2-(4-Hydroxymethylpyridin-2-ylamino)pyridin-4-yl]-2-(tetrahydropyran-4-yloxy)benzonitrile ("A18")

With (2-aminopyridin-4-yl)methanol, the desired product is obtained in 60% yield; HPLC-MS Rt. [min] 1.567; HPLC-MS [M+H] 403;

$^1$H NMR (500 MHz, DMSO-d$_6$) δ [ppm] 11.52 (s, 1H), 8.41 (d, J=5.8, 1H), 8.29 (d, J=6.0, 1H), 8.21 (d, J=2.3, 1H), 8.05 (dd, J=8.9, 2.4, 1H), 7.55 (d, J=9.0, 3H), 7.43 (s, 1H), 7.13 (d, J=5.7, 1H), 5.56 (br, 1H), 4.99-4.88 (m, 1H), 4.65 (s, 2H), 3.93-3.83 (m, 2H), 3.63-3.49 (m, 2H), 2.11-1.97 (m, 2H), 1.77-1.61 (m, 2H).

5-{4-[3-Cyano-4-(tetrahydropyran-4-yloxy)phenyl]pyridin-2-ylamino}benzofuran-2-carboxamide ("A19")

With 5-aminobenzofuran-2-carboxamide, the desired product is obtained in 51% yield; HPLC-MS Rt. [min] 1.824; HPLC-MS [M+H] 455;

$^1$H NMR (500 MHz, DMSO-d$_6$) δ [ppm] 10.94 (br, 1H), 9.2 (br, 2H), 8.48 (d, J=5.2, 1H), 8.42 (d, J=1.0, 1H), 8.19 (d, J=2.4, 1H), 8.04 (dd, J=8.9, 2.4, 1H), 7.98 (s, 1H), 7.74 (d, J=8.8, 1H), 7.59-7.50 (m, 3H), 7.30 (dd, J=8.8, 1.9, 1H), 4.98-4.87 (m, 1H), 3.92-3.83 (m, 2H), 3.62-3.50 (m, 2H), 2.09-1.98 (m, 2H), 1.75-1.63 (m, 2H).

2-(Tetrahydropyran-4-yloxy)-5-[2-(5,6,7,8-tetrahydropyrido[4,3-d]pyrimidin-2-ylamino)pyridin-4-yl]benzonitrile ("A36")

2-Amino-5,6,7,8-tetrahydropyrido-[4,3-d]pyrimidine dihydrochloride (100 mg; 0.448 mmol) is dissolved in 10 ml of dichloromethane in a 50 ml flask, and di-tert-butyl dicarbonate (0.14 ml; 0.672 mmol) and triethylamine (0.062 ml; 0.448 mmol) are added with stirring. The reaction mixture is stirred at RT overnight. For work-up, the reaction mixture is evaporated. The residue is triturated in ethyl acetate and filtered off with suction. The filtrate is evaporated, giving 80 mg of tert-butyl 2-amino-7,8-dihydro-5H-pyrido[4,3-d]pyrimidine-6-carboxylate;

HPLC-MS Rt. [min] 1.504; HPLC-MS [M+H] 251;

With the tert-butyl 2-amino-7,8-dihydro-5H-pyrido[4,3-d]pyrimidine-6-carboxylate prepared, tert-butyl 2-{4-[3-cyano-4-(tetrahydropyran-4-yloxy)phenyl]pyridin-2-ylamino}-7,8-dihydro-5H-pyrido[4,3-d]pyrimidine-6-carboxylate is obtained under Buchwald-Hartwig conditions.

tert-Butyl 2-{4-[3-cyano-4-(tetrahydropyran-4-yloxy)phenyl]pyridin-2-ylamino}-7,8-dihydro-5H-pyrido[4,3-d]pyrimidine-6-carboxylate (155 mg; 0.241 mmol) are dissolved in 3.5 ml of dried dioxane, and 3 ml of HCl in dioxane (4 mol/l) are added.

The yellow solution is stirred at room temperature for 30 min.

The reaction mixture is rendered basic using 2 molar NaOH. The precipitate is filtered off with suction and washed with dioxane, giving 97 mg of the desired product; HPLC-MS Rt. [min] 1.223; HPLC-MS [M+H] 429;
NMR 6-{4-[3-Cyano-4-(tetrahydropyran-4-yloxy)phenyl]pyridin-2-ylamino}nicotinamide ("A37")

With 6-aminonicotinamide, the desired product is obtained in 5% yield; HPLC-MS Rt. [min] 1.476; HPLC-MS [M+H] 416;

$^1$H NMR (500 MHz, DMSO-d$_6$) δ [ppm] 10.90 (s, 1H), 8.68 (d, J=1.9, 1H), 8.44 (d, J=5.3, 1H), 8.41 (d, J=1.0, 1H), 8.28 (dd, J=9.1, 2.0, 1H), 8.16 (d, J=2.4, 1H), 8.02 (dd, J=8.9, 2.4, 1H), 7.98-7.63 (m, 1H), 7.57-7.49 (m, 2H), 6.85 (d, J=9.1, 1H), 4.98-4.87 (m, 1H), 3.92-3.83 (m, 2H), 3.60-3.51 (m, 2H), 2.10-1.97 (m, 2H), 1.76-1.61 (m, 2H).

Synthesis Scheme 2

Preparation of 1H-pyrazol-4-ylamine derivatives

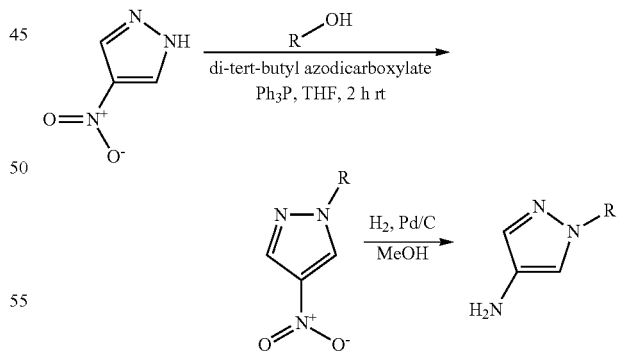

General Procedure:

4-Nitro-1H-pyrazole (4.422 mmol; 500.00 mg), 1 equivalent of the primary alcohol and 1.77 g of triphenylphosphine are dissolved in 20 ml of dried THF in a 100 ml three-necked flask with drying tube under N$_2$. Di-tert-butyl azodicarboxylate (5.748 mmol; 1.35 g) is subsequently added in portions. The yellow solution is stirred at RT for 2 h.

For work-up, the triphenylphosphine oxide is filtered off with suction, and the filtrate is evaporated in a rotary evaporator. The 4-nitro-1H-pyrazole derivative is, if necessary, chromatographed over silica gel in ethyl acetate/petroleum ether. The 4-nitro-1H-pyrazole derivative is dissolved in methanol, 5% Pd/C is added, and the mixture is hydrogenated at room temperature using hydrogen. The 1H-pyrazol-4-ylamine derivative is obtained after filtration and evaporation of the solution.

1-(2,2-Difluoroethyl)-1H-pyrazol-4-ylamine is prepared using 2,2-difluoroethanol;
HPLC-MS Rt. [min] 0.351; HPLC-MS [M+H] 148.

tert-Butyl 4-[2-(4-aminopyrazol-1-yl)ethyl]piperidine-1-carboxylate is prepared using tert-butyl 4-(2-hydroxyethyl)piperidine-1-carboxylate;
HPLC-MS Rt. [min] 1.357; HPLC-MS [M+H] 295.

1-(2-Morpholin-4-ylethyl)-1H-pyrazol-4-ylamine is prepared using N-(2-hydroxyethyl)morpholine; HPLC-MS Rt. [min] 0.320; HPLC-MS [M+H] 197.

1-(3-Methoxypropyl)-1H-pyrazol-4-ylamine is prepared using 3-methoxy-1-propanol; HPLC-MS Rt. [min] 0.363; HPLC-MS [M+H] 155.

2-(4-Aminopyrazol-1-ylmethyl)cyclopropanecarbonitrile is prepared using 2-hydroxymethylcyclopropanecarbonitrile; HPLC-MS Rt. [min] 0.380; HPLC-MS [M+H] 163.

tert-Butyl 3-(4-aminopyrazol-1-yl)azetidine-1-carboxylate is prepared using tert-butyl 3-hydroxyazetidine-1-carboxylate; HPLC-MS Rt. [min] 1.117;
HPLC-MS [M+H] 183.

[trans-2-(4-Aminopyrazol-1-ylmethyl)cyclopropyl]methanol is prepared using trans-2-hydroxymethylcyclopropyl)methanol; HPLC-MS Rt. [min] 0.355;
HPLC-MS [M+H] 168.

1-(Tetrahydrofuran-3-ylmethyl)-1H-pyrazol-4-ylamine is prepared using (tetrahydro-furan-3-yl)methanol; HPLC-MS Rt. [min] 0.357; HPLC-MS [M+H] 168.

tert-Butyl 3-(4-aminopyrazol-1-yl)pyrrolidine-1-carboxylate is prepared using tert-butyl 3-hydroxypyrrolidine-1-carboxylate; HPLC-MS Rt. [min] 1.099;
HPLC-MS [M+H] 253.

1-(2-Pyrazol-1-ylethyl)-1H-pyrazol-4-ylamine is prepared using 2-(1H-pyrazol-1-yl)ethanol; HPLC-MS Rt. [min] 0.355; HPLC-MS [M+H] 178.

Preparation of Compounds of the Formula I

5-{2-[1-(2,2-Difluoroethyl)-1H-pyrazol-4-ylamino]pyridin-4-yl}-2-(tetrahydropyran-4-yloxy)benzonitrile ("A20")

With the 1-(2,2-difluoroethyl)-1H-pyrazol-4-ylamine described above, the desired product is obtained in 34% yield; HPLC-MS Rt. [min] 1.619; HPLC-MS [M+H] 426;
$^1$H NMR (500 MHz, DMSO-$d_6$) δ [ppm] 8.94 (s, 1H), 8.16 (d, J=8.1, 1H), 8.10 (s, 1H), 8.06 (d, J=2.4, 1H), 7.94 (dd, J=8.9, 2.4, 1H), 7.55 (s, 1H), 7.47 (d, J=10.1, 1 H), 6.97 (dd, J=5.4, 1.5, 1H), 6.89 (d, J=0.7, 1H), 6.33 (tt, J=55.1, 3.9, 1H), 4.95-4.83 (m, 1H), 4.66-4.50 (m, 2H), 3.93-3.82 (m, 2H), 3.62-3.48 (m, 2H), 2.08-1.96 (m, 2H), 1.74-1.60 (m, 2H).

5-{2-[1-(2-Piperidin-4-ylethyl)-1H-pyrazol-4-ylamino]pyridin-4-yl}-2-(tetrahydropyran-4-yloxy)benzonitrile ("A21")

With the tert-butyl 4-[2-(4-aminopyrazol-1-yl)ethyl]piperidine-1-carboxylate prepared above, tert-butyl 4-[2-(4-{4-[3-cyano-4-(tetrahydropyran-4-yloxy)phenyl]-pyridin-2-ylamino}pyrazol-1-yl)ethyl]piperidine-1-carboxylate is obtained in 41% yield.

210 mg of tert-butyl 4-[2-(4-{4-[3-cyano-4-(tetrahydropyran-4-yloxy)phenyl]pyridin-2-ylamino}pyrazol-1-yl)ethyl]piperidine-1-carboxylate are dissolved in 5 ml of dried dioxane, and 5 ml of HCl in dioxane (4 mol/l) are added. The yellow solution is stirred at room temperature for 30 min.

The reaction mixture is rendered basic using 2 molar NaOH and extracted. The combined organic phases are dried, filtered and evaporated, giving 150 mg of the desired compound; HPLC-MS Rt. [min] 1.274;
HPLC-MS [M+H] 473;
$^1$H NMR (500 MHz, DMSO-$d_6$) δ [ppm] 8.78 (d, 1H), 8.15 (d, J=5.4, 1H), 8.04 (d, J=2.4, 1H), 7.97 (s, 1H), 7.92 (dd, J=8.9, 2.4, 1H), 7.47 (d, J=9.1, 1H), 7.44 (s, 1H), 6.93 (dd, J=5.4, 1.6, 1H), 6.86 (d, J=0.8, 1H), 4.96-4.82 (m, 1H), 4.15-4.04 (m, 2H), 3.91-3.81 (m, 2H), 3.59-3.51 (m, 2H), 2.99-2.85 (m, 2H), 2.47-2.36 (m, 2H), 2.10-1.96 (m, 2H), 1.74-1.52 (m, 6H), 1.34-0.98 (m, 3H).

5-{2-[1-(2-Morpholin-4-ylethyl)-1H-pyrazol-4-ylamino]pyridin-4-yl}-2-(tetrahydropyran-4-yloxy)benzonitrile ("A22")

With the 1-(2-morpholin-4-ylethyl)-1H-pyrazol-4-ylamine prepared above, the desired product is obtained in 42% yield; HPLC-MS Rt. [min] 1.307;
HPLC-MS [M+H] 475;
$^1$H NMR (500 MHz, DMSO-$d_6$) δ [ppm] 9.03 (br, 1H), 8.20-8.13 (m, 2H), 8.08 (d, J=2.3, 1H), 7.96 (dd, J=8.9, 2.4, 1H), 7.58 (s, 1H), 7.50 (d, J=9.1, 1H), 7.01 (d, J=5.0, 1H), 6.93 (s, 1H), 4.96-4.85 (m, 1H), 4.53 (t, J=6.1, 2H), 3.96-3.83 (m, 6H), 3.61-3.52 (m, 8H), 2.08-1.97 (m, 2H), 1.75-1.57 (m, 2H).

5-{2-[1-(3-Methoxypropyl)-1H-pyrazol-4-ylamino]pyridin-4-yl}-2-(tetrahydropyran-4-yloxy)benzonitrile ("A23")

With the 1-(3-methoxypropyl)-1H-pyrazol-4-ylamine prepared above, the desired product is obtained in 16% yield; HPLC-MS Rt. [min] 1.565;
HPLC-MS [M+H] 434;
$^1$H NMR (500 MHz, DMSO-$d_6$) δ [ppm] 9.41 (br, 1H), 8.17 (d, J=2.0, 1H), 8.06 (d, J=6.0, 1H), 8.02-7.97 (m, 2H), 7.55 (s, 1H), 7.51 (d, J=9.1, 1H), 7.16 (s, 1H), 7.07 (s, 1H), 5.01-4.84 (m, 1H), 4.14 (t, J=7.0, 2H), 3.91-3.78 (m, 3H), 3.32 (t, J=6.2, 2H), 3.24 (s, 3H), 2.11-1.95 (m, 4H), 1.76-1.58 (m, 2H).

5-{2-[1-(2-Cyanocyclopropylmethyl)-1H-pyrazol-4-ylamino]pyridin-4-yl}-2-(tetrahydropyran-4-yloxy)benzonitrile ("A24")

With the 2-(4-aminopyrazol-1-ylmethyl)cyclopropanecarbonitrile prepared above, the desired product is obtained in 28% yield; HPLC-MS Rt. [min] 1.573;
HPLC-MS [M+H] 431;
$^1$H NMR (500 MHz, DMSO-$d_6$) δ [ppm] 9.49 (br, 1H), 8.17 (d, J=2.2, 1H), 8.08 (d, J=6.0, 1H), 8.06 (s, 1H), 8.00 (dd, J=8.9, 2.4, 1H), 7.59 (s, 1H), 7.51 (d, J=9.1, 1H), 7.15 (d, J=5.5, 1H), 7.09 (s, 1H), 4.98-4.86 (m, 1H), 4.18-4.10 (m, 1H), 4.10-4.00 (m, 1H), 3.92-3.82 (m, 2H), 3.60-3.49 (m, 2H), 2.07-1.90 (m, 3H), 1.86-1.78 (m, 1H), 1.74-1.63 (m, 2H), 1.35-1.27 (m, 1H), 1.17-1.09 (m, 1H).

5-[2-(1-Azetidin-3-yl-1H-pyrazol-4-ylamino)pyridin-4-yl]-2-(tetrahydropyran-4-yloxy)benzonitrile ("A25")

With the tert-butyl 3-(4-aminopyrazol-1-yl)azetidine-1-carboxylate prepared above, tert-butyl 3-(4-{4-[3-cyano-4-

(tetrahydropyran-4-yloxy)phenyl]pyridin-2-ylamino}-pyrazol-1-yl)azetidine-1-carboxylate is obtained in 18% yield.

71 mg of tert-butyl 3-(4-{4-[3-cyano-4-(tetrahydropyran-4-yloxy)phenyl]pyridin-2-ylamino}pyrazol-1-yl)azetidine-1-carboxylate are dissolved in 3 ml of dioxane, and 3 ml of HCl in dioxane (4 molar) are added. The yellow solution is stirred at room temperature for 30 min.

For work-up, the reaction solution is rendered basic using 2 molar NaOH and extracted with ethyl acetate. The combined organic phases are dried, filtered and evaporated. Chromatography on silica gel gives 27 mg of the desired compound; HPLC-MS Rt. [min] 1.255; HPLC-MS [M+H] 417.

5-{2-[1-((1S,2S)-2-Hydroxymethylcyclopropylmethyl)-1H-pyrazol-4-ylamino]-pyridin-4-yl}-2-(tetrahydropyran-4-yloxy)benzonitrile ("A26")

With the [trans-2-(4-aminopyrazol-1-ylmethyl)cyclopropyl]methanol prepared above, the desired product is obtained in 35% yield; HPLC-MS Rt. [min] 1.490; HPLC-MS [M+H] 446;

$^1$H NMR (500 MHz, DMSO-$d_6$) δ [ppm] 9.45 (s, 1H), 8.18 (s, 1H), 8.11-7.95 (m, 2H), 7.58-7.48 (m, 2H), 7.16 (s, 1H), 7.09 (s, 1H), 4.99-4.86 (m, 1H), 4.08-3.93 (m, 2H), 3.87 (dt, J=10.3, 3.5, 2H), 3.61-3.48 (m, 2H), 3.35 (dd, J=11.2, 6.1, 1 H), 3.26 (dd, J=11.2, 6.5, 1H), 2.07-1.96 (m, 2H), 1.73-1.62 (m, 2H), 1.19-0.99 (m, 2H), 0.59-0.38 (m, 2H).

5-{2-[1-(Tetrahydrofuran-3-ylmethyl)-1H-pyrazol-4-ylamino]pyridin-4-yl}-2-(tetrahydropyran-4-yloxy)benzonitrile ("A27")

With the 1-(tetrahydrofuran-3-ylmethyl)-1H-pyrazol-4-ylamine prepared above, the desired product is obtained in 37% yield; HPLC-MS Rt. [min] 1.536;

HPLC-MS [M+H] 446;

$^1$H NMR (500 MHz, DMSO-$d_6$) δ [ppm] 9.51 (s, 1H), 8.18 (d, J=1.6, 1H), 8.09-8.03 (m, 2H), 8.01 (dd, J=8.9, 2.3, 1H), 7.57 (s, 1H), 7.52 (d, J=9.1, 1H), 7.18 (d, J=4.2, 1H), 7.10 (s, 1H), 4.98-4.87 (m, 1H), 4.17-4.04 (m, 2H), 3.90-3.83 (m, 2H), 3.77 (td, J=8.1, 5.7, 1H), 3.71-3.60 (m, 2H), 3.60-3.45 (m, 3H), 2.79-2.67 (m, 1H), 2.08-1.99 (m, 2H), 1.99-1.86 (m, 1H), 1.74-1.53 (m, 3H).

5-[2-(1-Pyrrolidin-3-yl-1H-pyrazol-4-ylamino)pyridin-4-yl]-2-(tetrahydropyran-4-yloxy)benzonitrile ("A28")

With the tert-butyl 3-(4-aminopyrazol-1-yl)pyrrolidine-1-carboxylate prepared above, tert-butyl 3-(4-{4-[3-cyano-4-(tetrahydropyran-4-yloxy)phenyl]pyridin-2-ylamino}pyrazol-1-yl)pyrrolidine-1-carboxylate is obtained in 68% yield.

110 mg of tert-butyl 3-(4-{4-[3-cyano-4-(tetrahydropyran-4-yloxy)phenyl]pyridin-2-ylamino}pyrazol-1-yl)pyrrolidine-1-carboxylate are dissolved in 3 ml of dried dioxane, and 3 ml of HCl in dioxane (4 mol/l) are added. The yellow solution is stirred at room temperature for 30 min.

For work-up, the reaction mixture is rendered basic using 2 molar NaOH. The solution is evaporated in a rotary evaporator and chromatographed, giving 100 mg of the desired product; HPLC-MS Rt. [min] 1.288; HPLC-MS [M+H] 431;

$^1$H NMR (500 MHz, DMSO-$d_6$) δ [ppm] 8.93 (s, 1H), 8.17 (d, J=5.4, 1H), 8.11 (s, 1H), 8.07 (d, J=2.4, 1H), 7.95 (dd, J=8.9, 2.4, 1H), 7.55 (s, 1H), 7.50 (d, J=9.1, 1 H), 6.97 (dd, J=5.4, 1.5, 1H), 6.91 (s, 1H), 5.09-5.00 (m, 1H), 4.95-4.86 (m, 1H), 3.93-3.82 (m, 2H), 3.60-3.52 (m, 2H), 3.51-3.43 (m, 2H), 3.22-3.12 (m, 2H), 2.35-2.27 (m, 1H), 2.22-2.13 (m, 1H), 2.08-1.99 (m, 2H), 1.74-1.63 (m, 2H).

5-{2-[1-(2-Pyrazol-1-ylethyl)-1H-pyrazol-4-ylamino]pyridin-4-yl}-2-(tetrahydropyran-4-yloxy)benzonitrile ("A38")

With the 1-(2-pyrazol-1-ylethyl)-1H-pyrazol-4-ylamine prepared above, the desired product is obtained in 46% yield; HPLC-MS Rt. [min] 1.538;

HPLC-MS [M+H] 456;

$^1$H NMR (500 MHz, DMSO-$d_6$) δ [ppm] 9.43 (s, 1H), 8.17 (d, J=1.7, 1H), 8.07 (d, J=6.1, 1H), 8.00 (dd, J=8.9, 2.3, 1H), 7.75 (s, 1H), 7.59 (s, 1H), 7.55-7.51 (m, 2H), 7.45 (d, J=1.5, 1H), 7.17 (s, 1H), 7.00 (s, 1H), 6.16 (t, J=2.0, 1H), 4.99-4.89 (m, 1H), 4.61-4.48 (m, 4H), 3.91-3.82 (m, 2H), 3.62-3.51 (m, 2H), 2.10-1.99 (m, 2H), 1.73-1.62 (m, 2H).

5-[2-(1-{2-[1-(2-Hydroxyacetyl)piperidin-4-yl]ethyl}-1H-pyrazol-4-ylamino)pyridin-4-yl]-2-(tetrahydropyran-4-yloxy)benzonitrile ("A29")

5-{2-[1-(2-Piperidin-4-ylethyl)-1H-pyrazol-4-ylamino]pyridin-4-yl}-2-(tetrahydropyran-4-yloxy)benzonitrile (0.060 mmol; 30.00 mg) and glycolic acid (0.072 mmol; 5.50 mg) are dissolved in 5 ml of DMF in a 50 ml flask, and HATU (0.090 mmol; 34.40 mg) and 4-methylmorpholine (0.181 mmol; 0.02 ml) are added. The beige solution is stirred at room temperature for 4.5 h.

For work-up, the DMF is removed in a rotary evaporator, and the residue is extracted with ethyl acetate and 2 molar NaOH. The organic phases are dried, filtered and evaporated.

The crude product obtained is chromatographed over silica gel (dichloromethane, methanol), giving 32 mg of the desired product; HPLC-MS Rt. [min] 1.527

HPLC-MS [M+H] 531;

$^1$H NMR (500 MHz, DMSO-$d_6$) δ [ppm] 11.94 (br, 1H), 8.79 (s, 1H), 8.15 (d, J=5.4, 1 H), 8.05 (d, J=2.4, 1H), 7.99 (s, 1H), 7.92 (dd, J=8.9, 2.4, 1H), 7.51-7.40 (m, 1H), 6.94 (dd, J=5.4, 1.3, 1H), 6.86 (s, 1H), 4.94-4.84 (m, 1H), 4.40 (s, 1H), 4.30 (d, J=12.6, 1H), 4.11 (t, J=7.1, 2H), 4.07-3.99 (m, 2H), 3.91-3.82 (m, 2H), 3.66-3.58 (m, 1H), 3.58-3.49 (m, 2H), 2.87 (t, J=12.3, 1H), 2.59-2.50 (m, 1H), 2.10-1.97 (m, 2H), 1.78-1.61 (m, 5H), 1.51-1.37 (m, 1H), 1.16-0.91 (m, 3H).

5-[2-(1-{2-[1-(2-Aminoacetyl)piperidin-4-yl]ethyl}-1H-pyrazol-4-ylamino)pyridin-4-yl]-2-(tetrahydropyran-4-yloxy)benzonitrile ("A30")

5-{2-[1-(2-Piperidin-4-ylethyl)-1H-pyrazol-4-ylamino]pyridin-4-yl}-2-(tetrahydropyran-4-yloxy)benzonitrile (0.121 mmol; 60.00 mg) and BOC-glycine (0.145 mmol; 25.36 mg) are dissolved in 10 ml of DMF in a 50 ml flask, HATU (0.181 mmol; 68.79 mg) and 4-methylmorpholine (0.362 mmol; 0.04 ml; 3.00 eq.) are added. The pale-yellow solution is stirred at room temperature for 2 h.

For work-up, the DMF is evaporated in a rotary evaporator, and residue is extracted with ethyl acetate and 2 molar NaOH. The combined organic phases are dried, filtered and evaporated, giving 127 mg of yellow oil of tert-butyl(2-{4-[2-(4-{4-[3-cyano-4-(tetrahydropyran-4-yloxy)phenyl]pyridin-2-ylamino}pyrazol-1-yl)ethyl]piperidin-1-yl}-2-oxoethyl) carbamate.

These are dissolved in 5 ml of dioxane, and 3 ml of HCl in dioxane (4 molar) are added. The yellow solution is stirred at room temperature for 1 h.

For work-up, the reaction solution is rendered basic using 2 molar NaOH, diluted with ethyl acetate and extracted. The combined organic phases are dried, filtered and evaporated.

The crude product obtained is purified by chromatography (silica gel, dichloromethane/methanol), giving 35 mg of the desired product; HPLC-MS Rt. [min] 1.323; HPLC-MS [M+H] 530;

$^1$H NMR (500 MHz, DMSO-$d_6$) δ [ppm] 8.79 (d, 1H), 8.14 (d, J=6.0, 1H), 8.04 (d, J=2.3, 1H), 7.99 (s, 1H), 7.92 (dd, J=8.9, 2.3, 1H), 7.47 (d, J=6.3, 1H), 7.46 (s, 1H), 6.94 (dd, J=5.4, 1.4, 1H), 6.86 (s, 1H), 4.95-4.84 (m, 1H), 4.31 (s, 1H), 4.11 (t, J=7.1, 2H), 3.92-3.82 (m, 2H), 3.67 (d, J=12.4, 1H), 3.60-3.43 (m, 4H), 2.98-2.82 (m, 1H), 2.59-2.52 (m, 1H), 2.09-1.98 (m, 2H), 1.79-1.61 (m, 6H), 1.54-1.35 (m, 1H), 1.17-0.93 (m, 3H).

Synthesis Using Potassium Tert-Butoxide

5-[2-(3-tert-Butylisoxazol-5-ylamino)pyridin-4-yl]-2-(tetrahydropyran-4-yloxy)benzonitrile ("A31")

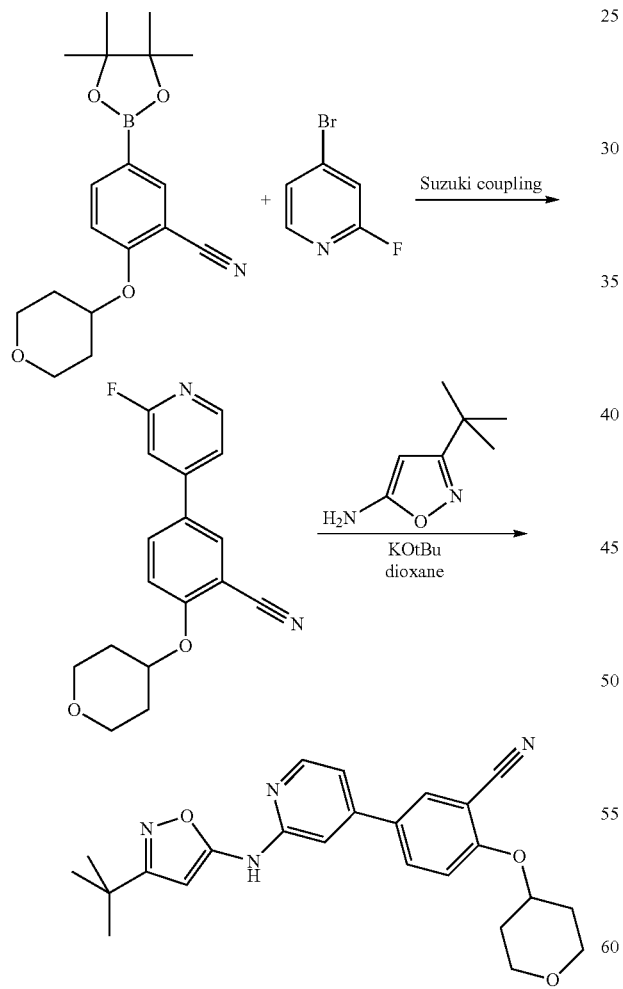

2-(Tetrahydropyran-4-yloxy)-5-(4,4,5,5-tetramethyl-1,3,2-dioxaborolan-2-yl)benzonitrile (6.766 mmol; 2.75 g) and 4-bromo-2-fluoropyridine (6.766 mmol; 0.77 ml) are dissolved in 25 ml of dioxane and 10 ml of water in a 100 ml three-necked flask under N$_2$, and 1.87 g of potassium carbonate and 392 mg of tetrakis(triphenylphosphine)palladium(0) are added. The dark-brown solution is stirred at 90° C. for 2.5 h.

For work-up, the reaction mixture is cooled to room temperature and diluted with water and ethyl acetate and extracted. The combined organic phases are washed with saturated NaCl solution, dried, filtered and evaporated, giving 3.5 g of crude product, which is chromatographed over silica gel (ethyl acetate/petroleum ether) for purification, giving 2.1 g of 5-(2-fluoropyridin-4-yl)-2-(tetrahydropyran-4-yloxy)benzonitrile; HPLC-MS Rt. [min] 2.135; HPLC-MS [M+H] 299;

100 mg of 5-(2-fluoropyridin-4-yl)-2-(tetrahydropyran-4-yloxy)benzonitrile are suspended in 6 ml of dioxane in a 50 ml three-necked flask under N$_2$, 52 mg of 3-tert-butylisoxazol-5-ylamine and 79 mg of KOtBu are added. The yellow solution is stirred at 80° C. for 2.5 h. For work-up, the reaction mixture is evaporated in a rotary evaporator, the residue is taken up in ethyl acetate and water and extracted. The collected organic phases are dried, filtered and evaporated. The crude product is purified by preparative HPLC, giving the desired product in 46% yield; HPLC-MS Rt. [min] 2.556; HPLC-MS [M+H] 419;

$^1$H NMR (500 MHz, DMSO-$d_6$) δ [ppm] 8.36 (d, J=5.7, 1H), 8.19 (d, J=2.4, 1H), 8.04 (dd, J=8.9, 2.4, 1H), 7.53 (d, J=9.1, 1H), 7.42 (dd, J=5.8, 1.6, 1H), 7.38 (s, 1H), 5.00-4.88 (m, 1H), 3.96-3.85 (m, 2H), 3.64-3.50 (m, 2H), 2.12-2.00 (m, 2H), 1.79-1.66 (m, 2H), 1.38-1.24 (s, 9H).

Synthesis of 5-{2-[5-(1H-pyrazol-4-yl)pyridin-2-ylamino]pyridin-4-yl}-2-(tetrahydropyran-4-yloxy)benzonitrile ("A9")

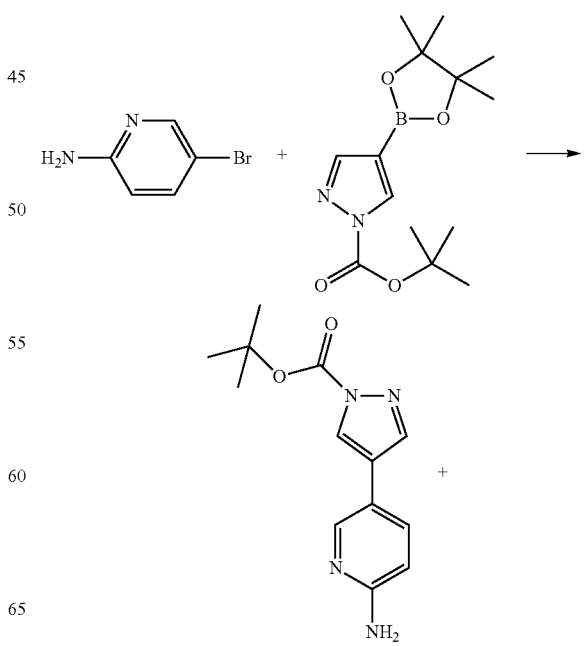

-continued

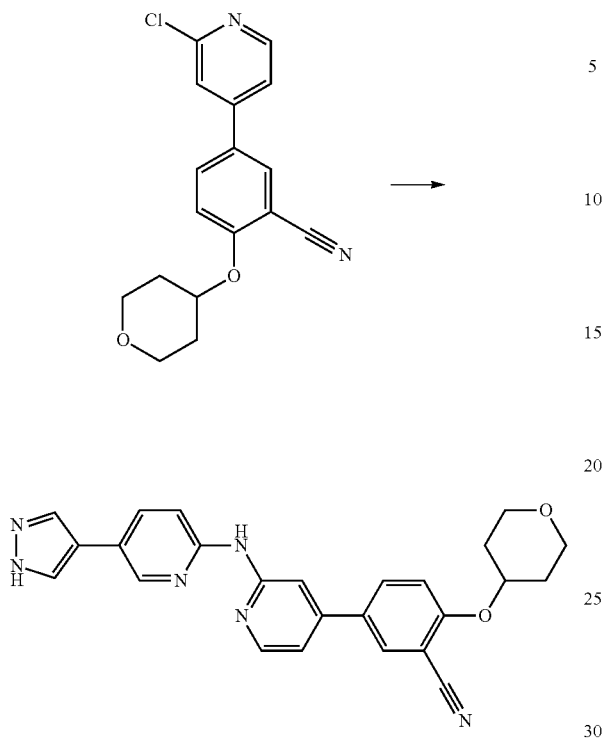

5-Bromopyridin-2-ylamine (200 mg; 1.156 mmol) and tert-butyl 4-(4,4,5,5-tetramethyl-1,3,2-dioxaborolan-2-yl)pyrazole-1-carboxylate (420.670 mg; 1.387 mmol) are dissolved in 3 ml of dioxane and 1 ml of water in a 50 ml three-necked flask under $N_2$, and potassium carbonate (0.131 ml; 2.312 mmol) and tetrakis(triphenylphosphine)palladium (0) (133.5 mg; 0.116 mmol) are added. The solution is stirred at 90° C. overnight.

For work-up, the reaction mixture is cooled to room temperature, diluted with water and extracted with ethyl acetate. The combined organic phases are dried using sodium sulfate, filtered, and the solvent is evaporated in a rotary evaporator. The residue is purified by chromatography (silica gel dichloromethane/methanol), giving 249 mg of tert-butyl 4-(6-aminopyridin-3-yl)pyrazole-1-carboxylate; HPLC-MS Rt. [min] 1.304; HPLC-MS [M+H] 261.

85 mg of tert-butyl 4-(6-aminopyridin-3-yl)pyrazole-1-carboxylate are reacted with 100 mg of 5-(2-chloropyridin-4-yl)-2-(tetrahydropyran-4-yloxy)benzonitrile in accordance with the above-mentioned general procedure for the Buchwald-Hartwig reaction, giving the desired product in 16% yield;

HPLC-MS Rt. [min] 1.648; HPLC-MS [M+H] 439;

$^1$H NMR (500 MHz, DMSO-$d_6$) δ [ppm] 9.69 (s, 1H), 8.54 (d, J=2.0, 1H), 8.28 (d, J=5.2, 1H), 8.08 (d, J=10.4, 1H), 8.00-7.95 (m, 2H), 7.90 (dd, J=8.7, 2.4, 2H), 7.80 (d, J=8.7, 1H), 7.52 (d, J=9.1, 1H), 7.20 (dd, J=5.3, 1.6, 1H), 4.96-4.83 (m, 1H), 3.92-3.83 (m, 2H), 3.60-3.52 (m, 2H), 2.08-1.98 (m, 2H), 1.76-1.64 (m, 2H).

Synthesis Scheme 2

General synthetic route for compounds of the formula I in which X=N.

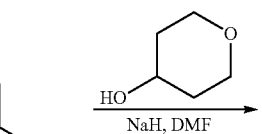

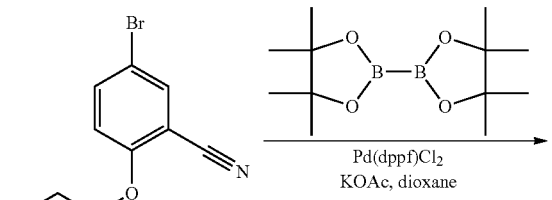

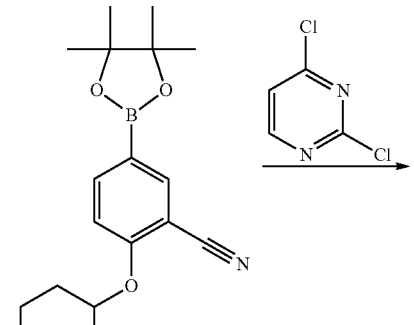

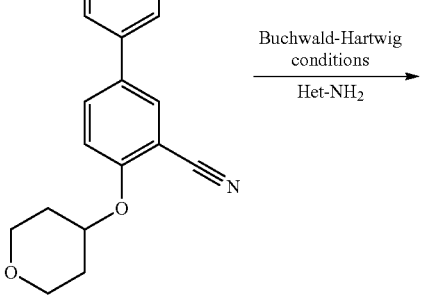

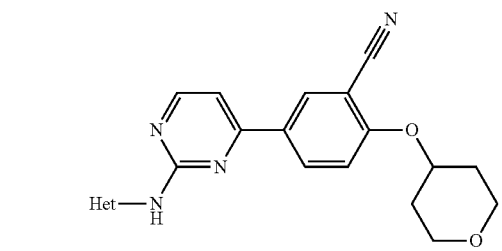

5-(2-Chloropyrimidin-4-yl)-2-(tetrahydropyran-4-yloxy)benzonitrile is prepared as described in WO 2011/046970 A1.

Preparation of Compounds of the Formula I by the Buchwald-Hartwig Method

2-(Tetrahydropyran-4-yloxy)-5-{2-[1-(3-trifluoromethylphenyl)-1H-pyrazol-4-yl-amino]pyrimidin-4-yl}benzonitrile ("A32")

With 1-[3-(trifluoromethyl)phenyl]-1H-pyrazol-4-amine, the desired product is obtained in a yield of 12%; HPLC-MS Rt. [min] 2.717; HPLC-MS [M+H] 507;
$^1$H NMR (500 MHz, DMSO-$d_6$) δ [ppm] 9.80 (s, 1H), 8.75 (s, 1H), 8.60-8.54 (m, 2H), 8.45 (dd, J=9.0, 2.2, 1H), 8.17-8.10 (m, 2H), 7.98 (s, 1H), 7.74 (t, J=7.9, 1 H), 7.64 (d, J=7.8, 1H), 7.53 (d, J=9.1, 1H), 7.43 (d, J=5.2, 1H), 5.00-4.89 (m, 1H), 3.92-3.83 (m, 2H), 3.60-3.51 (m, 2H), 2.10-1.99 (m, 2H), 1.75-1.63 (m, 2H).

5-[2-(1-Methyl-1H-pyrazol-3-ylamino)pyrimidin-4-yl]-2-(tetrahydropyran-4-yloxy)benzonitrile ("A33")

With 1-methyl-1H-pyrazol-3-amine, the desired product is obtained in 36% yield; HPLC-MS Rt. [min] 1.956; HPLC-MS [M+H] 377;
$^1$H NMR (500 MHz, DMSO-$d_6$) δ [ppm] 9.70 (s, 1H), 8.49 (dd, J=5.8, 3.7, 2H), 8.42 (dd, J=9.0, 2.3, 1H), 7.58 (d, J=2.2, 1H), 7.53 (d, J=9.1, 1H), 7.39 (d, J=5.2, 1H), 6.62 (d, J=2.2, 1H), 5.01-4.84 (m, 1H), 3.95-3.81 (m, 2H), 3.76 (s, 3H), 3.62-3.49 (m, 2H), 2.13-1.98 (m, 2H), 1.78-1.59 (m, 2H).

5-[2-(1H-Pyrazol-4-ylamino)pyrimidin-4-yl]-2-(tetrahydropyran-4-yloxy)benzonitrile ("A34")

With tert-butyl 4-aminopyrazole-1-carboxylate, the desired product is obtained in 4% yield; HPLC-MS Rt. [min] 1.804; HPLC-MS [M+H] 363;
$^1$H NMR (500 MHz, DMSO-$d_6$) δ [ppm] 9.47 (s, 1H), 8.48 (m, 2H), 8.41 (dd, J=9.0, 2.2, 1H), 7.79 (s, 2H), 7.53 (d, J=9.1, 1H), 7.32 (d, J=5.2, 1H), 4.97-4.87 (m, 1H), 3.92-3.82 (m, 2H), 3.60-3.49 (m, 2H), 2.10-1.99 (m, 2H), 1.75-1.63 (m, 2H).

5-{2-[1-(2-Methoxyethyl)-1H-pyrazol-4-ylamino]pyrimidin-4-yl}-2-(tetrahydropyran-4-yloxy)benzonitrile ("A35")

16 mg of 5-[2-(1H-pyrazol-4-ylamino)pyrimidin-4-yl]-2-(tetrahydropyran-4-yloxy)benzonitrile are dissolved in 1 ml of dried acetonitrile in a 50 ml flask provided with magnetic stirrer, condenser and drying tube, 9 mg of bromoethyl methyl ether and 28 mg of $Cs_2CO_3$ are added, and the suspension is stirred at a bath temperature of 90° C. The reaction mixture is stirred at 90° C. for 5 hours and at room temperature overnight.

For work-up, the mixture is evaporated in a rotary evaporator and purified by preparative HPLC, giving 8 mg of the desired product; HPLC-MS Rt. [min] 1.957 HPLC-MS [M+H] 421;
$^1$H NMR (500 MHz, DMSO-$d_6$) δ [ppm] 9.48 (s, 1H), 8.51-8.45 (m, 2H), 8.42 (dd, J=9.0, 2.2, 1H), 7.94 (s, 1H), 7.59 (s, 1H), 7.52 (d, J=9.1, 1H), 7.34 (d, J=5.2, 1H), 4.99-4.90 (m, 1H), 4.24 (t, J=5.3, 2H), 3.91-3.82 (m, 2H), 3.68 (t, J=5.3, 2H), 3.56 (ddd, J=11.5, 8.4, 3.1, 2H), 3.24 (s, 3H), 2.09-1.98 (m, 2H), 1.75-1.63 (m, 2H).

5-{2-[1-(2-Morpholin-4-ylethyl)-1H-pyrazol-4-ylamino]pyrimidin-4-yl}-2-(tetrahydropyran-4-yloxy)benzonitrile ("A39")

With 1-(2-morpholin-4-ylethyl)-1H-pyrazol-4-ylamine, the desired product is obtained in 7% yield; HPLC-MS Rt. [min] 1.537; HPLC-MS [M+H] 476;
$^1$H NMR (500 MHz, DMSO-$d_6$) δ [ppm] 9.62 (s, 1H), 8.54-8.47 (m, 2H), 8.41 (dd, J=9.0, 2.2, 1H), 8.06 (s, 1H), 7.70 (s, 1H), 7.52 (d, J=9.1, 1H), 7.36 (d, J=6.2, 1H), 5.01-4.86 (m, 1H), 4.54 (t, J=6.3, 2H), 3.92-3.84 (m, 4H), 3.65-3.50 (m, 6H), 3.42 (br, 2H), 3.19 (br, 2H), 2.10-1.99 (m, 2H), 1.77-1.61 (m, 2H).

5-[2-(1-Pyrrolidin-3-yl-1H-pyrazol-4-ylamino)pyrimidin-4-yl]-2-(tetrahydropyran-4-yloxy)benzonitrile ("A40")

With the tert-butyl 3-(4-aminopyrazol-1-yl)pyrrolidine-1-carboxylate prepared above, tert-butyl 3-(4-{4-[3-cyano-4-(tetrahydropyran-4-yloxy)phenyl]pyrimidin-2-ylamino}pyrazol-1-yl)pyrrolidine-1-carboxylate is obtained in 12% yield.

41 mg of tert-butyl 3-(4-{4-[3-cyano-4-(tetrahydropyran-4-yloxy)phenyl]pyrimidin-2-ylamino}pyrazol-1-yl)pyrrolidine-1-carboxylate are dissolved in 1 ml of dried dioxane, and 1 ml of HCl in dioxane (4 mol/1) is added. The yellow solution is stirred at room temperature for 60 min.

For work-up, the reaction mixture is rendered basic using 2 molar NaOH. The solution is evaporated in a rotary evaporator and chromatographed, giving 22 mg of the desired product; HPLC-MS Rt. [min] 1.522; HPLC-MS [M+H] 432;
$^1$H NMR (500 MHz, DMSO-$d_6$) δ [ppm] 9.59 (s, 1H), 9.00 (d, J=21.0, 2H), 8.54-8.46 (m, 2H), 8.41 (dd, J=9.0, 2.2, 1H), 8.08 (s, 1H), 7.71 (s, 1H), 7.52 (d, J=9.1, 1H), 7.36 (d, J=5.2, 1H), 5.25-5.15 (m, 1H), 4.99-4.87 (m, 1H), 3.92-3.80 (m, 3H), 3.67-3.52 (m, 6H), 2.46-2.33 (m, 1H), 2.33-2.20 (m, 1H), 2.09-1.99 (m, 2H), 1.74-1.63 (m, 2H).

5-{2-[1-(Tetrahydrofuran-3-ylmethyl)-1H-pyrazol-4-ylamino]pyrimidin-4-yl}-2-(tetrahydropyran-4-yloxy)benzonitrile ("A41")

With the 1-(tetrahydrofuran-3-ylmethyl)-1H-pyrazol-4-ylamine prepared above, the desired product is obtained in 8% yield; HPLC-MS Rt. [min] 1.986;
HPLC-MS [M+H] 447;
$^1$H NMR (500 MHz, DMSO-$d_6$) δ [ppm] 9.49 (s, 1H), 8.52-8.45 (m, 2H), 8.41 (d, J=8.9, 1H), 7.96 (s, 1H), 7.58 (s, 1H), 7.52 (d, J=9.0, 1H), 7.33 (d, J=5.2, 1H), 4.99-4.88 (m, 1H), 4.11-4.04 (m, 2H), 3.91-3.83 (m, 2H), 3.76 (dd, J=13.8, 7.9, 1H), 3.70-3.60 (m, 2H), 3.60-3.51 (m, 2H), 3.47 (dd, J=8.3, 5.7, 1H), 2.76-2.65 (m, 1H), 2.10-1.98 (m, 2H), 1.97-1.85 (m, 1H), 1.75-1.56 (m, 3H).

5-{4-[3-Cyano-4-(tetrahydropyran-4-yloxy)phenyl]pyrimidin-2-ylamino}benzofuran-2-carboxamide ("A42")

With 5-aminobenzofuran-2-carboxamide, the desired product is obtained in 5% yield; HPLC-MS Rt. [min] 2.036; HPLC-MS [M+H] 456;
$^1$H NMR (500 MHz, DMSO-$d_6$) δ [ppm] 9.75 (s, 1H), 8.55 (dd, J=8.3, 3.7, 2H), 8.46 (dd, J=9.0, 2.3, 1H), 8.28 (d, J=2.1, 1H), 8.03 (s, 1H), 7.72 (dd, J=9.0, 2.2, 1H), 7.62 (s, 1H), 7.56 (dd, J=12.4, 9.1, 2H), 7.51 (d, J=0.6, 1H), 7.47 (d, J=5.3, 1H), 5.00-4.88 (m, 1H), 3.93-3.83 (m, 2H), 3.60-3.51 (m, 2H), 2.10-2.00 (m, 2H), 1.76-1.61 (m, 2H).

5-{2-[1-(2-Pyrazol-1-ylethyl)-1H-pyrazol-4-ylamino]pyrimidin-4-yl}-2-(tetrahydropyran-4-yloxy)benzonitrile ("A43")

With the 1-(2-pyrazol-1-ylethyl)-1H-pyrazol-4-ylamine prepared above, the desired product is obtained in 8% yield; HPLC-MS Rt. [min] 1.954; HPLC-MS [M+H] 457;

$^1$H NMR (500 MHz, DMSO-d$_6$) δ [ppm] 9.47 (s, 1H), 8.49-8.43 (m, 2H), 8.39 (dd, J=9.0, 2.3, 1H), 7.68 (s, 1H), 7.52 (d, J=9.1, 1H), 7.48 (d, J=2.1, 1H), 7.45-7.42 (m, 1H), 7.32 (d, J=5.2, 1H), 6.20-6.13 (m, 1H), 5.00-4.88 (m, 1H), 4.56-4.45 (m, 4H), 3.91-3.83 (m, 2H), 3.61-3.50 (m, 2H), 2.09-1.98 (m, 2H), 1.76-1.59 (m, 2H).

5-{2-[1-(2,2-Difluoroethyl)-1H-pyrazol-4-ylamino]pyrimidin-4-yl}-2-(tetrahydropyran-4-yloxy)benzonitrile ("A44")

With the 1-(2,2-difluoroethyl)-1H-pyrazol-4-ylamine prepared above, the desired product is obtained in 11% yield; HPLC-MS Rt. [min] 2.069;

HPLC-MS [M+H] 427;

$^1$H NMR (500 MHz, DMSO-d$_6$) δ [ppm] 9.56 (s, 1H), 8.53-8.46 (m, 2H), 8.42 (dd, J=9.0, 2.2, 1H), 8.03 (s, 1H), 7.66 (s, 1H), 7.51 (d, J=9.1, 1H), 7.35 (d, J=5.3, 1H), 6.34 (tt, J=55.1, 3.8, 1H), 5.01-4.89 (m, 1H), 4.60 (td, J=15.1, 3.8, 2H), 3.93-3.76 (m, 2H), 3.56 (ddd, J=11.5, 8.4, 3.1, 2H), 2.10-1.91 (m, 2H), 1.77-1.62 (m, 2H).

5-{2-[1-(2-Piperidin-4-ylethyl)-1H-pyrazol-4-ylamino]pyrimidin-4-yl}-2-(tetrahydropyran-4-yloxy)benzonitrile ("A45")

With the tert-butyl 4-[2-(4-aminopyrazol-1-yl)ethyl]piperidine-1-carboxylate prepared above, tert-butyl 4-[2-(4-{4-[3-cyano-4-(tetrahydropyran-4-yloxy)phenyl]-pyrimidin-2-ylamino}pyrazol-1-yl)ethyl]piperidine-1-carboxylate is obtained in 27% yield.

119 mg of tert-butyl 4-[2-(4-{4-[3-cyano-4-(tetrahydropyran-4-yloxy)phenyl]pyrimidin-2-ylamino}pyrazol-1-yl)ethyl]piperidine-1-carboxylate are dissolved in 3 ml of dried dioxane, and 3 ml of HCl in dioxane (4 mol/l) are added. The yellow solution is stirred at room temperature for 60 min.

The reaction mixture is rendered basic using 2 molar NaOH and extracted. The combined organic phases are dried, filtered and evaporated. The crude product is chromatographed, giving 91 mg of the desired compound; HPLC-MS Rt. [min] 1.556; HPLC-MS [M+H] 474;

$^1$H NMR (500 MHz, DMSO-d$_6$) δ [ppm] 9.51 (s, 1H), 8.57-8.45 (m, 3H), 8.41 (dd, J=9.0, 2.2, 1H), 8.21 (d, J=25.7, 1H), 7.95 (s, 1H), 7.58 (s, 1H), 7.52 (d, J=9.2, 1H), 7.35 (d, J=7.5, 1H), 4.99-4.90 (m, 1H), 4.14 (t, J=6.9, 2H), 3.91-3.83 (m, 2H), 3.61-3.51 (m, 2H), 3.23 (d, J=12.7, 2H), 2.81 (q, J=12.4, 2H), 2.09-2.00 (m, 2H), 1.88-1.63 (m, 6H), 1.55-1.42 (m, 1H), 1.39-1.24 (m, 2H).

Synthesis of 5-{2-[1-(3-methoxypropyl)-1H-pyrazol-4-ylamino]pyrimidin-4-yl}-2-(tetrahydropyran-4-yloxy)benzonitrile ("A46")

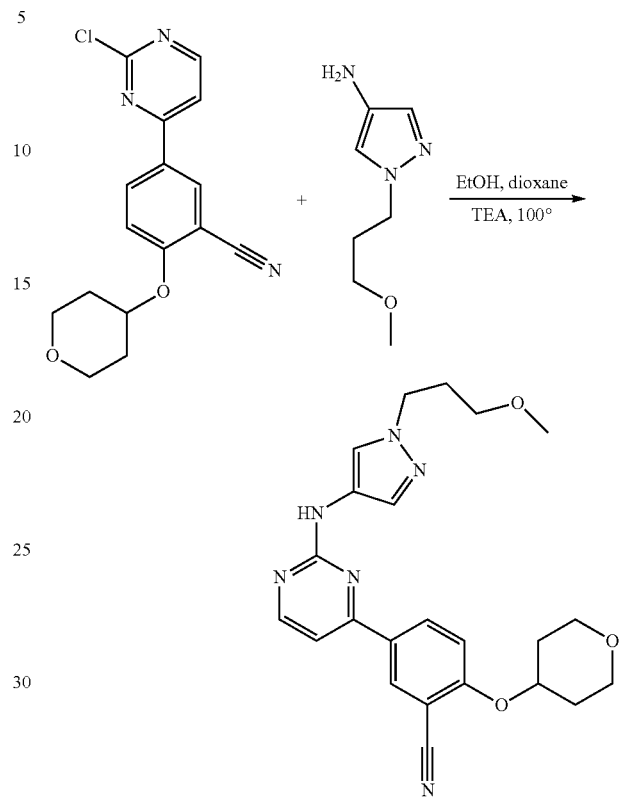

5-(2-Chloropyrimidin-4-yl)-2-(tetrahydropyran-4-yloxy)benzonitrile (200 mg) are dissolved in ethanol and dioxane in a 100 ml three-necked flask, and the 1-(3-methoxypropyl)-1H-pyrazol-4-ylamine (129 mg) prepared above and 0.8 ml of triethylamine are added. The yellow solution is stirred at 100° C. for two days. For work-up, the mixture is evaporated in a rotary evaporator and purified by chromatography, giving 71 mg of the desired product; HPLC-MS Rt. [min] 2.041; HPLC-MS [M+H] 435;

$^1$H NMR (500 MHz, DMSO-d$_6$) δ [ppm] 9.47 (s, 1H), 8.51-8.45 (m, 2H), 8.41 (dd, J=9.0, 2.3, 1H), 7.91 (s, 1H), 7.58 (s, 1H), 7.52 (d, J=9.1, 1H), 7.33 (d, J=5.2, 1H), 4.99-4.88 (m, 1H), 4.12 (t, J=6.9, 2H), 3.94-3.81 (m, 2H), 3.61-3.49 (m, 2H), 3.37-3.24 (m, 2H), 3.24 (s, 3H), 2.10-1.93 (m, 4H), 1.78-1.61 (m, 2H).

Synthesis of 5-{2-[5-(3,6-dihydro-2H-pyran-4-yl)pyridin-2-ylamino]pyridin-4-yl}-2-(tetrahydropyran-4-yloxy)benzonitrile ("A47")

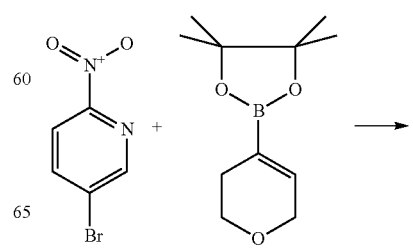

-continued

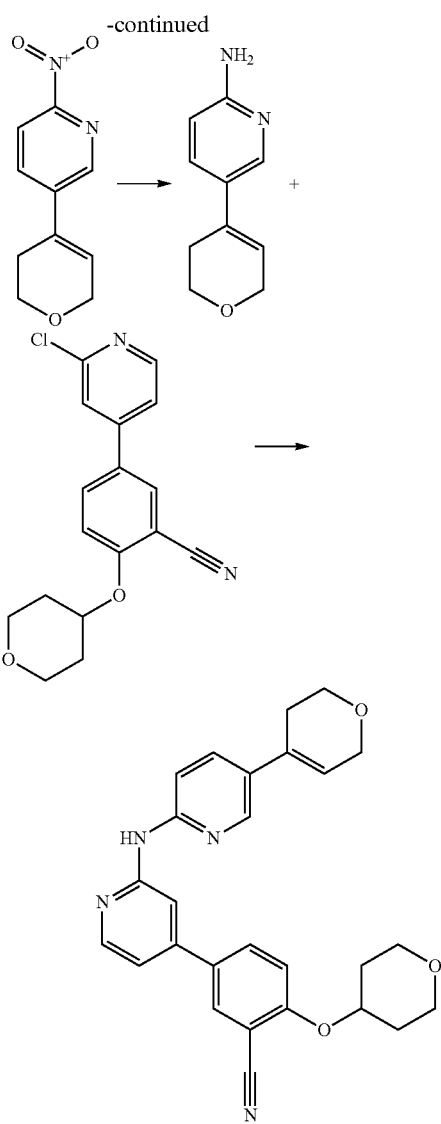

5-Bromo-2-nitropyridine (200 mg; 0.985 mmol) and 4-(4,4,5,5-tetramethyl-1,3,2-dioxaborolan-2-yl)-3,6-dihydro-2H-pyran (227 mg; 1.084 mmol) are dissolved in 3 ml of dioxane and 1 ml of water in a 50 ml three-necked flask under $N_2$, sodium carbonate (208 mg; 1.971 mmol) and bis(triphenylphosphine)palladium(II) chloride (69 mg; 0.099 mmol) are added. The mixture is heated at 80° for 1 hour and stirred at room temperature overnight.

For work-up, the dioxane is evaporated in a rotary evaporator, the residue is diluted with water and extracted with dichloromethane. The combined organic phases are washed with water, dried, filtered and evaporated. The residue is purified over a silica-gel column (petroleum ether/ethyl acetate 1/1), giving 174 mg of 5-(3,6-dihydro-2H-pyran-4-yl)-2-nitropyridine; HPLC-MS Rt. [min] 1.665; HPLC-MS [M+H] 207.

174 mg of 5-(3,6-dihydro-2H-pyran-4-yl)-2-nitropyridine are hydrogenated using 100 mg of 5% Pd/C and hydrogen in 10 ml of tetrahydrofuran. The mixture is filtered off and evaporated in a rotary evaporator, giving 138 mg of 5-(3,6-dihydro-2H-pyran-4-yl)pyridin-2-ylamine crude product, which is reacted further above purification.

With 5-(2-chloropyridin-4-yl)-2-(tetrahydropyran-4-yloxy)benzonitrile and the 5-(3,6-dihydro-2H-pyran-4-yl)pyridin-2-ylamine prepared, 5-{2-[5-(3,6-dihydro-2H-pyran-4-yl)pyridin-2-ylamino]pyridin-4-yl}-2-(tetrahydropyran-4-yloxy)benzonitrile is obtained in 23% yield under the Buchwald-Hartwig conditions indicated; HPLC-MS Rt. [min] 1.717; HPLC-MS [M+H] 455;

$^1$H NMR (500 MHz, DMSO-$d_6$) δ [ppm] 11.19 (s, 1H), 8.38 (dd, J=9.1, 6.2, 2H), 8.24-8.21 (m, 1H), 8.13-8.04 (m, 2H), 7.68 (s, 1H), 7.57 (d, J=9.1, 1H), 7.54-7.45 (m, 2H), 6.37 (s, 1H), 4.99-4.89 (m, 1H), 4.29-4.20 (m, 2H), 3.91-3.81 (m, 5H), 3.61-3.52 (m, 2H), 2.47 (m, 1H), 2.09-2.00 (m, 2H), 1.75-1.64 (m, 2H).

5-[2-(1',2',3',6'-Tetrahydro-[3,4]bipyridinyl-6-ylamino)pyridin-4-yl]-2-(tetrahydropyran-4-yloxy)benzonitrile ("A48")

The same reaction sequence starting from tert-butyl 4-(4,4,5,5-tetramethyl-1,3,2-dioxaborolan-2-yl)-3,6-dihydro-2H-pyridine-1-carboxylate gives tert-butyl 6-{4-[3-cyano-4-(tetrahydropyran-4-yloxy)phenyl]pyridin-2-ylamino}-3',6'-dihydro-2'H[3,4]bipyridinyl-1'-carboxylate.

tert-Butyl 6-{4-[3-cyano-4-(tetrahydropyran-4-yloxy)phenyl]pyridin-2-ylamino}-3',6'-dihydro-2'H-[3,4]bipyridinyl-1'-carboxylate (247 mg; 0.134 mmol) are dissolved in 2 ml of dried dioxane, and 2 ml of HCl in dioxane (4 mol/l) are added. The reaction mixture is stirred at room temperature for 1 h.

For work-up, the reaction mixture is rendered basic using 2 molar NaOH. The solution is then evaporated in a rotary evaporator, and dichloromethane is added. The organic phases are dried, filtered and evaporated. The crude product is purified by chromatography, giving the desired product in 20% yield; HPLC-MS Rt. [min] 1.352; HPLC-MS [M+H] 454;

$^1$H NMR (500 MHz, DMSO-$d_6$) δ [ppm] 10.67 (br, 1H), 8.79 (br, 2H), 8.41 (d, J=2.4, 1H), 8.34 (d, J=5.7, 1H), 8.17 (m, 1H), 8.06-7.96 (m, 2H), 7.84 (s, 1H), 7.64 (d, J=8.7, 1H), 7.58-7.52 (m, 1H), 7.41 (d, J=4.5, 1H), 6.23 (s, 1H), 5.01-4.86 (m, 1H), 3.93-3.83 (m, 3H), 3.79 (s, 2H), 3.61-3.50 (m, 2H), 3.39-3.31 (m, 2H), 2.70 (s, 1H), 2.09-1.97 (m, 2H), 1.74-1.62 (m, 2H).

The following compounds are prepared analogously

| Compound No. | Structure and/or name |
|---|---|
| "A53" | ![structure] |

| Compound No. | Structure and/or name |
|---|---|
| "A58" | 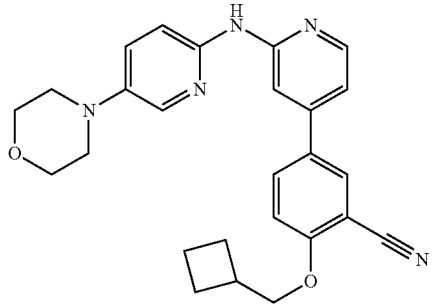 [SMILES: N#Cc1cc(-c2ccnc(Nc3ccc(N4CCOCC4)cn3)c2)ccc1OCC1CCC1] |
| "A59" | 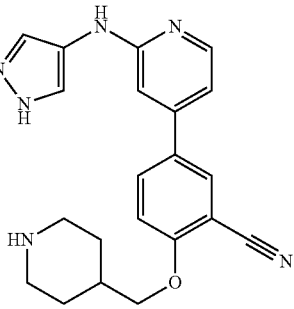 |
| "A60" | 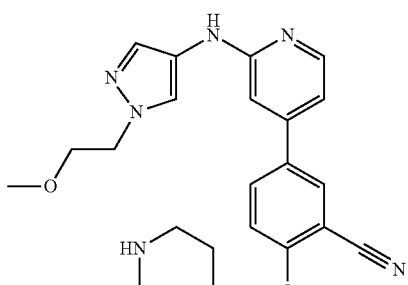 |
| "A61" | 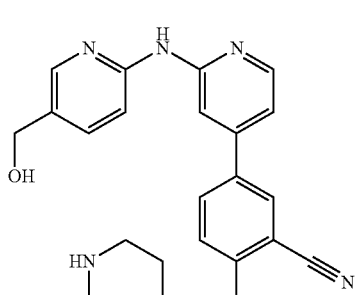 |
| "A62" | 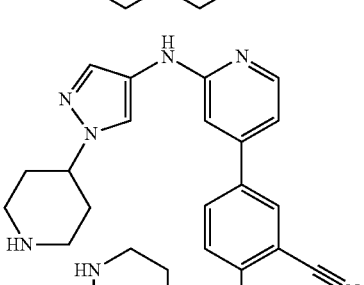 |

| Compound No. | Structure and/or name |
|---|---|
| "A63" | 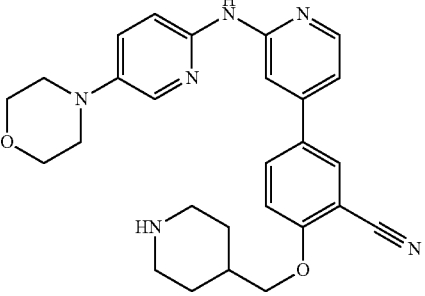 |

Analogously to "A40", tert-butyl 4-(4-aminopyrazol-1-yl)piperidine-1-carboxylate and subsequent removal of the protecting group gives the compound 5-[2-(1-piperidin-4-yl-1H-pyrazol-4-ylamino)pyrimidin-4-yl]-2-(tetrahydropyran-4-yloxy)-benzonitrile ("A64")

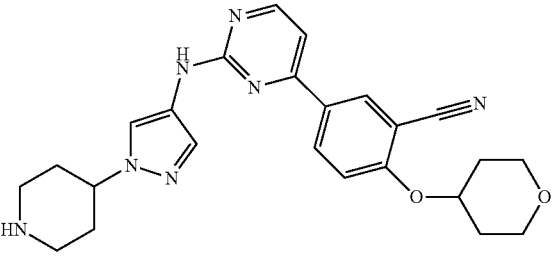 [SMILES: N#Cc1cc(-c2ccnc(Nc3cnn(C4CCNCC4)c3)n2)ccc1OC1CCOCC1]

HPLC-MS Rt. [min] 1.537; HPLC-MS [M+H] 446;
$^1$H NMR (500 MHz, DMSO-d$_6$) δ [ppm] 9.46 (d, J=12.2, 1H), 8.49 (dd, J=7.3, 3.7, 2H), 8.41 (dd, J=9.0, 2.3, 1H), 7.99 (d, J=12.4, 1H), 7.59 (s, 1H), 7.53 (d, J=9.1, 1H), 7.33 (d, J=5.2, 1H), 4.94 (m, 1H), 4.25-4.13 (m, 1H), 3.93-3.82 (m, 2H), 3.56 (m, 6H), 3.09 (d, J=12.5, 2H), 2.71-2.58 (m, 2H), 2.14-1.95 (m, 4H), 1.86-1.60 (m, 4H).

Analogously to "A11", methyl 2-aminoisonicotinate gives the compound 2-{4-[3-cyano-4-(tetrahydropyran-4-yloxy)phenyl]pyridin-2-ylamino}isonicotinic acid ("A65")

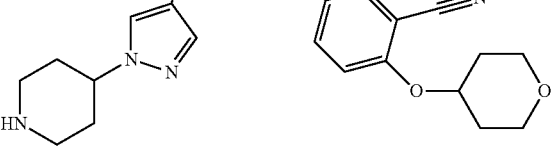

HPLC-MS Rt. [min] 1.682; HPLC-MS [M+H] 431;
$^1$H NMR (500 MHz, DMSO-d$_6$) δ [ppm] 10.00 (s, 1H), 8.42 (d, J=5.2, 1H), 8.36 (s, 1H), 8.32 (t, J=5.3, 1H), 8.11 (d, J=2.4, 1H), 7.99 (dd, J=8.9, 2.4, 1H), 7.95 (d, J=0.7, 1H), 7.52 (d, J=9.0, 1H), 7.29 (ddd, J=18.1, 5.2, 1.5, 2H), 4.91 (tt, J=7.8, 3.8, 1H), 3.94-3.82 (m, 5H), 3.60-3.49 (m, 2H), 2.03 (m, 2H), 1.69 (m, 2H).

Analogously to "A11", tert-butyl 4-(2-aminopyrimidin-5-yl)piperidine-1-carboxylate and subsequent removal of the protecting group gives the compound 5-[2-(5-piperidin-4-ylpyrimidin-2-ylamino)pyridin-4-yl]-2-(tetrahydropyran-4-yloxy)benzonitrile ("A66")

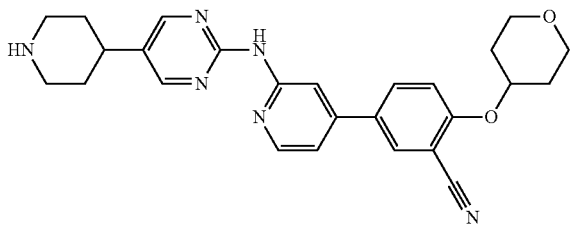 [SMILES: N#Cc1cc(-c2ccnc(Nc3ncc(C4CCNCC4)cn3)c2)ccc1OC1CCOCC1]

HPLC-MS Rt. [min] 1.353; HPLC-MS [M+H] 457.

Analogously to "A26", 5-(2-chloropyrimidin-4-yl)-2-(tetrahydropyran-4-yloxy)benzonitrile and [(1S,2S)-2-(4-aminopyrazol-1-ylmethyl)cyclopropyl]methanol give the compound 5-{2-[1-((1S,2S)-2-hydroxymethylcyclopropylmethyl)-1H-pyrazol-4-ylamino]pyrimidin-4-yl}-2-(tetrahydropyran-4-yloxy)benzonitrile ("A67")

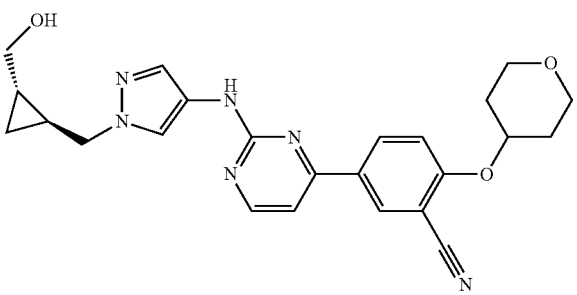 [SMILES: N#Cc1cc(-c2ccnc(Nc3cnn(C[C@H]4C[C@@H]4CO)c3)n2)ccc1OC1CCOCC1]

HPLC-MS Rt. [min] 2.207; HPLC-MS [M+H] 447;
$^1$H NMR (500 MHz, DMSO-d$_6$) δ [ppm] 9.47 (s, 1H), 8.48 (dd, J=10.2, 3.7, 2H), 8.42 (dd, J=8.9, 1.8, 1H), 8.00 (s, 1H), 7.60-7.49 (m, 2H), 7.33 (d, J=5.2, 1H), 4.93 (tt, J=7.9, 3.8, 1H), 4.46 (t, J=5.5, 1H), 4.05 (dd, J=14.0, 6.7, 1H), 3.89 (m, 3H), 3.62-3.47 (m, 2H), 3.37-3.22 (m, 2H), 2.09-1.98 (m, 2H), 1.75-1.61 (m, 2H), 1.16-0.98 (m, 2H), 0.60-0.41 (m, 2H).

Analogously to "A42", 6-amino-2-methyl-2H-pyridazin-3-one gives the compound 5-[2-(1-methyl-6-oxo-1,6-dihydropyridazin-3-ylamino)pyrimidin-4-yl]-2-(tetrahydropyran-4-yloxy)benzonitrile ("A68")

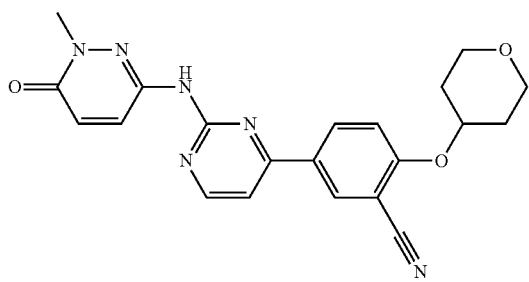 [SMILES: Cn1nc(Nc2nccc(-c3ccc(OC4CCOCC4)c(C#N)c3)n2)ccc1=O]

HPLC-MS Rt. [min] 1.622; HPLC-MS [M+H] 405;
$^1$H NMR (500 MHz, DMSO-d$_6$) δ [ppm] 10.01 (s, 1H), 8.53 (d, J=5.3, 1H), 8.51 (t, J=4.4, 1H), 8.39 (dd, J=9.0, 2.3, 1H), 7.96 (d, J=9.8, 1H), 7.55 (d, J=5.3, 1H), 7.51 (d, J=11.8, 1H), 7.00-6.94 (m, 1H), 4.93 (m, 1H), 3.87 (m, 2H), 3.62 (s, 3H), 3.58-3.50 (m, 2H), 2.10-1.98 (m, 2H), 1.77-1.62 (m, 2H).

Analogously to "A42", 6-amino-2H-pyridazin-3-one gives the compound 5-[2-(6-oxo-1,6-dihydropyridazin-3-ylamino)pyrimidin-4-yl]-2-(tetrahydropyran-4-yloxy)benzonitrile ("A69")

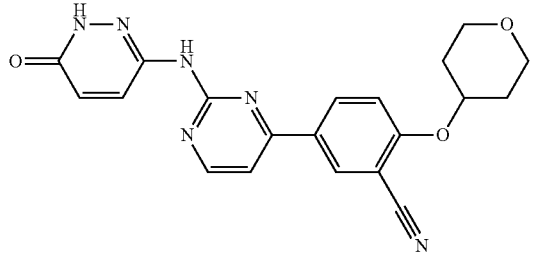 [SMILES: N#Cc1cc(-c2ccnc(Nc3ccc(=O)[nH]n3)n2)ccc1OC1CCOCC1]

HPLC-MS Rt. [min] 2.058; HPLC-MS [M+H] 391;
$^1$H NMR (500 MHz, DMSO-d$_6$) δ [ppm] 12.54 (s, 1H), 9.95 (s, 1H), 8.53 (d, J=5.3, 1H), 8.49 (d, J=2.3, 1H), 8.38 (dd, J=9.0, 2.3, 1H), 7.96 (d, J=10.0, 1H), 7.52 (dd, J=15.9, 6.8, 2H), 6.90 (d, J=10.0, 1H), 5.00-4.85 (m, 1H), 3.87 (m, 2H), 3.60-3.46 (m, 2H), 2.11-1.97 (m, 2H), 1.68 (m, 2H).

Analogously to "A42", (2-aminopyridin-4-yl)methanol gives the compound 5-[2-(4-hydroxymethylpyridin-2-ylamino)pyrimidin-4-yl]-2-(tetrahydropyran-4-yloxy)benzonitrile ("A70")

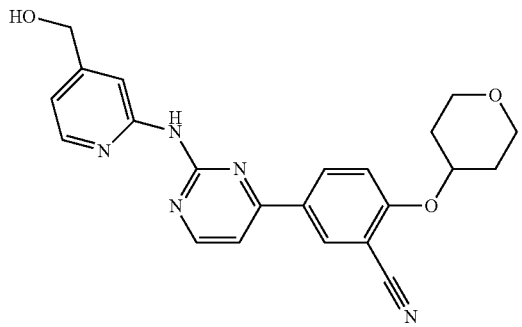 [SMILES: N#Cc1cc(-c2ccnc(Nc3cc(CO)ccn3)n2)ccc1OC1CCOCC1]

HPLC-MS Rt. [min] 1.519; HPLC-MS [M+H] 404.

Analogously to "A11", tert-butyl 4-(6-aminopyridazin-3-yl)piperidine-1-carboxylate and subsequent removal of the protecting group gives the compound 5-[2-(6-piperidin-4-ylpyridazin-3-ylamino)pyridin-4-yl]-2-(tetrahydropyran-4-yloxy)benzonitrile ("A71")

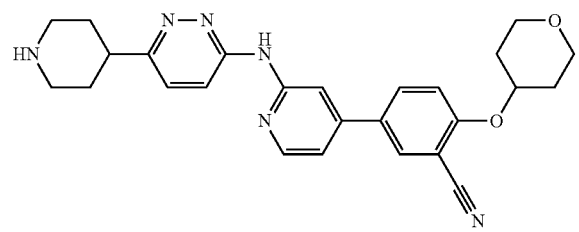 [SMILES: N#Cc1cc(-c2ccnc(Nc3ccc(C4CCNCC4)nn3)c2)ccc1OC1CCOCC1]

HPLC-MS Rt. [min] 1.297; HPLC-MS [M+H] 457;
$^1$H NMR (400 MHz, DMSO-d$_6$) δ [ppm] 10.03 (s, 1H), 8.29 (d, J=5.3, 1H), 8.11 (d, J=2.4, 1H), 8.01 (ddd, J=11.3, 7.7, 3.0, 3H), 7.51 (dd, J=18.7, 9.2, 2H), 7.26 (dd, J=5.3, 1.6, 1H), 4.95-4.85 (m, 1H), 3.93-3.79 (m, 2H), 3.74-3.61 (m, 1H), 3.60-3.44 (m, 3H), 3.07 (m, 2H), 2.93-2.80 (m, 1H), 2.63 (m, 2H), 2.10-1.98 (m, 3H), 1.83-1.55 (m, 3H).

Analogously to "A11", tert-butyl 4-(5-aminopyrazin-2-yl) piperidine-1-carboxylate and subsequent removal of the protecting group gives the compound 5-[2-(5-piperidin-4-ylpyrazin-2-ylamino)pyridin-4-yl]-2-(tetrahydropyran-4-yloxy)benzonitrile ("A72")

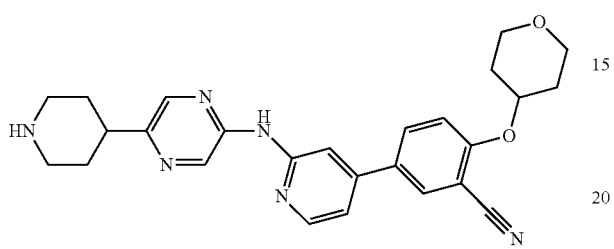

HPLC-MS Rt. [min] 1.297; HPLC-MS [M+H] 457;

$^1$H NMR (400 MHz, DMSO-d$_6$) δ [ppm]$^1$H NMR (400 MHz, DMSO) δ=10.18 (s, 1H), 9.02 (d, J=1.4, 1H), 8.34 (d, J=9.2, 2H), 8.25-8.19 (m, 1H), 8.12 (d, J=2.4, 1H), 8.00 (dd, J=8.9, 2.4, 1H), 7.87 (d, J=1.0, 1H), 7.53 (d, J=9.1, 1H), 7.32 (dd, J=5.5, 1.6, 1H), 4.92 (m, 1H), 3.93-3.83 (m, 2H), 3.62-3.25 (m, 5H), 3.09-2.94 (m, 3H), 2.04 (m, 3H), 1.97-1.82 (m, 2H), 1.69 (m, 2H).

Analogously to "A26", 5-(2-chloropyrimidin-4-yl)-2-(tetrahydropyran-4-yloxy)benzonitrile and cis-4-(4-aminopyrazol-1-yl)cyclohexanol give the compound 5-{2-[1-(4-hydroxycyclohexyl)-1H-pyrazol-4-ylamino]pyrimidin-4-yl}-2-(tetrahydropyran-4-yloxy)benzonitrile ("A73")

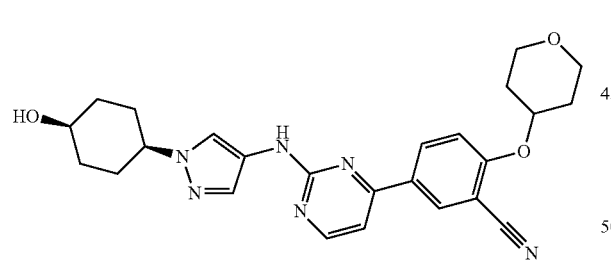

HPLC-MS Rt. [min] 2.294; HPLC-MS [M+H] 461;

$^1$H NMR (500 MHz, DMSO-d$_6$) δ [ppm] 9.48 (s, 1H), 8.49 (m, 2H), 8.40 (dd, J=14.9, 7.4, 1H), 7.94 (s, 1H), 7.58 (s, 1H), 7.52 (d, J=9.1, 1H), 7.33 (d, J=5.2, 1 H), 4.94 (m, 1H), 4.16-4.07 (m, 1H), 3.91-3.79 (m, 4H), 3.56 (m, 2H), 2.20-1.97 (m, 4H), 1.84-1.53 (m, 8H).

Analogously to "A11", tert-butyl 2'-amino-3,4,5,6-tetrahydro-2H-[4,4']bipyridinyl-1-carboxylate and subsequent removal of the protecting group gives the compound 5-[2-(1',2',3',4',5',6'-hexahydro-[4,4']bipyridinyl-2-ylamino)pyridin-4-yl]-2-(tetrahydropyran-4-yloxy)benzonitrile ("A74")

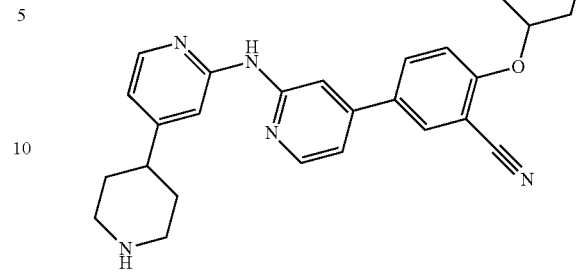

HPLC-MS Rt. [min] 1.351; HPLC-MS [M+H] 456;

$^1$H NMR (500 MHz, DMSO-d$_6$) δ [ppm] 11.44 (s, 1H), 8.74 (d, J=9.9, 1H), 8.51 (d, J=10.1, 1H), 8.39 (d, J=5.8, 1H), 8.32 (d, J=5.8, 1H), 8.22 (d, J=2.3, 1H), 8.06 (dd, J=8.2, 4.1, 1H), 7.71 (d, J=12.3, 1H), 7.61-7.49 (m, 2H), 7.36 (s, 1H), 7.08 (d, J=5.5, 1H), 4.95 (m, 1H), 3.92-3.83 (m, 2H), 3.56 (m, 2H), 3.43 (d, J=12.3, 2H), 3.11-2.95 (m, 3H), 2.10-1.97 (m, 4H), 1.80 (m, 2H), 1.70 (m, 2H).

Analogously to "A26", 5-(2-chloropyrimidin-4-yl)-2-(tetrahydropyran-4-yloxy)benzonitrile and 1-(2-tert-butoxyethyl)-1H-pyrazol-4-ylamine with subsequent removal of the protecting group give the compound 5-{2-[1-(2-hydroxyethyl)-1H-pyrazol-4-ylamino]pyrimidin-4-yl}-2-(tetrahydropyran-4-yloxy)benzonitrile ("A75")

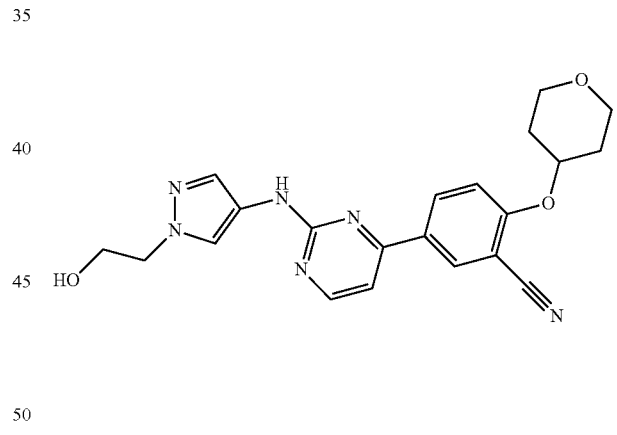

HPLC-MS Rt. [min] 2.105; HPLC-MS [M+H] 407;

$^1$H NMR (500 MHz, DMSO-d$_6$) δ [ppm] 9.57 (s, 1H), 8.53-8.41 (m, 3H), 7.97 (s, 1H), 7.60 (s, 1H), 7.53 (d, J=9.1, 1H), 7.36 (d, J=5.3, 1H), 4.94 (tt, J=7.9, 3.8, 1H), 4.2 (m, 1H), 3.92-3.81 (m, 3H), 3.72 (m, 2H), 3.61-3.51 (m, 2H), 2.05 (m, 2H), 1.77-1.60 (m, 2H).

Analogously to "A42", 5-[2-(5-bromo-6-methoxypyridin-2-ylamino)pyrimidin-4-yl]-2-(tetrahydropyran-4-yloxy) benzonitrile and tert-butyl 4-(4,4,5,5-tetramethyl-1,3,2-dioxaborolan-2-yl)-3,6-dihydro-2H-pyridine-1-carboxylate and subsequent removal of the protecting group gives the compound 5-[2-(2-methoxy-1',2',3',6'-tetrahydro[3,4']bipyridinyl-6-ylamino)pyrimidin-4-yl]-2-(tetrahydropyran-4-yloxy) benzonitrile ("A76")

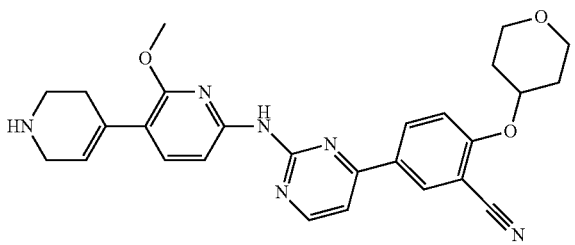 [SMILES: COc1nc(Nc2nccc(-c3ccc(OC4CCOCC4)c(C#N)c3)n2)ccc1C1=CCNCC1]

HPLC-MS Rt. [min] 2.018; HPLC-MS [M+H] 485;
$^1$H NMR (500 MHz, DMSO-d$_6$) δ [ppm] 9.53 (s, 1H), 8.65-8.56 (m, 2H), 8.48 (dd, J=9.0, 2.3, 1H), 7.86-7.79 (m, 1H), 7.58-7.49 (m, 3H), 6.04-5.95 (m, 1H), 5.00-4.88 (m, 1H), 3.93-3.83 (m, 5H), 3.60-3.51 (m, 2H), 3.41-3.36 (m, 2H), 2.92 (t, J=5.6, 2H), 2.37-2.28 (m, 2H), 2.10-1.99 (m, 2H), 1.76-1.63 (m, 2H).

Analogously to "A11", tert-butyl(2-aminopyridin-4-ylmethyl)carbamate and subsequent removal of the protecting group gives the compound 5-[2-(4-aminomethyl-pyridin-2-ylamino)pyridin-4-yl]-2-(tetrahydropyran-4-yloxy)benzonitrile ("A77")

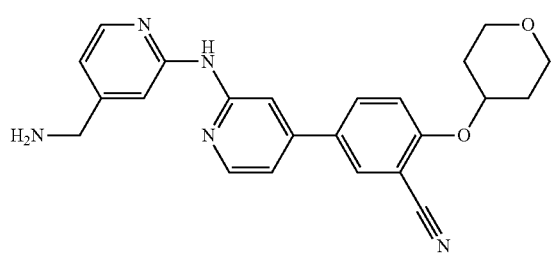 [SMILES: N#Cc1cc(-c2ccnc(Nc3cc(CN)ccn3)c2)ccc1OC1CCOCC1]

HPLC-MS Rt. [min] 1.251; HPLC-MS [M+H] 402;
$^1$H NMR (500 MHz, DMSO-d$_6$) δ [ppm] 11.12 (s, 1H), 8.49-8.31 (m, 5H), 8.21 (d, J=5.1, 1H), 8.05 (dd, J=9.2, 4.6, 1H), 7.79 (d, J=0.9, 1H), 7.57 (d, J=9.0, 2H), 7.48 (dd, J=18.9, 5.3, 1H), 7.17 (d, J=5.2, 1H), 4.95 (tt, J=7.7, 3.8, 1H), 4.15 (d, J=4.7, 2H), 3.91-3.83 (m, 2H), 3.60-3.51 (m, 2H), 2.09-1.99 (m, 2H), 1.75-1.62 (m, 2H).

"A74" with formaldehyde and formic acid gives the compound 5-[2-(1'-methyl-1',2',3',4',5',6'-hexahydro-[4,4']bipyridinyl-2-ylamino)pyridin-4-yl]-2-(tetrahydropyran-4-yloxy)benzonitrile ("A78")

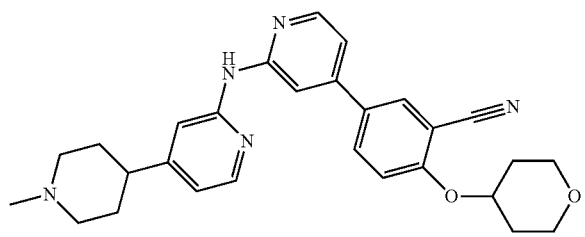 [SMILES: CN1CCC(c2ccnc(Nc3cc(-c4ccc(OC5CCOCC5)c(C#N)c4)ccn3)c2)CC1]

HPLC-MS Rt. [min] 1.338; HPLC-MS [M+H] 470;
$^1$H NMR (500 MHz, DMSO-d$_6$) δ [ppm] 9.58 (s, 1H), 8.28 (d, J=5.3, 1H), 8.13 (d, J=5.2, 1H), 8.08 (d, J=2.3, 1H), 8.03 (s, 1H), 7.96 (dd, J=8.9, 2.4, 1H), 7.63 (s, 1H), 7.50 (d, J=13.0, 1H), 7.19 (dd, J=5.3, 1.5, 1H), 6.79 (dd, J=5.2, 1.1, 1H), 4.97-4.86 (m, 1H), 3.94-3.82 (m, 2H), 3.61-3.47 (m, 2H), 2.95-2.83 (m, 2H), 2.47-2.36 (m, 2H), 2.21 (s, 3H), 2.09-1.94 (m, 4H), 1.81-1.53 (m, 6H).

Analogously to "A26", 1-(2-tert-butoxyethyl)-1H-pyrazol-4-ylamine and subsequent removal of the protecting group gives the compound 5-{2-[1-(2-hydroxyethyl)-1H-pyrazol-4-ylamino]pyridin-4-yl}-2-(tetrahydropyran-4-yloxy)benzonitrile ("A79")

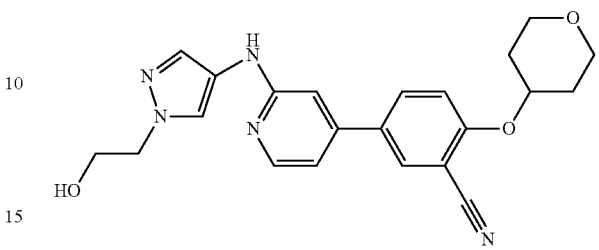

HPLC-MS Rt. [min] 1.626; HPLC-MS [M+H] 406;
$^1$H NMR (500 MHz, DMSO-d$_6$) δ [ppm] 9.40 (s, 1H), 8.15 (d, J=17.7, 1H), 8.07 (d, J=6.0, 1H), 8.02-7.95 (m, 2H), 7.57-7.46 (m, 2H), 7.10 (d, J=31.6, 2H), 4.98-4.86 (m, 1H), 4.14 (t, J=5.6, 3H), 3.92-3.81 (m, 2H), 3.75 (t, J=5.7, 2H), 3.59-3.51 (m, 2H), 2.08-1.98 (m, 2H), 1.73-1.60 (m, 2H).

Analogously to "A42", 5-methylisoxazol-3-ylamine gives the compound 5-[2-(5-methylisoxazol-3-ylamino)pyrimidin-4-yl]-2-(tetrahydropyran-4-yloxy)benzonitrile ("A80")

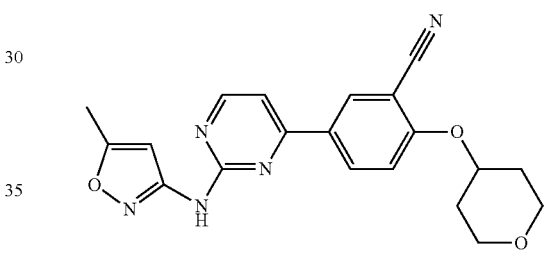

HPLC-MS Rt. [min] 1.818; HPLC-MS [M+H] 378;
$^1$H NMR (400 MHz, DMSO-d$_6$) δ [ppm] 10.32 (s, 1H), 8.57 (d, J=5.3, 1H), 8.53 (d, J=2.3, 1H), 8.45 (dd, J=9.0, 2.3, 1H), 7.63-7.47 (m, 2H), 6.77 (s, 1H), 5.04-4.88 (m, 1H), 3.94-3.79 (m, 2H), 3.62-3.46 (m, 2H), 2.40 (s, 3H), 2.09-1.92 (m, 2H), 1.77-1.59 (m, 2H).

"A77" with formaldehyde and formic acid gives the compound 5-[2-(4-dimethyl-aminomethylpyridin-2-ylamino)pyridin-4-yl]-2-(tetrahydropyran-4-yloxy)benzonitrile ("A81")

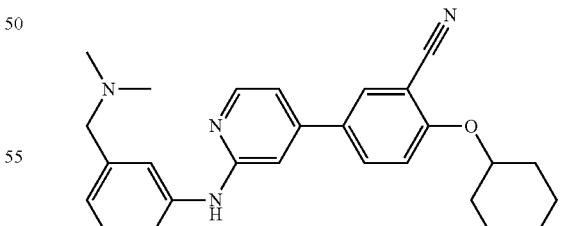

HPLC-MS Rt. [min] 1.272; HPLC-MS [M+H] 430;
$^1$H NMR (400 MHz, DMSO-d$_6$) δ [ppm] 9.61 (s, 1H), 8.28 (d, J=5.3, 1H), 8.16 (d, J=5.1, 1H), 8.09 (d, J=2.4, 1H), 8.03 (d, J=0.9, 1H), 7.97 (dd, J=8.9, 2.4, 1H), 7.67 (s, 1H), 7.52 (d, J=9.1, 1H), 7.20 (dd, J=5.3, 1.6, 1H), 6.83 (dd, J=5.1, 1.1, 1H), 4.96-4.85 (m, 1H), 3.94-3.81 (m, 2H), 3.61-3.47 (m, 2H), 3.37 (s, 2H), 2.16 (s, 6H), 2.08-1.96 (m, 2H), 1.76-1.61 (m, 2H).

Analogously to "A11", 4-morpholin-4-ylpyridin-2-ylamine gives the compound 5-[2-(4-morpholin-4-ylpyridin-2-ylamino)pyridin-4-yl]-2-(tetrahydropyran-4-yloxy)benzonitrile ("A82")

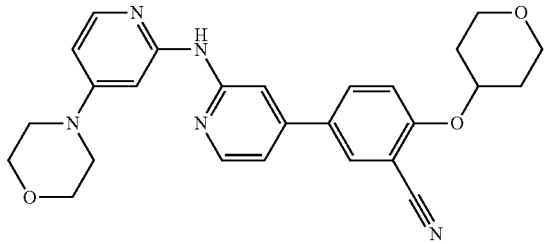 [SMILES: N#Cc1cc(-c2ccnc(Nc3cc(N4CCOCC4)ccn3)c2)ccc1OC1CCOCC1]

HPLC-MS Rt. [min] 1.690; HPLC-MS [M+H] 458.

Analogously to "A42", 1-(2-pyrrolidin-1-ylethyl)-1H-pyrazol-4-ylamine gives the compound 5-{2-[1-(2-pyrrolidin-1-ylethyl)-1H-pyrazol-4-ylamino]pyrimidin-4-yl}-2-(tetrahydropyran-4-yloxy)benzonitrile ("A83")

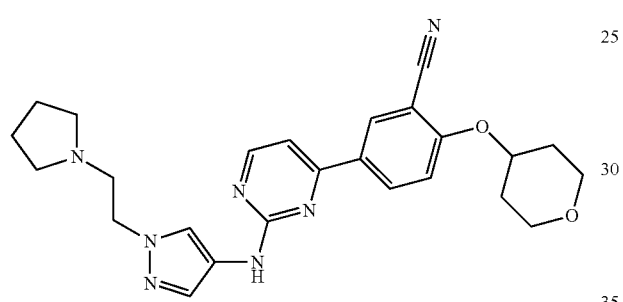

HPLC-MS Rt. [min] 1.795; HPLC-MS [M+H] 460;
$^1$H NMR (500 MHz, DMSO-$d_6$) δ [ppm] 9.65 (s, 1H), 9.54 (s, 1H), 8.54-8.47 (m, 2H), 8.42 (dd, J=9.0, 2.1, 1H), 8.07 (s, 1H), 7.70 (s, 1H), 7.52 (d, J=9.1, 1H), 7.36 (t, J=10.5, 1H), 4.99-4.89 (m, 1H), 4.49 (t, J=6.0, 2H), 3.91-3.81 (m, 2H), 3.71-3.61 (m, 2H), 3.60-3.45 (m, 4H), 3.10-2.94 (m, 2H), 2.10-1.94 (m, 4H), 1.91-1.76 (m, 2H), 1.75-1.62 (m, 2H).

Analogously to "A11", 4-(4-methylpiperazin-1-yl)pyridin-2-ylamine gives the compound 5-{2-[4-(4-methylpiperazin-1-yl)pyridin-2-ylamino]pyridin-4-yl}-2-(tetrahydropyran-4-yloxy)benzonitrile ("A84")

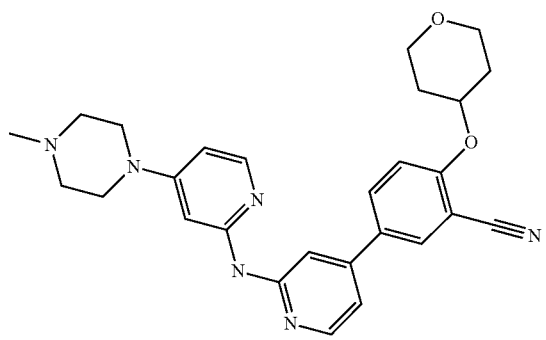 [SMILES: CN1CCN(c2ccnc(Nc3cc(-c4ccc(OC5CCOCC5)c(C#N)c4)ccn3)c2)CC1]

HPLC-MS Rt. [min] 1.344; HPLC-MS [M+H] 471;
$^1$H NMR (500 MHz, DMSO-$d_6$) δ [ppm] 11.52 (s, 1H), 10.41 (s, 1H), 8.39 (d, J=5.5, 1H), 8.19 (d, J=2.4, 1H), 8.09-7.99 (m, 2H), 7.56 (d, J=9.1, 1H), 7.52 (d, J=4.9, 1 H), 7.38 (s, 1H), 6.96 (d, J=5.6, 1H), 6.71 (s, 1H), 4.98-4.89 (m, 1H), 4.2 (m, 2H), 3.92-3.82 (m, 2H), 3.59-3.49 (m, 4H), 3.2 (m, 4H), 2.85 (s, 3H), 2.09-1.96 (m, 2H), 1.75-1.61 (m, 2H).

Analogously to "A11", 6-morpholin-4-ylpyrazin-2-ylamine gives the compound 5-[2-(6-morpholin-4-ylpyrazin-2-ylamino)pyridin-4-yl]-2-(tetrahydropyran-4-yloxy)benzonitrile ("A85")

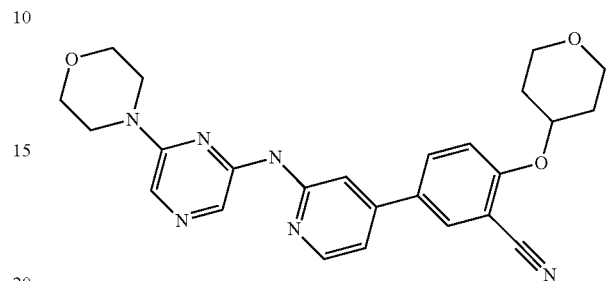

HPLC-MS Rt. [min] 1.767; HPLC-MS [M+H] 459.

Analogously to "A11", 4-(5,6-dihydro-4H-pyran-2-yl)pyridin-2-ylamine gives the compound 5-{2-[4-(5,6-dihydro-4H-pyran-2-yl)pyridin-2-ylamino]pyridin-4-yl}-2-(tetrahydropyran-4-yloxy)benzonitrile ("A86")

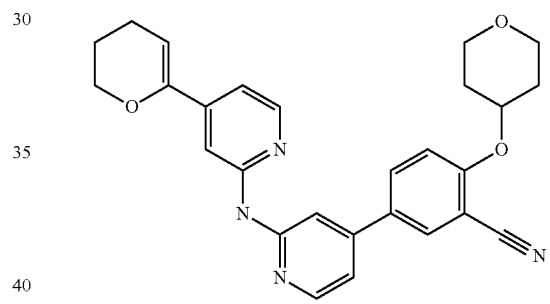

HPLC-MS Rt. [min] 1.860; HPLC-MS [M+H] 455.

Analogously to "A42", 4-cyclopropylthiazol-2-ylamine gives the compound 5-[2-(4-cyclopropylthiazol-2-ylamino)pyrimidin-4-yl]-2-(tetrahydropyran-4-yloxy)benzonitrile ("A87")

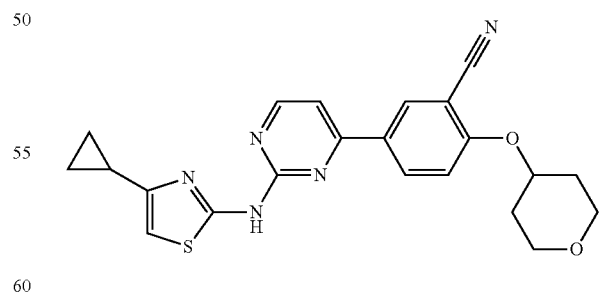

HPLC-MS Rt. [min] 2.839; HPLC-MS [M+H] 420.

Analogously to "A11", 5-(2-oxa-6-azaspiro[3.3]hept-6-ylmethyl)pyridin-2-ylamine gives the compound 5-{2-[5-(2-oxa-6-azaspiro[3.3]hept-6-ylmethyl)pyridin-2-yl-amino]pyridin-4-yl}-2-(tetrahydropyran-4-yloxy)benzonitrile ("A88")

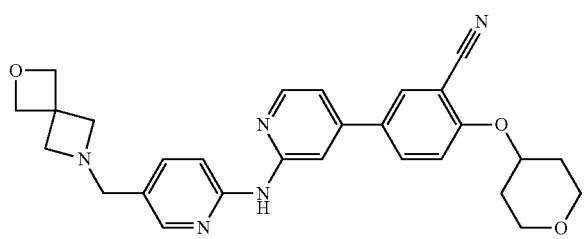 [SMILES: N#Cc1cc(-c2ccnc(Nc3ccc(CN4CC5(COC5)C4)cn3)c2)ccc1OC1CCOCC1]

HPLC-MS Rt. [min] 1.463; HPLC-MS [M+H] 484;
$^1$H NMR (500 MHz, DMSO-d$_6$) δ [ppm] 10.24 (s, 1H), 9.86 (s, 1H), 8.32 (d, J=5.4, 2H), 8.13 (d, J=2.2, 1H), 8.00 (dd, J=8.9, 2.4, 1H), 7.92 (s, 1H), 7.81-7.73 (m, 2H), 7.54 (d, J=9.1, 1H), 7.33 (d, J=4.9, 1H), 4.98-4.88 (m, 1H), 4.68 (s, 2H), 4.63 (s, 2H), 4.36-4.18 (m, 4H), 3.92-3.82 (m, 4H), 3.61-3.51 (m, 2H), 2.08-1.97 (m, 2H), 1.74-1.62 (m, 2H).

Analogously to "A11", tert-butyl 4-(2-aminopyrimidin-4-yl)piperidine-1-carboxylate with subsequent removal of the protecting group gives the compound 5-[2-(4-piperidin-4-ylpyrimidin-2-ylamino)pyridin-4-yl]-2-(tetrahydropyran-4-yloxy)benzonitrile ("A89")

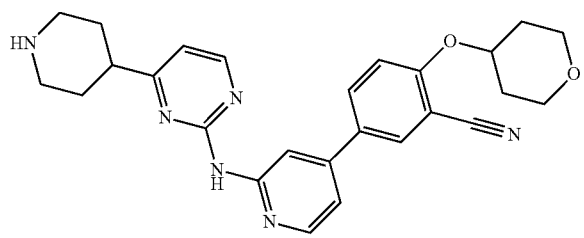 [SMILES: N#Cc1cc(-c2ccnc(Nc3nccc(C4CCNCC4)n3)c2)ccc1OC1CCOCC1]

HPLC-MS Rt. [min] 1.287; HPLC-MS [M+H] 457;
$^1$H NMR (500 MHz, DMSO-d$_6$) δ [ppm] 10.46 (s, 1H), 8.66 (d, J=9.9, 1H), 8.58 (d, J=5.1, 1H), 8.42-8.30 (m, 3H), 8.20 (d, J=2.4, 1H), 8.07 (dd, J=8.9, 2.4, 1H), 7.56 (d, J=9.1, 1H), 7.50-7.44 (m, 1H), 7.03 (d, J=5.1, 1H), 4.99-4.90 (m, 1H), 3.93-3.83 (m, 2H), 3.61-3.52 (m, 2H), 3.43 (d, J=12.6, 2H), 3.12-2.99 (m, 3H), 2.16 (d, J=13.0, 2H), 2.10-1.99 (m, 2H), 1.98-1.82 (m, 2H), 1.75-1.64 (m, 2H).

Analogously to "A11", 6-morpholin-4-ylpyridazin-3-ylamine gives the compound 5-[2-(6-morpholin-4-ylpyridazin-3-ylamino)pyridin-4-yl]-2-(tetrahydropyran-4-yloxy)benzonitrile ("A90")

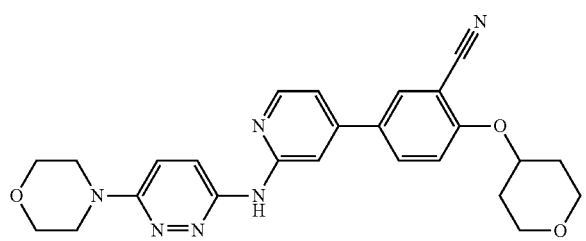 [SMILES: N#Cc1cc(-c2ccnc(Nc3ccc(N4CCOCC4)nn3)c2)ccc1OC1CCOCC1]

HPLC-MS Rt. [min] 1.529; HPLC-MS [M+H] 459;
$^1$H NMR (500 MHz, DMSO-d$_6$) δ [ppm] 9.69 (s, 1H), 8.24 (d, J=5.3, 1H), 8.08 (d, J=2.4, 1H), 7.98-7.93 (m, 2H), 7.86 (d, J=9.8, 1H), 7.52 (d, J=9.1, 1H), 7.34 (t, J=8.6, 1H), 7.19 (dd, J=5.3, 1.6, 1H), 4.95-4.85 (m, 1H), 3.91-3.80 (m, 2H), 3.73 (dd, J=16.7, 11.7, 4H), 3.60-3.49 (m, 2H), 3.47-3.38 (m, 4H), 2.08-1.97 (m, 2H), 1.75-1.64 (m, 2H).

Analogously to "A11", tert-butyl 6-amino-3',4',5',6'-tetrahydro-2'H-[2,4']bipyridinyl-1'-carboxylate and subsequent removal of the protecting group gives the compound 5-[2-(1',2',3',4',5',6'-hexahydro-[2,4']bipyridinyl-6-ylamino)pyridin-4-yl]-2-(tetrahydropyran-4-yloxy)benzonitrile ("A91")

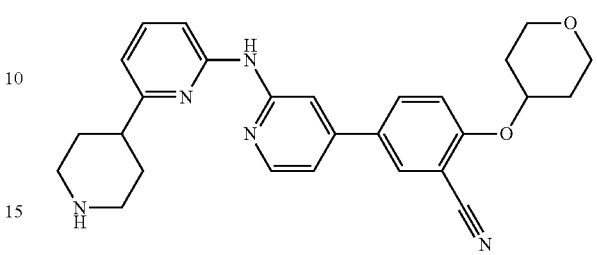

HPLC-MS Rt. [min] 1.291; HPLC-MS [M+H] 456;
$^1$H NMR (500 MHz, DMSO-d$_6$) δ [ppm] 9.63 (s, 1H), 8.51 (s, 1H), 8.27 (d, J=4.2, 1 H), 8.12-8.01 (m, 2H), 7.61-7.54 (m, 1H), 7.49 (d, J=6.7, 1H), 7.30 (d, J=8.2, 1 H), 7.21 (d, J=6.0, 1H), 6.75 (t, J=7.5, 1H), 4.97-4.88 (m, 1H), 3.92-3.82 (m, 2H), 3.62-3.53 (m, 3H), 3.06 (d, J=11.9, 2H), 2.72-2.56 (m, 3H), 2.08-2.00 (m, 2H), 1.87-1.77 (m, 2H), 1.74-1.58 (m, 4H).

Analogously to "A11", 6-(5,6-dihydro-4H-pyran-2-yl)pyrazin-2-ylamine gives the compound 5-{2-[6-(5,6-dihydro-4H-pyran-2-yl)pyrazin-2-ylamino]pyridin-4-yl}-2-(tetrahydropyran-4-yloxy)benzonitrile ("A92")

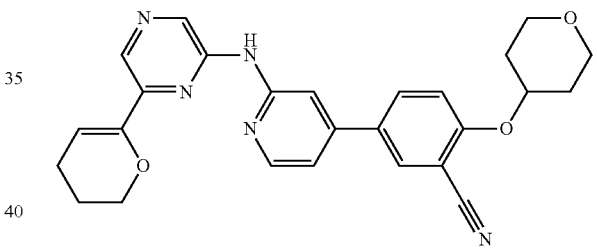

HPLC-MS Rt. [min] 2.266; HPLC-MS [M+H] 456;
$^1$H NMR (500 MHz, DMSO-d$_6$) δ [ppm] 10.16 (s, 1H), 8.72 (s, 1H), 8.40 (s, 1H), 8.35 (d, J=5.3, 1H), 8.21-8.17 (m, 1H), 8.11 (d, J=2.4, 1H), 8.03 (dd, J=8.9, 2.4, 1 H), 7.63-7.59 (m, 1H), 7.59-7.51 (m, 2H), 7.33 (dd, J=5.3, 1.6, 1H), 6.06-6.00 (m, 1H), 4.97-4.89 (m, 1H), 4.21-4.15 (m, 2H), 3.91-3.83 (m, 2H), 3.60-3.52 (m, 2H), 2.34-2.24 (m, 2H), 2.08-1.98 (m, 2H), 1.93-1.84 (m, 2H), 1.76-1.64 (m, 2H).

Analogously to "A40", 4-methyloxazol-2-ylamine gives the compound 5-[2-(4-methyloxazol-2-ylamino)pyrimidin-4-yl]-2-(tetrahydropyran-4-yloxy)benzonitrile ("A93")

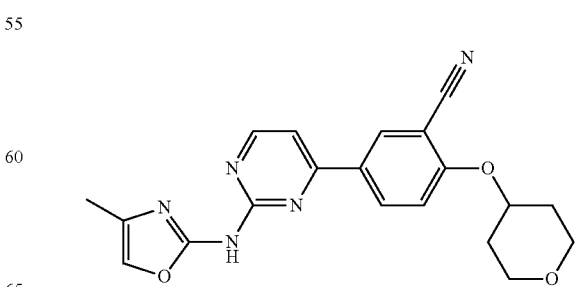

HPLC-MS Rt. [min] 2.066; HPLC-MS [M+H] 378;

¹H NMR (500 MHz, DMSO-d₆) δ [ppm] 10.64 (s, 1H), 8.57 (dd, J=13.8, 3.8, 2H), 8.45 (dd, J=9.0, 2.3, 1H), 7.62 (d, J=5.3, 1H), 7.53 (d, J=9.1, 2H), 4.99-4.89 (m, 1H), 3.91-3.83 (m, 2H), 3.60-3.51 (m, 2H), 2.10-1.99 (m, 5H), 1.73-1.63 (m, 2H).

Analogously to "A26", 5-(2-chloropyrimidin-4-yl)-2-cyclobutylmethoxybenzonitrile and 1-(2-tert-butoxyethyl)-1H-pyrazol-4-ylamine with subsequent removal of the protecting group give the compound 2-cyclobutylmethoxy-5-{2-[1-(2-hydroxyethyl)-1H-pyrazol-4-ylamino]pyrimidin-4-yl}benzonitrile ("A94")

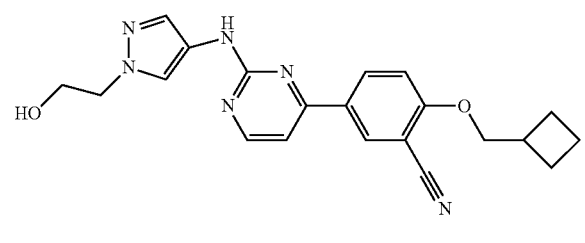 [SMILES: N#Cc1cc(-c2ccnc(Nc3cnn(CCO)c3)n2)ccc1OCC1CCC1]

HPLC-MS Rt. [min] 2.573; HPLC-MS [M+H] 391;

¹H NMR (500 MHz, DMSO-d₆) δ [ppm] 9.49 (s, 1H), 8.52-8.43 (m, 3H), 7.97 (s, 1H), 7.58 (s, 1H), 7.43 (d, J=9.0, 1H), 7.34 (d, J=5.2, 1H), 4.88 (t, J=4.9, 1H), 4.23 (d, J=6.4, 2H), 4.13 (t, J=5.5, 2H), 3.75 (q, J=5.4, 2H), 2.87-2.74 (m, 1H), 2.18-2.07 (m, 2H), 2.01-1.85 (m, 4H).

Analogously to "A26", 5-(2-chloropyrimidin-4-yl)-2-cyclobutylmethoxybenzonitrile and [(1S,2S)-2-(4-aminopyrazol-1-ylmethyl)cyclopropyl]methanol give the compound 2-cyclobutylmethoxy-5-{2-[1-((1S,2S)-2-hydroxymethylcyclopropylmethyl)-1H-pyrazol-4-ylamino]pyrimidin-4-yl}benzonitrile ("A95")

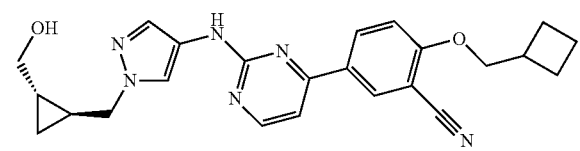 [SMILES: N#Cc1cc(-c2ccnc(Nc3cnn(C[C@H]4C[C@@H]4CO)c3)n2)ccc1OCC1CCC1]

HPLC-MS Rt. [min] 2.677; HPLC-MS [M+H] 431;

¹H NMR (500 MHz, DMSO-d₆) δ [ppm] 9.49 (s, 1H), 8.52-8.41 (m, 3H), 8.02 (s, 1H), 7.56 (s, 1H), 7.43 (d, J=9.0, 1H), 7.34 (d, J=5.2, 1H), 4.47 (t, J=5.5, 1H), 4.23 (d, J=6.4, 2H), 4.06 (dd, J=14.0, 6.7, 1H), 3.93 (dd, J=14.0, 7.4, 1H), 3.3 (m, 2H), 2.88-2.73 (m, 1H), 2.17-2.02 (m, 2H), 2.02-1.84 (m, 4H), 1.19-0.96 (m, 2H), 0.57-0.41 (m, 2H).

Analogously to "A11", tert-butyl 4-(6-aminopyrazin-2-yl)piperidine-1-carboxylate and subsequent removal of the protecting group gives the compound 5-[2-(6-piperidin-4-ylpyrazin-2-ylamino)pyridin-4-yl]-2-(tetrahydropyran-4-yloxy)benzonitrile ("A96")

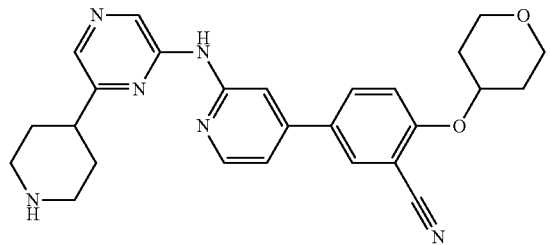

HPLC-MS Rt. [min] 1.368; HPLC-MS [M+H] 457.

Analogously to "A26", 5-(2-chloropyrimidin-4-yl)-2-cyclobutylmethoxybenzonitrile and 4-(4-aminopyrazol-1-yl)cyclohexanol give the compound 2-cyclobutylmethoxy-5-{2-[1-(4-hydroxycyclohexyl)-1H-pyrazol-4-ylamino]pyrimidin-4-yl}benzonitrile ("A97")

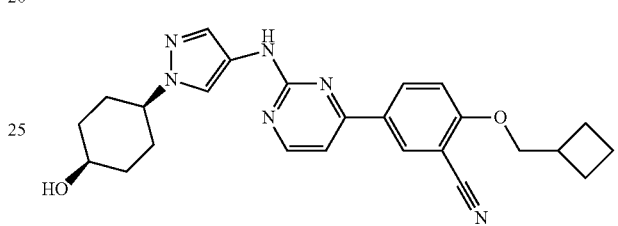

HPLC-MS Rt. [min] 2.765; HPLC-MS [M+H] 445;

¹H NMR (500 MHz, DMSO-d₆) δ [ppm] 9.46 (s, 1H), 8.48 (d, J=2.3, 2H), 8.43 (dd, J=8.9, 2.3, 1H), 7.95 (s, 1H), 7.57 (s, 1H), 7.42 (d, J=9.0, 1H), 7.33 (d, J=5.2, 1H), 4.43 (d, J=3.4, 1H), 4.22 (d, J=6.4, 2H), 4.16-4.06 (m, 1H), 3.86-3.80 (m, 1H), 2.85-2.74 (m, 1H), 2.18-2.05 (m, 4H), 2.00-1.85 (m, 4H), 1.84-1.68 (m, 4H), 1.65-1.54 (m, 2H).

Analogously to "A11", 5-(tetrahydropyran-4-yl)pyrazin-2-ylamine gives the compound 2-(tetrahydropyran-4-yloxy)-5-{2-[5-(tetrahydropyran-4-yl)pyrazin-2-yl-amino]pyridin-4-yl}benzonitrile ("A98")

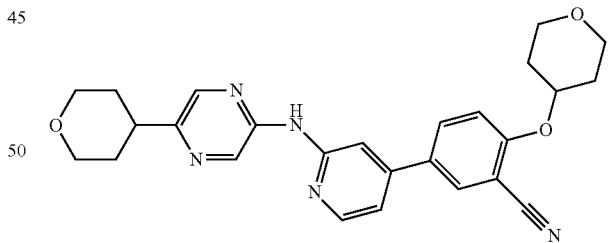

HPLC-MS Rt. [min] 1.646; HPLC-MS [M+H] 458;

¹H NMR (500 MHz, DMSO-d₆) δ [ppm] 10.06 (s, 1H), 8.75 (s, 1H), 8.37-8.31 (m, 2H), 8.25 (s, 1H), 8.13 (t, J=5.4, 1H), 8.07-7.99 (m, 2H), 7.53 (d, J=8.9, 1H), 7.32 (dd, J=5.3, 1.6, 1H), 4.97-4.85 (m, 1H), 3.94-3.84 (m, 2H), 3.61-3.53 (m, 2H), 3.32-3.25 (m, 2H), 3.01-2.81 (m, 3H), 2.10-1.96 (m, 4H), 1.86 (qd, J=12.9, 3.8, 2H), 1.76-1.60 (m, 2H).

Analogously to "A11", (5-aminopyrazin-2-yl)methanol gives the compound 5-[2-(5-hydroxymethylpyrazin-2-ylamino)pyridin-4-yl]-2-(tetrahydropyran-4-yloxy)benzonitrile ("A99")

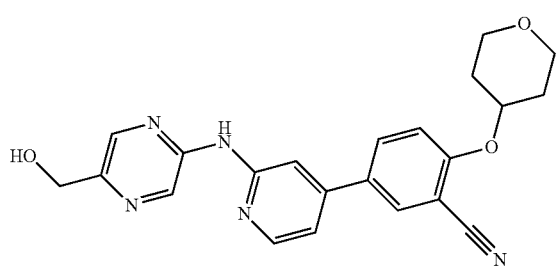 [SMILES: N#Cc1cc(-c2ccnc(Nc3cnc(CO)cn3)c2)ccc1OC1CCOCC1]

HPLC-MS Rt. [min] 1.457; HPLC-MS [M+H] 404;

¹H NMR (500 MHz, DMSO-d₆) δ [ppm] 10.00 (s, 1H), 9.05 (d, J=1.3, 1H), 8.33 (d, J=5.3, 1H), 8.30 (s, 1H), 8.12 (d, J=4.1, 1H), 7.99 (dd, J=8.9, 2.4, 1H), 7.90 (d, J=0.9, 1H), 7.53 (d, J=9.0, 1H), 7.29 (dd, J=5.3, 1.6, 1H), 5.35 (t, J=5.8, 1H), 4.97-4.87 (m, 1H), 4.55 (d, J=5.6, 2H), 3.92-3.82 (m, 2H), 3.61-3.52 (m, 2H), 2.09-1.98 (m, 2H), 1.75-1.61 (m, 2H).

Analogously to "A11", 6-(tetrahydropyran-4-yl)pyridazin-3-ylamine gives the compound 2-(tetrahydropyran-4-yloxy)-5-{2-[6-(tetrahydropyran-4-yl)pyridazin-3-ylamino]pyridin-4-yl}benzonitrile ("A100")

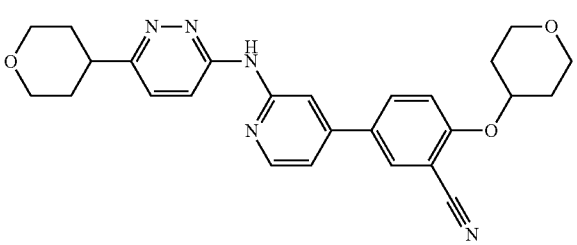 [SMILES: N#Cc1cc(-c2ccnc(Nc3ccc(C4CCOCC4)nn3)c2)ccc1OC1CCOCC1]

HPLC-MS Rt. [min] 1.643; HPLC-MS [M+H] 458;

¹H NMR (500 MHz, DMSO-d₆) δ [ppm] 10.04 (s, 1H), 8.29 (d, J=5.3, 1H), 8.11 (d, J=2.4, 1H), 8.05-8.02 (m, 1H), 8.01-7.97 (m, 2H), 4.95-4.85 (m, 1H), 4.02-3.94 (m, 2H), 3.92-3.83 (m, 3H), 3.60-3.44 (m, 5H), 3.10-3.01 (m, 1H), 2.09-1.98 (m, 2H), 1.86-1.59 (m, 4H).

Analogously to "A26", 5-(2-chloropyrimidin-4-yl)-2-(tetrahydropyran-4-yloxy)benzonitrile and trans-4-(4-aminopyrazol-1-yl)cyclohexanol give the compound 5-{2-[1-(4-hydroxycyclohexyl)-1H-pyrazol-4-ylamino]pyrimidin-4-yl}-2-(tetrahydropyran-4-yloxy)benzonitrile ("A101")

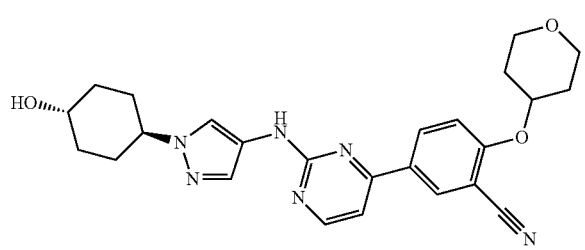 [SMILES: N#Cc1cc(-c2ccnc(Nc3cnn([C@H]4CC[C@H](O)CC4)c3)n2)ccc1OC1CCOCC1]

HPLC-MS Rt. [min] 1.915; HPLC-MS [M+H] 461;

¹H NMR (500 MHz, DMSO-d₆) δ [ppm] 9.47 (s, 1H), 8.50 (dd, J=11.7, 3.7, 2H), 8.41 (dd, J=9.0, 2.3, 1H), 7.96 (s, 1H), 7.61-7.50 (m, 2H), 7.34 (d, J=5.2, 1H), 5.00-4.90 (m, 1H), 4.63 (d, J=4.4, 1H), 4.15-4.04 (m, 1H), 3.94-3.83 (m, 2H), 3.61-3.46 (m, 3H), 2.11-1.88 (m, 6H), 1.86-1.63 (m, 4H), 1.43-1.29 (m, 2H).

Analogously to "A11", (3-aminopyrazin-2-yl)methanol gives the compound 5-[2-(3-hydroxymethylpyrazin-2-ylamino)pyridin-4-yl]-2-(tetrahydropyran-4-yloxy)benzonitrile ("A102")

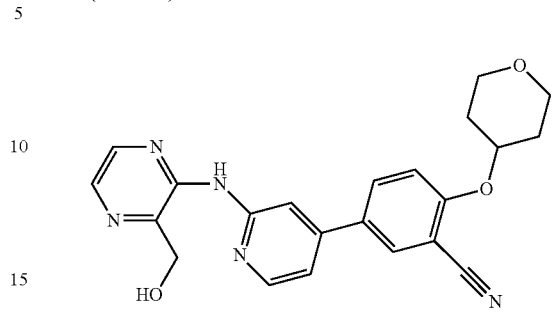

HPLC-MS Rt. [min] 1.530; HPLC-MS [M+H] 404;

¹H NMR (400 MHz, DMSO-d₆) δ [ppm] 9.41 (s, 1H), 8.49 (s, 1H), 8.34 (d, J=5.2, 1H), 8.24 (d, J=2.7, 1H), 8.15 (d, J=2.4, 1H), 8.06 (d, J=2.7, 1H), 8.03 (dd, J=8.9, 2.4, 1H), 7.53 (d, J=9.0, 1H), 7.36 (dd, J=5.3, 1.6, 1H), 6.23 (t, J=5.3, 1H), 4.97-4.87 (m, 1H), 4.80 (d, J=5.1, 2H), 3.95-3.82 (m, 2H), 3.63-3.51 (m, 2H), 2.10-1.98 (m, 2H), 1.77-1.61 (m, 2H).

Analogously to "A26", 5-(2-chloropyrimidin-4-yl)-2-cyclobutylmethoxybenzonitrile and 1-(2-methoxyethyl)-1H-pyrazol-4-ylamine give the compound 2-cyclobutylmethoxy-5-{2-[1-(2-methoxyethyl)-1H-pyrazol-4-ylamino]pyrimidin-4-yl}benzonitrile ("A103")

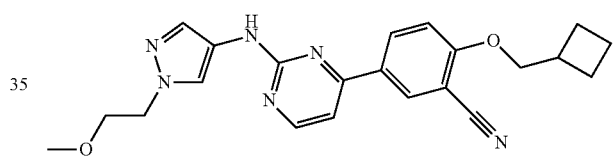

HPLC-MS Rt. [min] 2.839; HPLC-MS [M+H] 405;

¹H NMR (500 MHz, DMSO-d₆) δ [ppm] 9.47 (s, 1H), 8.48 (d, J=1.8, 2H), 8.43 (d, J=8.9, 1H), 7.94 (s, 1H), 7.57 (s, 1H), 7.41 (d, J=9.0, 1H), 7.33 (d, J=5.2, 1H), 4.29-4.18 (m, 4H), 3.68 (t, J=5.2, 2H), 3.25 (s, 3H), 2.85-2.73 (m, 1H), 2.17-2.04 (m, 2H), 1.99-1.83 (m, 4H).

Analogously to "A11", 5-morpholin-4-ylmethylpyridin-2-ylamine gives the compound 5-[2-(5-morpholin-4-ylmethylpyridin-2-ylamino)pyridin-4-yl]-2-(tetrahydropyran-4-yloxy)benzonitrile ("A118")

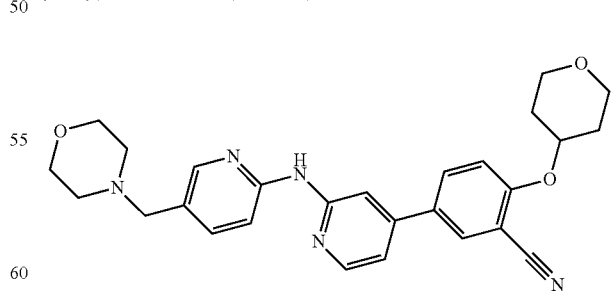

HPLC-MS Rt. [min] 1.278; HPLC-MS [M+H] 472;

¹H NMR (500 MHz, DMSO-d₆) δ [ppm] 9.67 (s, 1H), 8.26 (d, J=5.3, 1H), 8.16-8.11 (m, 2H), 8.09 (d, J=2.4, 1H), 7.99-7.94 (m, 2H), 7.76 (d, J=8.5, 1H), 7.60 (dd, J=8.6, 2.3, 1H), 7.52 (d, J=9.1, 1H), 7.20 (dd, J=5.3, 1.6, 1H), 4.95-4.84 (m, 1H), 3.92-3.83 (m, 2H), 3.61-3.50 (m, 6H), 3.38 (s, 2H), 2.36 (s, 4H), 2.10-1.99 (m, 2H), 1.75-1.62 (m, 2H).

Examples 105-117

Analytical Methods

LCMS Analysis:
Method A: A—0.1% of TFA in H₂O, B—0.1% of TFA in ACN: flow rate 2.0 ml/min
Column: XBridge C8 (50×4.6 mm, 3.5μ)
Method B: A—10 mM NH₄HCO₃, B: ACN; flow rate: 1.0 ml/min
Column: XBridge C8 (50×4.6 mm, 3.5μ),
¹H NMR:
Bruker 400 MHz
HPLC:
Method A:
Method: A—0.1% of TFA in H₂O, B—0.1% of TFA in ACN: flow rate—2.0 ml/min.
Column: XBridge C8 (50×4.6 mm, 3.5μ).

Synthesis of 5-bromo-2-cyclopropylmethoxybenzonitrile

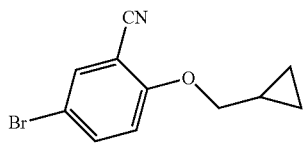 [SMILES: N#Cc1cc(Br)ccc1OCC1CC1]

Sodium hydride, 60% suspension in oil (3.6 g, 0.09 mol), is added to a solution of cyclopropylmethanol (6.49 g, 0.09 mol) in dry DMF (200 ml) at 0° C. under nitrogen. After 30 min at 0° C., 5-bromo-2-fluorobenzonitrile (12.0 g, 0.06 mol) in dry DMF (50 ml) is added, and the reaction is stirred at 50° C. for 16 h. Ice-water (200 ml) is added to the reaction mixture, which is then extracted with ethyl acetate (2×200 ml). The organic phases are washed with water (2×200 ml) and saturated sodium chloride solution (1×200 ml) and dried over sodium sulfate. After removal of the solvent, the crude product is purified by chromatography, giving 14 g of a yellow oil;
¹H NMR (400 MHz, CDCl₃): δ [ppm] 7.65 (d, J=2.48 Hz, 1H), 7.59 (dd, J=2.48, 8.96 Hz, 1H), 6.84 (d, J=9.00 Hz, 1H), 3.92 (d, J=6.84 Hz, 2H), 1.27-1.34 (m, 1H), 0.65-0.09 (m, 2H), 0.35-0.41 (m, 2H);
LCMS: (method A): 252 (M+H), RT 4.96 min.

Synthesis of 2-cyclopropylmethoxy-5-(4,4,5,5-tetramethyl-1,3,2-dioxaborolan-2-yl)benzonitrile

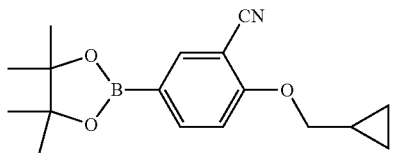 [SMILES: CC1(C)OB(c2ccc(OCC3CC3)c(C#N)c2)OC1(C)C]

A solution of 5-bromo-2-cyclopropylmethoxybenzonitrile (14.0 g, 0.055 mol) in 1,4-dioxane (200 ml) is degassed for 10 min, bis(pinacolato)diboron (15.5 g, 0.061 mol), [1,1'-bis(diphenylphosphino)ferrocene]palladium (II) dichloride (1.0 g, 0.00138 mol), 1,1'-bis(diphenylphosphino)ferrocene (0.75 g, 0.0138 mol) and potassium acetate (10.9 g, 0.111 mol) are added at room temperature. The mixture is boiled under reflux for 18 h. The mixture is allowed to cool to room temperature and filtered off. The filtrate is evaporated in a rotary evaporator and taken up with ethyl acetate (300 ml), washed with water (2×200 ml) and saturated sodium chloride solution (1×200 ml) and dried over sodium sulfate. After filtration, the crude product is purified by chromatography, giving 9 g of the desired product as white solid;
¹H NMR (400 MHz, CDCl₃): δ [ppm] 8.01 (d, J=1.56 Hz, 1H), 7.91 (dd, J=1.64, 8.48 Hz, 1H), 6.92 (d, J=8.48 Hz, 1H), 3.96 (d, J=6.84 Hz, 2H), 1.34 (s, 12H), 1.22-1.30 (m, 1H), 0.65-0.70 (m, 2H), 0.41 (t, J=4.92 Hz, 2H).

Synthesis of 5-(2-chloropyridin-4-yl)-2-cyclopropylmethoxybenzonitrile

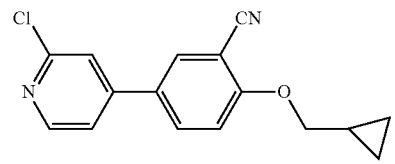 [SMILES: N#Cc1cc(-c2ccnc(Cl)c2)ccc1OCC1CC1]

A solution of 2-cyclopropylmethoxy-5-(4,4,5,5-tetramethyl-1,3,2-dioxaborolan-2-yl)benzonitrile (3.0 g, 0.010 mol) in acetonitrile (60 ml) and water (20 ml) is degassed for 10 min. 4-Bromo-2-chloropyridine (1.92 g, 0.010 mol), potassium carbonate (2.76 g, 0.02 mol) and tetrakis(triphenyl phosphine)palladium(0) (0.11 g, 0.0001 mol) are added. The reaction mixture is stirred at 90° C. for 6 h. The mixture is cooled to room temperature, filtered and evaporated in a rotary evaporator. The residue is taken up in ethyl acetate (200 ml), washed with water (2×200 ml) and saturated sodium chloride solution (1×200 ml). The mixture is subsequently dried over sodium sulfate, evaporated in a rotary evaporator and chromatographed for purification, giving 2.1 g of a pale-yellow solid;
¹H NMR (400 MHz, CDCl₃): δ [ppm] 8.44 (d, J=5.24 Hz, 1H), 7.83 (s, 1H), 7.75-7.83 (m, 1H), 7.48 (s, 1H), 7.45 (dd, J=0.44, 1.46 Hz, 1H), 7.07 (d, J=8.84 Hz, 1H), 4.02 (q, J=2.76 Hz, 2H), 1.33-1.37 (m, 1H), 0.69-0.73 (m, 2H), 0.41-0.45 (m, 2H); LCMS: (method A) 285 (M+H), RT 4.90 min.

Synthesis of 5-bromo-2-cyclobutylmethoxybenzonitrile

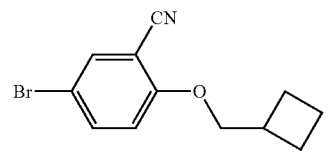 [SMILES: N#Cc1cc(Br)ccc1OCC1CCC1]

In an analogous manner as described above for 5-bromo-2-cyclopropylmethoxybenzonitrile, 5 g of 5-bromo-2-cyclobutylmethoxybenzonitrile are obtained from cyclobutanemethanol (2.58 g, 0.03 mol) and 5-bromo-2-fluorobenzonitrile (5.0 g, 0.025 mol) as yellow oil;

¹H NMR (400 MHz, CDCl₃): δ [ppm] 7.65 (d, J=2.48 Hz, 1H), 7.60 (dd, J=2.48, 8.96 Hz, 1H), 6.85 (d, J=8.96 Hz, 1H), 4.02 (d, J=6.28 Hz, 2H), 2.79-2.86 (m, 1H), 2.13-2.20 (m, 2H), 1.96-2.02 (m, 4H).

Synthesis of 2-cyclobutylmethoxy-5-(4,4,5,5-tetramethyl-1,3,2-dioxaborolan-2-yl)benzonitrile

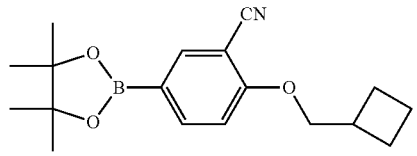 [SMILES: CC1(C)OB(c2ccc(OCC3CCC3)c(C#N)c2)OC1(C)C]

The preparation succeeds in a similar manner as described above for 2-cyclopropylmethoxy-5-(4,4,5,5-tetramethyl-1,3,2-dioxaborolan-2-yl)benzonitrile with 5-bromo-2-cyclobutylmethoxybenzonitrile (5.0 g, 0.018 mol), giving 3.5 g of the desired product as colourless oil;
¹H NMR (400 MHz, CD₃OD): δ [ppm] 7.90-7.96 (m, 2H), 7.17 (d, J=8.52 Hz, 1H), 4.13 (d, J=6.16 Hz, 2H), 2.81-2.88 (m, 1H), 2.13-2.20 (m, 2H), 2.02-2.05 (m, 4H), 1.31 (s, 12H).

Synthesis of 5-(2-chloropyridin-4-yl)-2-cyclobutylmethoxybenzonitrile

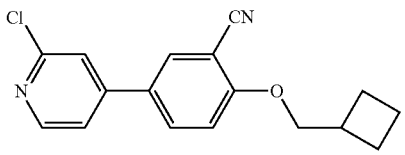 [SMILES: N#Cc1cc(-c2ccnc(Cl)c2)ccc1OCC1CCC1]

With 2-cyclobutylmethoxy-5-(4,4,5,5-tetramethyl-1,3,2-dioxaborolan-2-yl)benzonitrile (5.0 g, 0.015 mol) and 4-bromo-2-chloropyridine (3.0 g, 0.015 mol), 2.5 g of the desired product are obtained as pale-yellow solid in a similar manner as described for 5-(2-chloropyridin-4-yl)-2-cyclopropylmethoxybenzonitrile;
¹H NMR (400 MHz, DMSO-d₆): δ [ppm] 8.45 (s, 1H), 8.44 (s, 1H), 8.18 (dd, J=2.44, 8.94 Hz, 1H), 7.94 (d, J=1.20 Hz, 1H), 7.80 (dd, J=1.64, 5.28 Hz, 1H), 7.38 (d, J=8.96 Hz, 1H), 4.20 (d, J=6.40 Hz, 2H), 2.75-2.79 (m, 1H), 2.05-2.12 (m, 2H), 1.86-1.94 (m, 4H);
LCMS: (method A) 299 (M+H), RT 5.40 min.

Synthesis of tert-butyl 4-(4-bromo-2-cyanophenoxymethyl)piperidine-1-carboxylate

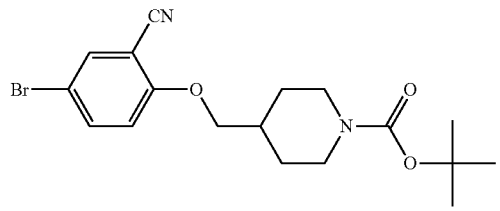 [SMILES: CC(C)(C)OC(=O)N1CCC(COc2ccc(Br)cc2C#N)CC1]

With N—BOC-4-piperidinemethanol (6.45 g, 0.03 mol) and 5-bromo-2-fluorobenzonitrile (5.0 g, 0.025 mol), 7.0 g of the desired product are obtained as pale-yellow oil as described above for 5-bromo-2-cyclopropylmethoxybenzonitrile;

¹H NMR (400 MHz, CDCl₃): δ [ppm] 7.59-7.65 (m, 2H), 6.84 (d, J=8.96 Hz, 1H), 4.15-4.18 (m, 2H), 3.87 (d, J=6.64 Hz, 2H), 2.66-2.79 (m, 2H), 2.03-2.08 (m, 1H), 1.84-1.88 (m, 2H), 1.45 (s, 9H), 1.24-1.28 (m, 2H);
LCMS: (method A) 297 (M+2), RT 5.67 min.

Synthesis of tert-butyl 4-[2-cyano-4-(4,4,5,5-tetramethyl-1,3,2-dioxaborolan-2-yl)phenoxymethyl]piperidine-1-carboxylate

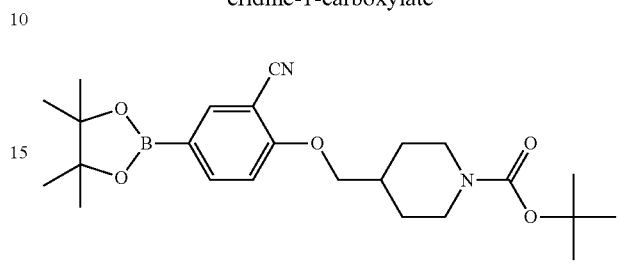

With tert-butyl 4-(4-bromo-2-cyanophenoxymethyl)piperidine-1-carboxylate (7.0 g, 0.17 mol), 6.0 g of the desired product are obtained as colourless oil as described above for 2-cyclopropylmethoxy-5-(4,4,5,5-tetramethyl-1,3,2-dioxaborolan-2-yl)benzonitrile;
¹H NMR (400 MHz, CDCl₃): δ [ppm] 8.01 (s, 1H), 7.93 (dd, J=1.60, 8.46 Hz, 1H), 6.93 (d, J=8.52 Hz, 1H), 4.10-4.20 (m, 2H), 3.93 (d, J=6.60 Hz, 2H), 2.77 (t, J=12.08 Hz, 2H), 2.05-2.10 (m, 1H), 1.88-1.91 (m, 2H), 1.47 (s, 9H), 1.36 (s, 12H), 1.22-1.29 (m, 2H).

Synthesis of 2-(piperidin-4-ylmethoxy)-5-(4,4,5,5-tetramethyl-1,3,2-dioxaborolan-2-yl)benzonitrile

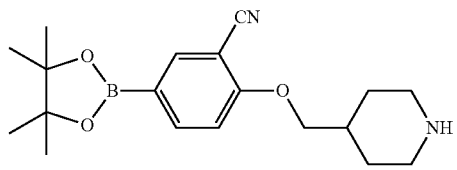

HCl in dioxane (50 ml) is added to a solution of tert-butyl 4-[2-cyano-4-(4,4,5,5-tetramethyl-1,3,2-dioxaborolan-2-yl)phenoxymethyl]piperidine-1-carboxylate (6.0 g, 0.0135 mol) in 1,4-dioxane (50 ml), and the mixture is stirred at room temperature for 16 h. The mixture is evaporated in a rotary evaporator and employed in the next step without purification.

Synthesis of 2-(1-acetylpiperidin-4-ylmethoxy)-5-(4,4,5,5-tetramethyl-1,3,2-dioxaborolan-2-yl)benzonitrile

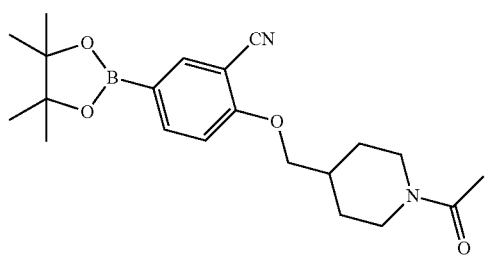 [SMILES: CC(=O)N1CCC(COc2ccc(B3OC(C)(C)C(C)(C)O3)cc2C#N)CC1]

Glacial acetic acid (2.1 g, 0.035 mol), triethylamine (3.5 g, 0.035 mol) and 1-propanephosphonic anhydride (60% w/w in ethyl acetate) (11 ml, 0.0174 mol) are added to a solution of 2-(piperidin-4-ylmethoxy)-5-(4,4,5,5-tetramethyl-1,3,2-dioxaborolan-2-yl)benzonitrile (4.0 g, 0.0116 mol) in dichloromethane (40 ml) at 0° C. under nitrogen. The reaction is stirred at room temperature for 15 h. The solution is evaporated and poured into water (200 ml). The mixture is extracted with dichloromethane (100 ml×2) and evaporated in a rotary evaporator. The crude product is purified by chromatography, giving 6.0 g of the desired product as colourless oil;

$^1$H NMR (400 MHz, CD$_3$OD): δ [ppm] 7.95 (dd, J=1.64, 8.48 Hz, 1H), 7.91 (d, J=1.48 Hz, 1H), 7.18 (d, J=8.52 Hz, 1H), 4.57-4.87 (m, 1H), 3.98-4.08 (m, 3H), 3.16-3.23 (m, 1H), 2.67-2.74 (m, 1H), 2.15-2.29 (m, 1H), 2.12 (s, 3H), 1.90-2.02 (m, 2H), 1.35-1.45 (m, 2H), 1.33 (s, 12H).

Synthesis of 2-(1-acetylpiperidin-4-ylmethoxy)-5-(2-chloropyridin-4-yl)benzonitrile

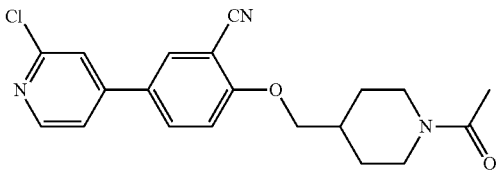 [SMILES: CC(=O)N1CCC(COc2ccc(-c3ccnc(Cl)c3)cc2C#N)CC1]

In a similar manner as described above for 5-(2-chloropyridin-4-yl)-2-cyclobutylmethoxybenzonitrile, 1.0 g of the desired product is obtained as white solid with 2-(1-acetylpiperidin-4-ylmethoxy)-5-(4,4,5,5-tetramethyl-1,3,2-dioxaborolan-2-yl)benzonitrile (2.0 g, 0.005 mol) and 4-bromo-2-chloropyridine (0.96 g, 0.005 mol);

$^1$H NMR (400 MHz, DMSO-d$_6$): δ [ppm] 8.44 (s, 1H), 8.34 (d, J=2.44 Hz, 1H), 8.18 (dd, J=2.44, 8.92 Hz, 1H), 7.93 (d, J=1.16 Hz, 1H), 7.80 (dd, J=1.64, 5.32 Hz, 1H), 7.39 (d, J=9.00 Hz, 1H), 4.39-4.42 (m, 1H), 3.92-4.12 (m, 2H), 3.84-3.88 (m, 1H), 3.06-3.06 (m, 1H), 2.56-2.57 (m, 1H), 2.01-2.16 (m, 1H), 1.99 (s, 3H), 1.76-1.81 (m, 2H), 1.13-1.29 (m, 2H); LCMS: (method A) 370 (M+H), RT. 4.02 min.

Synthesis of 2-cyclopropylmethoxy-5-[2-(1H-pyrazol-4-ylamino)pyridin-4-yl]-benzonitrile ("A104")

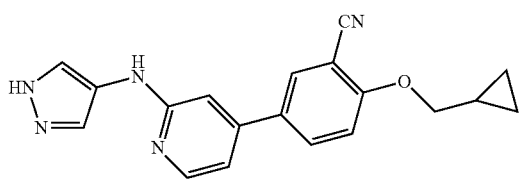 [SMILES: N#Cc1cc(-c2ccnc(Nc3cn[nH]c3)c2)ccc1OCC1CC1]

A solution of 5-(2-chloropyridin-4-yl)-2-cyclopropylmethoxybenzonitrile (0.25 g, 0.0878 mmol) in t-butanol (5 ml) is degassed with nitrogen for 5 min. 1H-Pyrazol-4-ylamine hydrochloride (0.12 g, 1.08 mmol), Josiphos (24.3 mg, 0.00439 mmol) and tris(dibenzylideneacetone)dipalladium(0) (40.0 mg, 0.00439 mmol) is then added. A solution of 1.6M lithium bis(trimethylsilyl)amide in THF (0.35 g, 2.1 mmol) is added dropwise. The mixture is irradiated in the microwave at 140° C. for 2 h. 30 ml of water are then added, and the mixture is filtered. The crude product is purified by chromatography, giving 26.6 mg of the desired product as brown solid;

$^1$H NMR (400 MHz, DMSO-d$_6$): δ [ppm] 12.47 (bs, 1H), 8.80 (s, 1H), 8.13 (d, J=5.36 Hz, 1H), 8.04 (d, J=2.16 Hz, 1H), 7.92 (dd, J=2.24, 8.82 Hz, 2H), 7.54 (bs, 1H), 7.34 (d, J=8.92 Hz, 1H), 6.92 (d, J=5.28 Hz, 1H), 6.86 (s, 1H), 4.06 (d, J=7.00 Hz, 2H), 1.23-1.30 (m, 1H), 0.59-0.63 (m, 2H), 0.31-0.39 (m, 2H);

LCMS: (method A) 332 (M+H), RT. 3.25 min;
HPLC: (method A) RT. 3.23 min.

Synthesis of 2-cyclopropylmethoxy-5-{2-[1-(2-methoxyethyl)-1H-pyrazol-4-ylamino]-pyridin-4-yl}benzonitrile ("A105")

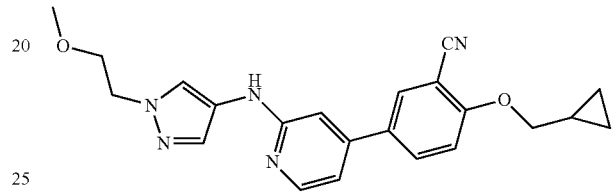

Caesium carbonate (0.17 g, 0.54 mmol) and 2-bromoethyl methyl ether (0.045 g, 0.325 mmol) are added to a solution of the 2-cyclopropylmethoxy-5-[2-(1H-pyrazol-4-ylamino)pyridin-4-yl]benzonitrile prepared above (0.09 g, 0.27 mmol) in dry DMF (2 ml). The reaction mixture is warmed at 80° C. for 8 h. Ice is added, and the mixture is extracted with ethyl acetate (2×50 ml). The organic phase is washed with water (1×25 ml) and dried over sodium sulfate. The mixture is then evaporated in a rotary evaporator. The crude product is purified by chromatography, giving 5.8 mg of the desired product as brown solid;

$^1$H NMR (400 MHz, DMSO-d$_6$): δ [ppm] 8.31 (s, 1H), 8.14 (d, J=5.40 Hz, 1H), 8.04 (d, J=2.36 Hz, 1H), 7.97 (s, 1H), 7.93 (dd, J=2.40, 8.92 Hz, 1H), 7.46 (d, J=0.44 Hz, 1H), 7.34 (d, J=8.96 Hz, 1H), 6.94 (dd, J=1.56, 5.44 Hz, 1H), 6.85 (s, 1H), 4.20 (t, J=5.40 Hz, 2H), 4.06 (d, J=7.04 Hz, 2H), 3.66 (t, J=5.32 Hz, 2H), 3.22 (s, 3H), 1.24-1.30 (m, 1H), 0.60-0.62 (m, 2H), 0.38-0.40 (m, 2H);

LCMS: (method A) 390 (M+H), RT. 3.42 min;
HPLC: (method A) RT. 3.44 min.

Synthesis of 2-cyclopropylmethoxy-5-[2-(5-hydroxymethylpyridin-2-ylamino)pyridin-4-yl]benzonitrile ("A106")

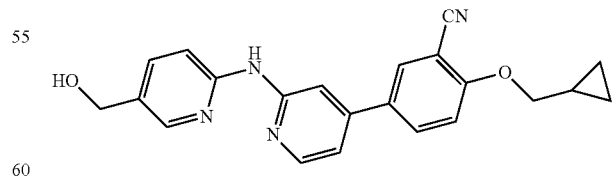

As described above for 2-cyclopropylmethoxy-5-[2-(1H-pyrazol-4-ylamino)pyridin-4-yl]benzonitrile ("A104"), 18.5 mg of the desired compound are obtained with 5-(2-chloropyridin-4-yl)-2-cyclopropylmethoxybenzonitrile (0.2 g, 0.702 mmol) and (6-amino-3-pyridinyl)methanol (0.104 g, 0.843 mmol) as yellow solid;

¹H NMR (400 MHz, DMSO-d₆): δ [ppm] 9.67 (s, 1H), 8.26 (d, J=5.32 Hz, 1H), 8.17 (d, J=1.92 Hz, 1H), 8.08 (d, J=2.40 Hz, 1H), 7.97 (d, J=2.40 Hz, 1H), 7.93 (d, J=1.00 Hz, 1H), 7.78 (d, J=8.56 Hz, 1H), 7.62 (dd, J=2.36, 8.58 Hz, 1H), 7.38 (d, J=9.00 Hz, 1H), 7.19 (dd, J=1.68, 5.36 Hz, 1H), 5.12 (t, J=5.56 Hz, 1H), 4.42 (d, J=5.60 Hz, 2H), 4.08 (d, J=7.00 Hz, 2H), 1.24-1.36 (m, 1H), 0.61-0.63 (m, 2H), 0.38-0.40 (m, 2H);

LCMS: (method B) 373 (M+H), RT. 5.46 min;

HPLC: (method B) RT. 9.92 min.

Synthesis of tert-butyl 4-(4-nitro-1H-pyrazol-1-yl)piperidine-1-carboxylate

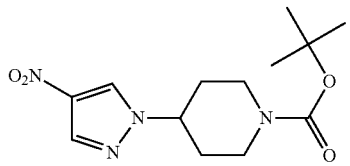

1-Boc-4-hydroxy piperidine (2.6 g, 0.0132 mol), triphenylphosphine (4.1 g, 0.015 mol) and di-tert-butyl azodicarboxylate (3.9 g, 0.0172 mol) are added in portions to a solution of 4-nitro-1H-pyrazole (1.5 g, 0.0132 mol) in THF (40 ml) at 10-15° C. The reaction mixture is stirred at room temperature for 48 h. The mixture is evaporated in a rotary evaporator, and the crude material is chromatographed, giving 2.1 g of a white solid;

¹H NMR (400 MHz, DMSO-d₆): δ [ppm] 8.94 (s, 1H), 8.27 (s, 1H), 4.49-4.41 (m, 1H), 4.04-4.0 (m, 2H), 2.88 (bs, 2H), 2.03-2.00 (m, 2H), 1.84-1.78 (m, 2H), 1.40 (s, 9H).

Synthesis of tert-butyl 4-(4-amino-1H-pyrazol-1-yl)piperidine-1-carboxylate

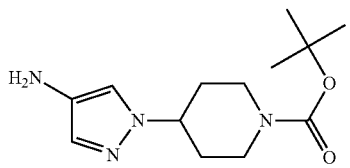 [SMILES: CC(C)(C)OC(=O)N1CCC(n2cc([N+](=O)[O-])cn2)CC1]

Palladium on carbon (10% w/w, 0.2 g) is added to a solution of tert-butyl 4-(4-nitro-1H-pyrazol-1-yl)piperidine-1-carboxylate (2.1 g, 0.0040 mol) in methanol (50 ml), and the mixture is hydrogenated at room temperature for 3 h. The catalyst is filtered off, and the solution is evaporated in a rotary evaporator. The residue is purified by chromatography, giving 1.1 g of a brown oil;

¹H NMR (400 MHz, DMSO-d₆): δ [ppm] 7.05 (d, J=0.8 Hz, 1H), 6.89 (d, J=0.8 Hz, 1H), 4.14 (m, 1H), 3.99 (d, 2H), 3.84 (d, 2H), 2.84 (bs, 2H), 1.90-1.87 (m, 2H), 1.70-1.61 (m, 2H), 1.40 (s, 9H);

tert-Butyl 4-(4-amino-1H-pyrazol-1-yl)piperidine-1-carboxylate is employed in the synthesis of "A16".

Synthesis of tert-butyl 4-{3-[4-(3-cyano-4-cyclopropylmethoxyphenyl)pyridin-2-yl-amino]pyrazol-1-yl}piperidine-1-carboxylate

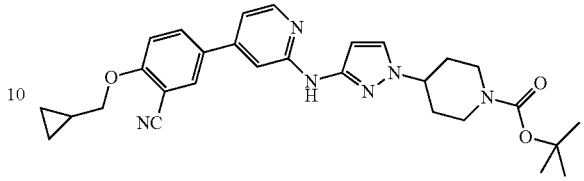

The preparation is carried out as described above for 2-cyclopropylmethoxy-5-[2-(5-hydroxymethylpyridin-2-ylamino)pyridin-4-yl]benzonitrile;

¹H NMR (400 MHz, CDCl₃): δ [ppm] 8.17 (s, 1H), 7.76 (d, J=2.32 Hz, 1H), 7.68-7.71 (m, 2H), 7.53 (d, J=0.36 Hz, 1H), 7.02 (d, J=8.84 Hz, 1H), 6.83 (dd, J=1.56, 5.46 Hz, 1H), 6.66 (s, 1H), 6.40 (s, 1H), 4.24-4.30 (m, 3H), 4.00 (d, J=6.88 Hz, 2H), 2.85-2.92 (m, 2H), 2.15-2.19 (m, 2H), 1.92-1.96 (m, 2H), 1.49 (s, 9H), 1.25-1.27 (m, 1H), 0.68-0.71 (m, 2H), 0.42-0.45 (m, 2H);

LCMS: (method A) 515 (M+H), RT. 4.43 min.

Synthesis of 2-cyclopropylmethoxy-5-[2-(1-piperidin-4-yl-1H-pyrazol-3-ylamino)pyridin-4-yl]benzonitrile ("A107")

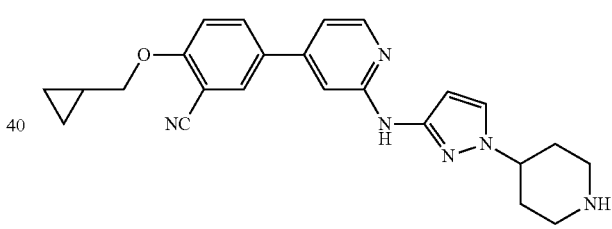

HCl in dioxane (10 ml) are added to a solution of tert-butyl 4-{3-[4-(3-cyano-4-cyclopropylmethoxyphenyl)pyridin-2-ylamino]pyrazol-1-yl}piperidine-1-carboxylate (0.12 g, 0.23 mmol) in 1,4-dioxane (10 ml). The entire mixture is stirred at room temperature for 6 h. The reaction solution is evaporated in a rotary evaporator and rendered basic using 10% sodium bicarbonate solution (20 ml). The mixture is stirred for 10 min. The solid is filtered off, washed with diethyl ether (20 ml) and dried, giving 85.4 mg of the desired material as brown solid;

¹H NMR (400 MHz, DMSO-d₆): δ [ppm] 8.82 (s, 1H), 8.14 (d, J=5.40 Hz, 1H), 8.04 (d, J=2.28 Hz, 1H), 7.98 (s, 1H), 7.93 (dd, J=2.28, 8.88 Hz, 1H), 7.46 (s, 1H), 7.34 (d, J=8.96 Hz, 1H), 6.93 (dd, J=1.24, 5.38 Hz, 1H), 6.86 (s, 1H), 4.07-4.15 (m, 1H), 4.06 (d, J=7.04 Hz, 2H), 3.00-3.03 (m, 2H), 2.56-2.59 (m, 2H), 1.90-1.92 (m, 2H), 1.69-1.79 (m, 2H), 1.25-1.32 (m, 1H), 0.59-0.63 (m, 2H), 0.38-0.40 (m, 2H);

LCMS: (method A) 415 (M+H), RT. 3.00 min;

HPLC: (method A) RT. 3.00 min.

Synthesis of 5-morpholin-4-ylpyridin-2-ylamine

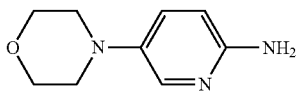

A solution of 2-amino-5-bromopyridine (2.0 g, 0.011 mol) in t-butanol (5 ml) is degassed with nitrogen for 5 min. Morpholine (1.4 g, 0.016 mol), Davephos (0.4 g, 0.001 mol) and tris(dibenzylideneacetone)dipalladium(0) (0.25 g, 0.027 mmol) is added. A 1.6M solution of lithium bis(trimethylsilyl)amide in THF (5.51 g, 0.033 mol) is then added dropwise. The reaction mixture is irradiated in the microwave at 150° C. for 2 h. Water is added (30 ml), and the mixture is extracted with ethyl acetate (2×100 ml). The organic phases are washed with water (1×100 ml) and dried over sodium sulfate. The crude material is employed in the next step without purification. 5-Morpholin-4-ylpyridin-2-ylamine is employed in the synthesis of "A7".

Synthesis of 2-cyclopropylmethoxy-5-[2-(5-morpholin-4-ylpyridin-2-ylamino)pyridin-4-yl]benzonitrile ("A108")

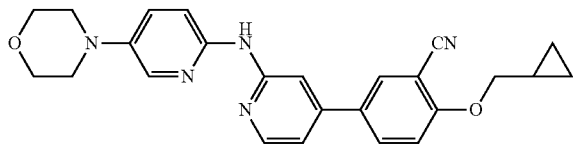 [SMILES: N#Cc1cc(-c2ccnc(Nc3ccc(N4CCOCC4)cn3)c2)ccc1OCC1CC1]

The preparation is carried out as described above for 2-cyclopropylmethoxy-5-[2-(5-hydroxymethylpyridin-2-ylamino)pyridin-4-yl]benzonitrile, giving 50.9 mg of a brown solid in 16% yield;

$^1$H NMR (400 MHz, DMSO-$d_6$): δ [ppm] 9.42 (s, 1H), 8.21 (d, J=5.28 Hz, 1H), 8.06 (d, J=2.28 Hz, 1H), 7.93-7.94 (m, 2H), 7.82 (s, 1H), 7.73 (d, J=9.04 Hz, 1H), 7.36-7.42 (m, 2H), 7.12 (dd, J=1.48, 5.36 Hz, 1H), 4.07 (d, J=7.00 Hz, 2H), 3.74 (t, J=4.92 Hz, 4H), 3.05 (t, J=4.76 Hz, 4H), 1.24-1.29 (m, 1H), 0.59-0.64 (m, 2H), 0.37-0.40 (m, 2H);

LCMS: (method A) 428 (M+H), RT. 3.98 min;
HPLC: (method A) RT. 3.93 min.

Synthesis of 2-cyclobutylmethoxy-5-[2-(1H-pyrazol-4-ylamino)pyridin-4-yl]benzonitrile ("A109")

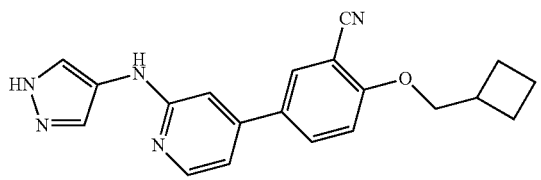 [SMILES: N#Cc1cc(-c2ccnc(Nc3cn[nH]c3)c2)ccc1OCC1CCC1]

Preparation as described in the case of 2-cyclopropylmethoxy-5-[2-(1H-pyrazol-4-ylamino)pyridin-4-yl]benzonitrile ("A104"), giving 20.4 mg of a brown solid (41% yield);

$^1$H NMR (400 MHz, DMSO-$d_6$): δ [ppm] 12.45 (bs, 1H), 8.77 (s, 1H), 8.13 (d, J=5.36 Hz, 1H), 8.04 (d, J=2.16 Hz, 1H), 7.92-7.95 (m, 2H), 7.52 (s, 1H), 7.37 (d, J=8.92 Hz, 1H), 6.92 (d, J=5.36 Hz, 1H), 6.85 (s, 1H), 4.17 (d, J=6.36 Hz, 2H), 2.50-2.80 (m, 1H), 2.06-2.10 (m, 2H), 1.90-1.96 (m, 4H);

LCMS: (method A) 346 (M+H), RT. 3.69 min;
HPLC: (method A) RT. 3.69 min.

Synthesis of 2-cyclobutylmethoxy-5-{2-[1-(2-methoxyethyl)-1H-pyrazol-4-ylamino]-pyridin-4-yl}benzonitrile ("A110")

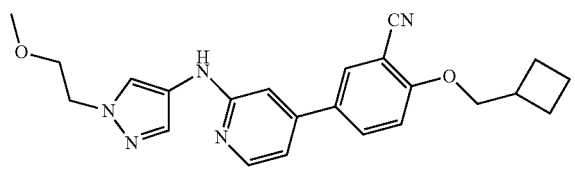 [SMILES: COCCn1cc(Nc2cc(-c3ccc(OCC4CCC4)c(C#N)c3)ccn2)cn1]

Preparation as described for 2-cyclopropylmethoxy-5-{2-[1-(2-methoxyethyl)-1H-pyrazol-4-ylamino]pyridin-4-yl}benzonitrile ("A105"); yield 18% (18.4 mg, yellow solid);

$^1$H NMR (400 MHz, DMSO-$d_6$): δ [ppm] 8.82 (s, 1H), 8.14 (d, J=5.40 Hz, 1H), 8.04 (d, J=2.40 Hz, 1H), 7.93-7.97 (m, 2H), 7.46 (d, J=0.40 Hz, 1H), 7.37 (d, J=8.96 Hz, 1H), 6.94 (dd, J=1.56, 5.42 Hz, 1H), 6.85 (d, J=0.84 Hz, 1H), 4.17-4.22 (m, 4H), 3.62-3.68 (m, 2H), 3.23 (s, 3H), 2.73-2.80 (m, 1H), 2.06-2.11 (m, 2H), 1.86-1.94 (m, 4H);

LCMS: (method A) 404 (M+H), RT. 3.91 min;
HPLC: (method A) RT. 3.89 min.

Synthesis of 2-cyclobutylmethoxy-5-[2-(5-hydroxymethylpyridin-2-ylamino)pyridin-4-yl]benzonitrile ("A111")

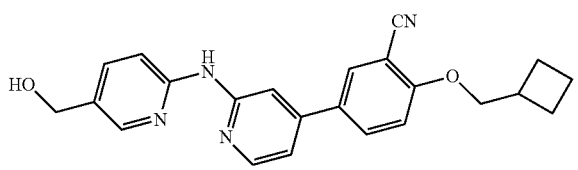 [SMILES: N#Cc1cc(-c2ccnc(Nc3ccc(CO)cn3)c2)ccc1OCC1CCC1]

Preparation as described for 2-cyclopropylmethoxy-5-[2-(5-hydroxymethylpyridin-2-ylamino)pyridin-4-yl]benzonitrile ("A106"); yield: 32% (87.0 mg, yellow solid);

$^1$H NMR (400 MHz, DMSO-$d_6$): δ [ppm] 9.69 (s, 1H), 8.26 (d, J=5.32 Hz, 1H), 8.17 (d, J=1.88 Hz, 1H), 8.07 (d, J=2.36 Hz, 1H), 7.98 (dd, J=2.36, 8.88 Hz, 1H), 7.93 (d, J=0.88 Hz, 1H), 7.78 (d, J=8.52 Hz, 1H), 7.62 (dd, J=2.28, 8.56 Hz, 1H), 7.41 (d, J=8.96 Hz, 1H), 7.19 (dd, J=1.60, 5.36 Hz, 1H), 5.12 (t, J=5.56 Hz, 1H), 4.42 (d, J=5.56 Hz, 2H), 4.19 (d, J=6.44 Hz, 2H), 2.73-2.79 (m, 1H), 2.09-2.11 (m, 2H), 1.89-1.94 (m, 4H);

LCMS: (method A) 387 (M+H), RT. 4.02 min;
HPLC: (method A) RT. 3.99 min.

Synthesis of tert-butyl 4-{4-[4-(3-cyano-4-cyclobutylmethoxyphenyl)pyridin-2-ylamino]pyrazol-1-yl}piperidine-1-carboxylate

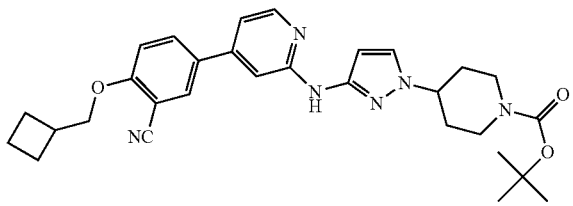 [SMILES: CC(C)(C)OC(=O)N1CCC(n2ccc(Nc3cc(-c4ccc(OCC5CCC5)c(C#N)c4)ccn3)n2)CC1]

The preparation is carried out as described in the case of tert-butyl 4-{3-[4-(3-cyano-4-cyclopropylmethoxyphenyl)pyridin-2-ylamino]pyrazol-1-yl}piperidine-1-carboxylate; yield: 27% (0.1 g, brown solid substance);

$^1$H NMR (400 MHz, DMSO-d$_6$): δ [ppm] 8.18 (s, 1H), 7.75 (d, J=2.32 Hz, 1H), 7.70 (dd, J=2.40, 8.74 Hz, 2H), 7.53 (d, J=0.40 Hz, 1H), 7.03 (d, J=8.84 Hz, 1H), 6.83 (dd, J=1.56, 5.40 Hz, 1H), 6.66 (d, J=0.88 Hz, 1H), 6.35 (b, 1H), 4.26-4.27 (m, 3H), 4.09 (d, J=6.28 Hz, 2H), 2.79-2.83 (m, 3H), 2.00-2.20 (m, 4H), 1.92-2.00 (m, 6H), 1.49 (s, 9H);

LCMS: (method A) 529 (M+H), RT. 4.78 min.

Synthesis of 2-cyclobutylmethoxy-5-[2-(1-piperidin-4-yl-1H-pyrazol-4-ylamino)pyridin-4-yl]benzonitrile ("A112")

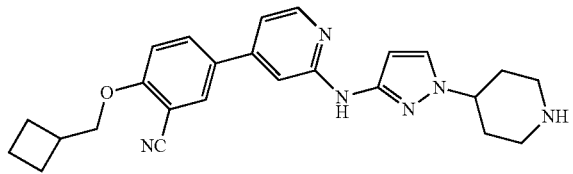 [SMILES: N#Cc1cc(-c2ccnc(Nc3ccn(C4CCNCC4)n3)c2)ccc1OCC1CCC1]

The preparation is carried out as described in the case of 2-cyclopropylmethoxy-5-[2-(1-piperidin-4-yl-1H-pyrazol-3-ylamino)pyridin-4-yl]benzonitrile ("A107"); yield: 92% (41.0 mg, brown solid);

$^1$H NMR (400 MHz, DMSO-d$_6$): δ [ppm] 8.82 (s, 1H), 8.14 (d, J=5.36 Hz, 1H), 8.04 (d, J=2.00 Hz, 1H), 7.93-7.98 (m, 2H), 7.46 (s, 1H), 7.37 (d, J=8.92 Hz, 1H), 6.93 (d, J=4.64 Hz, 1H), 6.86 (s, 1H), 4.12-4.18 (m, 4H), 3.00-3.03 (m, 2H), 2.75-2.79 (m, 1H), 2.56-2.59 (m, 1H), 2.06-2.10 (m, 2H), 1.86-1.96 (m, 6H), 1.73-1.78 (m, 2H);

LCMS: (method A) 429.2 (M+H), RT. 3.40 min;
HPLC: (method A) RT. 3.40 min.

Synthesis of 2-cyclobutylmethoxy-5-[2-(5-morpholin-4-ylpyridin-2-ylamino)pyridin-4-yl]benzonitrile ("A113")

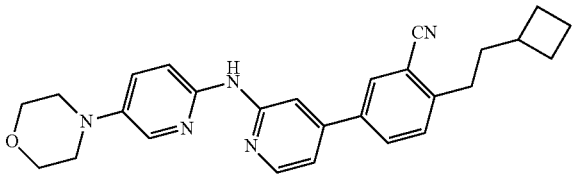 [SMILES: N#Cc1cc(-c2ccnc(Nc3ccc(N4CCOCC4)cn3)c2)ccc1CCC1CCC1]

The preparation is carried out as described in the case of 2-cyclopropylmethoxy-5-[2-(5-morpholin-4-ylpyridin-2-ylamino)pyridin-4-yl]benzonitrile ("A108"); yield: 16.5% (48.0 mg, yellow solid);

$^1$H NMR (400 MHz, DMSO-d$_6$): δ [ppm] 9.44 (s, 1H), 8.21 (d, J=5.36 Hz, 1H), 8.05 (d, J=2.36 Hz, 1H), 7.93-7.98 (m, 2H), 7.82 (d, J=0.80 Hz, 1H), 7.73 (d, J=9.08 Hz, 1H), 7.38-7.42 (m, 2H), 7.12 (dd, J=1.60, 5.36 Hz, 1H), 4.19 (dd, J=6.44, Hz, 1H), 3.74 (t, J=4.96 Hz, 4H), 3.05 (t, J=4.84 Hz, 4H), 2.73-2.79 (m, 1H), 2.09-2.10 (m, 2H), 1.88-1.94 (m, 4H);

LCMS: (method A) 442 (M+H), RT. 4.33 min;
HPLC: (method A) RT. 4.31 min.

Synthesis of 2-(1-acetylpiperidin-4-ylmethoxy)-5-{2-[1-(2-methoxyethyl)-1H-pyrazol-4-ylamino]pyridin-4-yl}benzonitrile ("A114")

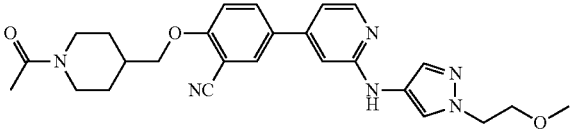 [SMILES: COCCn1cc(Nc2cc(-c3ccc(OCC4CCN(C(C)=O)CC4)c(C#N)c3)ccn2)cn1]

The preparation is carried out analogously as described in the case of 2-cyclopropylmethoxy-5-{2-[1-(2-methoxyethyl)-1H-pyrazol-4-ylamino]pyridin-4-yl}benzonitrile ("A110");

yield: 16% (5.7 mg, brown solid);

$^1$H NMR (400 MHz, CD$_3$OD): δ [ppm] (s, 1H), 8.12 (d, J=5.36 Hz, 1H), 7.89-7.95 (m, 3H), 7.54 (d, J=0.52 Hz, 1H), 7.27 (d, J=8.72 Hz, 1H), 6.91 (dd, J=1.56, 5.48 Hz, 1H), 6.83 (d, J=0.88 Hz, 1H), 4.58-4.62 (m, 1H), 4.27-4.29 (m, 2H), 3.99-4.09 (m, 3H), 3.75 (t, J=5.20 Hz, 2H), 3.29-3.28 (m, 3H), 3.16-3.23 (m, 1H), 2.71-2.72 (m, 1H), 2.13-2.24 (m, 1H), 2.12 (s, 3H), 1.91-2.03 (m, 2H), 1.29-1.46 (m, 2H);

LCMS: (method A) 475 (M+H), RT. 2.81 min;
HPLC: (method A) RT. 2.75 min.

Synthesis of 2-(1-acetylpiperidin-4-ylmethoxy)-5-[2-(5-hydroxymethylpyridin-2-ylamino)pyridin-4-yl]benzonitrile ("A115")

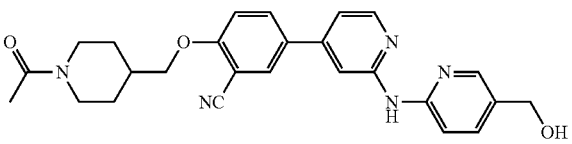 [SMILES: CC(=O)N1CCC(COc2ccc(-c3ccnc(Nc4ccc(CO)cn4)c3)cc2C#N)CC1]

The preparation is carried out analogously as described in the case of 2-cyclopropylmethoxy-5-[2-(5-hydroxymethylpyridin-2-ylamino)pyridin-4-yl]benzonitrile ("A106");

yield: 7.2% (16.9 mg, yellow solid);

$^1$H NMR (400 MHz, DMSO-d$_6$): δ [ppm] 9.68 (s, 1H), 8.26 (d, J=5.32 Hz, 1H), 8.17 (d, J=2.00 Hz, 1H), 8.08 (d, J=2.32 Hz, 1H), 7.98 (dd, J=2.32, 8.88 Hz, 1H), 7.93 (s, 1H), 7.78 (d, J=8.52 Hz, 1H), 7.62 (dd, J=2.16, 8.56 Hz, 1H), 7.42 (d, J=8.96 Hz, 1H), 7.19 (dd, J=1.32, 5.34 Hz, 1H), 5.11 (t, J=5.56 Hz, 1H), 4.40-4.43 (m, 3H), 4.06-4.13 (m, 2H), 3.85-3.88 (m, 1H), 3.04-3.10 (m, 1H), 2.57-2.66 (m, 1H), 2.06-2.11 (m, 1H), 1.98 (s, 3H), 1.77-1.85 (m, 2H), 1.08-1.30 (m, 2H);

LCMS: (method A) 458 (M+H), RT 2.93 min;
HPLC: (method A) RT. 2.89 min.

Synthesis of tert-butyl 4-(4-{4-[4-(1-acetylpiperidin-4-ylmethoxy)-3-cyanophenyl]-pyridin-2-ylamino}pyrazol-1-yl)piperidine-1-carboxylate

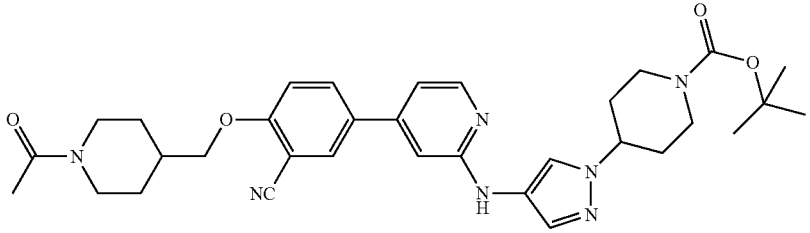 [SMILES: CC(=O)N1CCC(COc2ccc(-c3ccnc(Nc4cnn(C5CCN(C(=O)OC(C)(C)C)CC5)c4)c3)cc2C#N)CC1]

The preparation is carried out as described in the synthesis of tert-butyl 4-{3-[4-(3-cyano-4-cyclopropylmethoxyphenyl)pyridin-2-ylamino]pyrazol-1-yl}piperidine-1-carboxylate; yield: 37.0% (0.12 g, brown solid);

$^1$H NMR (400 MHz, DMSO-d$_6$): δ [ppm] 8.81 (s, 1H), 8.14 (d, J=5.44 Hz, 1H), 8.05 (s, 1H), 8.01 (s, 1H), 7.94 (dd, J=2.36, 8.90 Hz, 1H), 7.48 (d, J=0.36 Hz, 1H), 7.38 (d, J=8.96 Hz, 1H), 6.93 (dd, J=1.52, 5.44 Hz, 1H), 6.86 (s, 1H), 4.21-4.45 (m, 2H), 4.02-4.09 (m, 4H), 3.82-3.84 (m, 1H), 2.98-3.04 (m, 1H), 2.80 (s, 1H), 2.56-2.57 (m, 1H), 1.81-2.05 (m, 4H), 1.74-1.81 (m, 4H), 1.41 (s, 9H), 1.15-1.26 (m, 2H);

LCMS: (method A) 600 (M+H), RT 3.41 min.

Synthesis of 2-(1-acetylpiperidin-4-ylmethoxy)-5-[2-(1-piperidin-4-yl-1H-pyrazol-4-ylamino)pyridin-4-yl]benzonitrile ("A116")

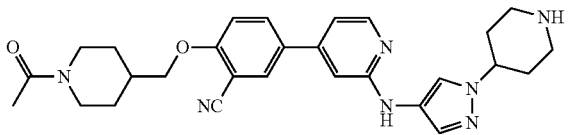 [SMILES: CC(=O)N1CCC(COc2ccc(-c3ccnc(Nc4cnn(C5CCNCC5)c4)c3)cc2C#N)CC1]

The preparation is carried out as described in the case of 2-cyclopropylmethoxy-5-[2-(1-piperidin-4-yl-1H-pyrazol-3-ylamino)pyridin-4-yl]benzonitrile ("A107"); yield: 18% (17.3 mg, brown solid);

$^1$H NMR (400 MHz, DMSO-d$_6$): δ [ppm] 8.81 (s, 1H), 8.14 (d, J=5.40 Hz, 1H), 8.05 (d, J=2.32 Hz, 1H), 7.98 (s, 1H), 7.94 (dd, J=2.32, 8.90 Hz, 1H), 7.45 (s, 1H), 7.38 (d, J=8.96 Hz, 1H), 6.93 (dd, J=1.32, 5.42 Hz, 1H), 6.85 (s, 1H), 4.39-4.43 (m, 1H), 4.04-4.15 (m, 3H), 3.84-3.88 (m, 1H), 3.00-3.09 (m, 3H), 2.54-2.60 (m, 3H), 2.05-2.08 (m, 1H), 1.99 (s, 3H), 1.72-1.92 (m, 6H), 1.12-1.30 (m, 2H);

LCMS: (method A) 500.2 (M+H), RT 2.55 min;
HPLC: (method A) RT. 2.44 min.

Synthesis of 2-(1-acetylpiperidin-4-ylmethoxy)-5-[2-(5-morpholin-4-ylpyridin-2-ylamino)pyridin-4-yl]benzonitrile ("A117")

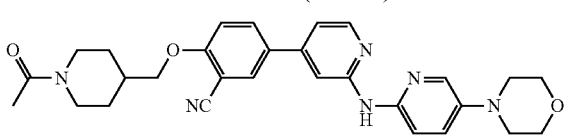

The preparation is carried out analogously to 2-cyclopropylmethoxy-5-[2-(5-morpholin-4-ylpyridin-2-ylamino)pyridin-4-yl]benzonitrile ("A113"); yield: 3.5% (4.6 mg, yellow solid);

$^1$H NMR (400 MHz, DMSO-d$_6$): δ [ppm] 9.44 (s, 1H), 8.21 (d, J=5.28 Hz, 1H), 8.06 (d, J=2.36 Hz, 1H), 7.93-7.98 (m, 2H), 7.82 (s, 1H), 7.73 (d, J=9.08 Hz, 1H), 7.41 (dd, J=3.16, 9.06 Hz, 2H), 7.12 (dd, J=1.64, 5.38 Hz, 1H), 4.40-4.43 (m, 1H), 4.05-4.13 (m, 2H), 3.85-3.88 (m, 2H), 3.74 (t, J=4.88 Hz, 4H), 3.04-3.09 (m, 4H), 2.55-2.61 (m, 1H), 2.03-2.11 (m, 1H), 1.99 (s, 3H), 1.77-1.85 (m, 2H), 1.11-1.35 (m, 2H);

LCMS: (method A) 513 (M+H), RT 3.31 min;
HPLC: (method A) RT. 3.46 min.

IC$_{50}$ values of TBK1- and IKKε-inhibiting compounds according to the invention

| Compound No. | TBK1 enzyme assay IC$_{50}$ [nM] | IKKε enzyme assay IC$_{50}$ [nM] | TBK1 + IKKε cell assay IC$_{50}$ [nM] |
|---|---|---|---|
| "A1" | | | |
| "A2" | 83 | 20 | 960 |
| "A3" | 260 | 370 | 3300 |
| "A4" | 34 | 38 | 6600 |
| "A5" | 97 | 110 | 2900 |
| "A6" | | | |
| "A7" | 8 | 15 | 350 |
| "A8" | | | |
| "A9" | 120 | 100 | 3000 |
| "A10" | 21 | 43 | 1200 |
| "A11" | 250 | 240 | 5200 |
| "A12" | 30 | 25 | 1300 |
| "A13" | 310 | 530 | |
| "A14" | 670 | 1200 | |
| "A15" | 14 | 21 | 1100 |
| "A16" | 71 | 7 | 5000 |
| "A17" | | | |
| "A18" | 8 | 13 | |
| "A19" | 1900 | 390 | |
| "A20" | 55 | 51 | 4800 |
| "A21" | 70 | 37 | 5300 |
| "A22" | 100 | 150 | 9600 |
| "A23" | 120 | 160 | 7800 |
| "A24" | 110 | 89 | 4800 |
| "A25" | 290 | 67 | |
| "A26" | 18 | 27 | 3300 |
| "A27" | 85 | 77 | 5000 |
| "A28" | 280 | 74 | 23000 |
| "A29" | 120 | 88 | 6700 |
| "A30" | 42 | 45 | |
| "A31" | 860 | 850 | 19000 |
| "A32" | | | |
| "A33" | 130 | 58 | 5000 |
| "A34" | 6 | 6 | 370 |
| "A35" | 6 | 18 | 670 |
| "A36" | | 140 | |
| "A37" | 32 | 21 | |
| "A38" | 460 | 320 | |
| "A39" | 16 | 25 | |
| "A40" | 7 | 5 | |
| "A41" | 12 | 25 | |
| "A42" | 10 | 15 | |
| "A43" | 70 | 65 | |
| "A44" | 5 | 10 | |
| "A45" | 2 | 2 | |
| "A64" | 6 | 6 | 230 |

-continued

| Compound No. | TBK1 enzyme assay IC$_{50}$ [nM] | IKKε enzyme assay IC$_{50}$ [nM] | TBK1 + IKKε cell assay IC$_{50}$ [nM] |
|---|---|---|---|
| "A65" | 170 | 120 | |
| "A66" | 100 | 82 | 4900 |
| "A67" | 6 | 4 | 420 |
| "A68" | 160 | 200 | |
| "A69" | 1600 | 650 | |
| "A70" | 180 | 140 | |
| "A71" | 21 | 6 | 2400 |
| "A72" | 10 | 7 | 840 |
| "A73" | 8 | 10 | 270 |
| "A74" | 2 | 1 | 1600 |
| "A75" | 3 | 4 | 500 |
| "A76" | 27 | 21 | 6100 |
| "A77" | 30 | 12 | 1400 |
| "A78" | 5 | 6 | 2100 |
| "A79" | 120 | 91 | 4900 |
| "A80" | 230 | 210 | 13000 |
| "A81" | 14 | 10 | 350 |
| "A82" | 230 | 150 | |
| "A83" | 60 | 88 | 5300 |
| "A84" | 350 | 210 | |
| "A85" | 330 | 390 | |
| "A86" | 290 | 300 | |
| "A87" | 300 | 300 | |
| "A88" | 41 | 45 | |
| "A89" | 140 | 120 | |
| "A90" | 88 | 98 | 1300 |
| "A91" | 32 | 8 | 2300 |
| "A92" | 850 | 930 | |
| "A93" | 550 | 310 | |
| "A94" | 14 | 18 | 980 |
| "A95" | 10 | 8 | 810 |
| "A96" | 24 | 40 | 5400 |
| "A97" | 11 | 39 | 2100 |
| "A98" | 5 | 8 | 390 |
| "A99" | 6 | 8 | 320 |
| "A100" | 14 | 39 | |
| "A101" | 3 | 5 | 440 |
| "A102" | 350 | 430 | |
| "A103" | 7 | 8 | 890 |
| "A104" | 460 | 96 | |
| "A105" | 220 | 65 | |
| "A106" | 41 | 46 | 4100 |
| "A107" | 50 | 30 | 11000 |
| "A108" | 23 | 45 | 1200 |
| "A109" | 380 | 140 | |
| "A110" | 490 | 82 | |
| "A111" | 89 | 200 | |
| "A112" | 65 | 30 | 7800 |
| "A113" | 54 | 120 | 2900 |
| "A114" | 5500 | 650 | |
| "A115" | 1500 | 1100 | |
| "A116" | 6600 | 190 | |
| "A117" | 810 | 610 | |
| "A118" | 24 | 25 | 450 |

The following examples relate to medicaments:

Example A

Injection Vials

A solution of 100 g of an active compound according to the invention and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

Example B

Suppositories

A mixture of 20 g of an active compound according to the invention with 100 g of soya lecithin and 1400 g of cocoa butter is melted, poured into moulds and allowed to cool. Each suppository contains 20 mg of active compound.

Example C

Solution

A solution is prepared from 1 g of an active compound according to the invention, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active compound according to the invention are mixed with 99.5 g of Vaseline under aseptic conditions.

Example E

Tablets

A mixture of 1 kg of active compound, 4 kg of lactose, 1.2 kg of potato starch, 0.2 kg of talc and 0.1 kg of magnesium stearate is pressed in a conventional manner to give tablets in such a way that each tablet contains 10 mg of active compound.

Example F

Dragees

Tablets are pressed analogously to Example E and subsequently coated in a conventional manner with a coating of sucrose, potato starch, talc, tragacanth and dye.

Example G

Capsules 2 kg of active compound are introduced into hard gelatine capsules in a conventional manner in such a way that each capsule contains 20 mg of the active compound.

Example H

Ampoules

A solution of 1 kg of an active compound according to the invention in 60 l of bidistilled water is sterile-filtered, transferred into ampoules, lyophilised under sterile conditions and sealed under sterile conditions. Each ampoule contains 10 mg of active compound.

The invention claimed is:

1. A compound selected from the following group of compounds:

| Compound No. | Name and/or structure |
|---|---|
| "A1" | 2-(Tetrahydropyran-4-yloxy)-5-{2-[1-(3-trifluoromethylphenyl)-1H-pyrazol-4-ylamino]pyridin-4-yl}benzonitrile |
| "A2" | 5-{2-[1-(1-Methylpiperidin-4-yl)-1H-pyrazol-4-ylamino]pyridin-4-yl}-2-(tetrahydropyran-4-yloxy)benzonitrile |
| "A3" | 5-[2-([3,3']Bipyridinyl-6-ylamino)pyridin-4-yl]-2-(tetrahydropyran-4-yloxy)benzonitrile |
| "A4" | 5-[2-(5-Methylisoxazol-3-ylamino)pyridin-4-yl]-2-(tetrahydropyran-4-yloxy)benzonitrile |
| "A5" | 5-[2-(1-Methyl-1H-pyrazol-3-ylamino)pyridin-4-yl]-2-(tetrahydropyran-4-yloxy)benzonitrile |
| "A6" | 5-[2-(2-Furan-2-ylmethyl-2H-pyrazol-3-ylamino)pyridin-4-yl]-2-(tetrahydropyran-4-yloxy)benzonitrile |
| "A7" | 5-[2-(5-Morpholin-4-ylpyridin-2-ylamino)pyridin-4-yl]-2-(tetrahydropyran-4-yloxy)benzonitrile |
| "A8" | 5-[2-(1-Phenyl-1H-pyrazol-4-ylamino)pyridin-4-yl]-2-(tetrahydropyran-4-yloxy)benzonitrile |
| "A9" | 5-{2-[5-(1H-Pyrazol-4-yl)pyridin-2-ylamino]pyridin-4-yl}-2-(tetrahydropyran-4-yloxy)benzonitrile |
| "A10" | 5-[2-(5-tert-Butyl-1H-pyrazol-3-ylamino)pyridin-4-yl]-2-(tetrahydropyran-4-yloxy)benzonitrile |
| "A11" | 6-{4-[3-Cyano-4-(tetrahydropyran-4-yloxy)phenyl]pyridin-2-ylamino}nicotinonitrile |
| "A12" | 5-[2-(5-Cyclopropyl-2H-pyrazol-3-ylamino)pyridin-4-yl]-2-(tetrahydropyran-4-yloxy)benzonitrile |
| "A13" | 2-(Tetrahydropyran-4-yloxy)-5-[2-(5-trifluoromethylpyridin-2-ylamino)pyridin-4-yl]benzonitrile |
| "A14" | 5-[2-(Pyrimidin-2-ylamino)pyridin-4-yl]-2-(tetrahydropyran-4-yloxy)-benzonitrile |
| "A15" | 5-[2-(5-Hydroxymethylpyridin-2-ylamino)pyridin-4-yl]-2-(tetrahydropyran-4-yloxy)benzonitrile |
| "A16" | 5-[2-(1-Piperidin-4-yl-1H-pyrazol-4-ylamino)pyridin-4-yl]-2-(tetrahydropyran-4-yloxy)benzonitrile |
| "A17" | 2-{4-[3-Cyano-4-(tetrahydropyran-4-yloxy)phenyl]pyridin-2-ylamino}isonicotinonitrile |
| "A18" | 5-[2-(4-Hydroxymethylpyridin-2-ylamino)pyridin-4-yl]-2-(tetrahydropyran-4-yloxy)benzonitrile |
| "A19" | 5-{4-[3-Cyano-4-(tetrahydropyran-4-yloxy)phenyl]pyridin-2-ylamino}benzofuran-2-carboxamide |

| Compound No. | Name and/or structure |
|---|---|
| "A20" | 5-{2-[1-(2,2-Difluoroethyl)-1H-pyrazol-4-ylamino]pyridin-4-yl}-2-(tetrahydropyran-4-yloxy)benzonitrile |
| "A21" | 5-{2-[1-(2-Piperidin-4-ylethyl)-1H-pyrazol-4-ylamino]pyridin-4-yl}-2-(tetrahydropyran-4-yloxy)benzonitrile |
| "A22" | 5-{2-[1-(2-Morpholin-4-ylethyl)-1H-pyrazol-4-ylamino]pyridin-4-yl}-2-(tetrahydropyran-4-yloxy)benzonitrile |
| "A23" | 5-{2-[1-(3-Methoxypropyl)-1H-pyrazol-4-ylamino]pyridin-4-yl}-2-(tetrahydropyran-4-yloxy)benzonitrile |
| "A24" | 5-{2-[1-(2-Cyanocyclopropylmethyl)-1H-pyrazol-4-ylamino]pyridin-4-yl}-2-(tetrahydropyran-4-yloxy)benzonitrile |
| "A25" | 5-[2-(1-Azetidin-3-yl-1H-pyrazol-4-ylamino)pyridin-4-yl]-2-(tetrahydropyran-4-yloxy)benzonitrile |
| "A26" | 5-{2-[1-((1S,2S)-2-Hydroxymethyl-cyclopropylmethyl)-1H-pyrazol-4-ylamino]pyridin-4-yl}-2-(tetrahydropyran-4-yloxy)benzonitrile |
| "A27" | 5-{2-[1-(Tetrahydrofuran-3-ylmethyl)-1H-pyrazol-4-ylamino]pyridin-4-yl-2-(tetrahydropyran-4-yloxy)benzonitrile |
| "A28" | 5-[2-(1-Pyrrolidin-3-yl-1H-pyrazol-4-ylamino)pyridin-4-yl]-2-(tetrahydropyran-4-yloxy)benzonitrile |
| "A29" | 5-[2-(1-{2-[1-(2-Hydroxyacetyl)piperidin-4-yl]ethyl}-1H-pyrazol-4-ylamino)pyridin-4-yl]-2-(tetrahydropyran-4-yloxy)benzonitrile |
| "A30" | 5-[2-(1-{2-[1-(2-Aminoacetyl)piperidin-4-yl]ethyl}-1H-pyrazol-4-ylamino)pyridin-4-yl]-2-(tetrahydropyran-4-yloxy)benzonitrile |
| "A31" | 5-[2-(3-tert-Butylisoxazol-5-ylamino)pyridin-4-yl]-2-(tetrahydropyran-4-yloxy)benzonitrile |
| "A32" | 2-(Tetrahydropyran-4-yloxy)-5-{2-[1-(3-trifluoromethylphenyl)-1H-pyrazol-4-ylamino]pyrimidin-4-yl}benzonitrile |
| "A33" | 5-[2-(1-Methyl-1H-pyrazol-3-ylamino)pyrimidin-4-yl]-2-(tetrahydropyran-4-yloxy)benzonitrile |
| "A34" | 5-[2-(1H-Pyrazol-4-ylamino)pyrimidin-4-yl]-2-(tetrahydropyran-4-yloxy)benzonitrile |
| "A35" | 5-{2-[1-(2-Methoxyethyl)-1H-pyrazol-4-ylamino]pyrimidin-4-yl}-2-(tetrahydropyran-4-yloxy)benzonitrile |
| "A36" | 2-(Tetrahydropyran-4-yloxy)-5-[2-(5,6,7,8-tetrahydropyrido[4,3-d]pyrimidin-2-ylamino)pyridin-4-yl]benzonitrile |
| "A37" | 6-{4-[3-Cyano-4-(tetrahydropyran-4-yloxy)phenyl]pyridin-2-yl-amino}nicotinamide |
| "A38" | 5-{2-[1-(2-Pyrazol-1-ylethyl)-1H-pyrazol-4-ylamino]pyridin-4-yl}-2-(tetrahydropyran-4-yloxy)benzonitrile |
| "A39" | 5-{2-[1-(2-Morpholin-4-ylethyl)-1H-pyrazol-4-ylamino]pyrimidin-4-yl}-2-(tetrahydropyran-4-yloxy)benzonitrile |
| "A40" | 5-[2-(1-Pyrrolidin-3-yl-1H-pyrazol-4-ylamino)pyrimidin-4-yl]-2-(tetrahydropyran-4-yloxy)benzonitrile |
| "A41" | 5-{2-[1-(Tetrahydrofuran-3-ylmethyl)-1H-pyrazol-4-ylamino]-pyrimidin-4-yl}-2-(tetrahydropyran-4-yloxy)benzonitrile |
| "A42" | 5-{4-[3-Cyano-4-(tetrahydropyran-4-yloxy)phenyl]pyrimidin-2-ylamino}benzofuran-2-carboxamide |
| "A43" | 5-{2-[1-(2-Pyrazol-1-ylethyl)-1H-pyrazol-4-ylamino]pyrimidin-4-yl}-2-(tetrahydropyran-4-yloxy)benzonitrile |
| "A44" | 5-{2-[1-(2,2-Difluoroethyl)-1H-pyrazol-4-ylamino]pyrimidin-4-yl}-2-(tetrahydropyran-4-yloxy)benzonitrile |
| "A45" | 5-{2-[1-(2-Piperidin-4-ylethyl)-1H-pyrazol-4-ylamino]pyrimidin-4-yl}-2-(tetrahydropyran-4-yloxy)benzonitrile |
| "A46" | 5-{2-[1-(3-Methoxypropyl)-1H-pyrazol-4-ylamino]pyrimidin-4-yl}-2-(tetrahydropyran-4-yloxy)benzonitrile |
| "A47" | 5-{2-[5-(3,6-Dihydro-2H-pyran-4-yl)pyridin-2-ylamino]pyridin-4-yl}-2-(tetrahydropyran-4-yloxy)benzonitrile |
| "A48" | 5-[2-(1',2',3',6'-Tetrahydro-[3,4']bipyridinyl-6-ylamino)pyridin-4-yl]-2-(tetrahydropyran-4-yloxy)benzonitrile |
| "A53" | |
| "A58" | |
| "A59" | |

| Compound No. | Name and/or structure |
|---|---|
| "A60" | (structure) |
| "A61" | (structure) |
| "A62" | (structure) |
| "A63" | (structure) |
| "A64" | 5-[2-(1-Piperidin-4-yl-1H-pyrazol-4-ylamino)pyrimidin-4-yl]-2-(tetrahydropyran-4-yloxy)benzonitrile |
| "A65" | 2-{4-[3-Cyano-4-(tetrahydropyran-4-yloxy)phenyl]pyridin-2-ylamino}isonicotinic acid |
| "A66" | 5-[2-(5-Piperidin-4-ylpyrimidin-2-ylamino)pyridin-4-yl]-2-(tetrahydropyran-4-yloxy)benzonitrile |
| "A67" | 5-{2-[1-((1S,2S)-2-Hydroxymethyl-cyclopropylmethyl)-1H-pyrazol-4-ylamino]pyrimidin-4-yl}-2-(tetrahydropyran-4-yloxy)benzonitrile |
| "A68" | 5-[2-(1-Methyl-6-oxo-1,6-dihydropyridazin-3-ylamino)pyrimidin-4-yl]-2-(tetrahydropyran-4-yloxy)benzonitrile |
| "A69" | 5-[2-(6-Oxo-1,6-dihydropyridazin-3-ylamino)pyrimidin-4-yl]-2-(tetrahydropyran-4-yloxy)benzonitrile |
| "A70" | 5-[2-(4-Hydroxymethylpyridin-2-ylamino)pyrimidin-4-yl]-2-(tetrahydropyran-4-yloxy)benzonitrile |
| "A71" | 5-[2-(6-Piperidin-4-ylpyridazin-3-ylamino)pyrimidin-4-yl]-2-(tetrahydropyran-4-yloxy)benzonitrile |
| "A72" | 5-[2-(5-Piperidin-4-ylpyrazin-2-ylamino)pyrimidin-4-yl]-2-(tetrahydropyran-4-yloxy)benzonitrile |
| "A73" | 5-{2-[1-(4-Hydroxycyclohexyl)-1H-pyrazol-4-ylamino]pyrimidin-4-yl}-2-(tetrahydropyran-4-yloxy)benzonitrile |
| "A74" | 5-[2-(1',2',3',4',5',6'-Hexahydro-[4,4']bipyridinyl-2-ylamino)pyridin-4-yl]-2-(tetrahydropyran-4-yloxy)benzonitrile |
| "A75" | 5-{2-[1-(2-Hydroxyethyl)-1H-pyrazol-4-ylamino]pyrimidin-4-yl}-2-(tetrahydropyran-4-yloxy)benzonitrile |
| "A76" | 5-[2-(2-Methoxy-1',2',3',6'-tetrahydro-[3,4']bipyridinyl-6-ylamino)-pyrimidin-4-yl]-2-(tetrahydropyran-4-yloxy)benzonitrile |
| "A77" | 5-[2-(4-Aminomethylpyridin-2-ylamino)pyridin-4-yl]-2-(tetrahydropyran-4-yloxy)benzonitrile |
| "A78" | 5-[2-(1'-Methyl-1',2',3',4',5',6'-hexahydro-[4,4']bipyridinyl-2-ylamino)-pyridin-4-yl]-2-(tetrahydropyran-4-yloxy)benzonitrile |
| "A79" | 5-{2-[1-(2-Hydroxyethyl)-1H-pyrazol-4-ylamino]pyridin-4-yl}-2-(tetrahydropyran-4-yloxy)benzonitrile |
| "A80" | 5-[2-(5-Methylisoxazol-3-ylamino)pyrimidin-4-yl]-2-(tetrahydropyran-4-yloxy)benzonitrile |
| "A81" | 5-[2-(4-Dimethylaminomethylpyridin-2-ylamino)pyridin-2-yl]-2-(tetrahydropyran-4-yloxy)benzonitrile |
| "A82" | 5-[2-(4-Morpholin-4-ylpyridin-2-ylamino)pyridin-4-yl]-2-(tetrahydropyran-4-yloxy)benzonitrile |
| "A83" | 5-{2-[1-(2-Pyrrolidin-1-ylethyl)-1H-pyrazol-4-ylamino]pyrimidin-4-yl}-2-(tetrahydropyran-4-yloxy)benzonitrile |
| "A84" | 5-{2-[4-(4-Methylpiperazin-1-yl)pyridin-2-ylamino]pyridin-4-yl}-2-(tetrahydropyran-4-yloxy)benzonitrile |
| "A85" | 5-[2-(6-Morpholin-4-ylpyrazin-2-ylamino)pyridin-4-yl]-2-(tetrahydropyran-4-yloxy)benzonitrile |
| "A86" | 5-{2-[4-(5,6-Dihydro-4H-pyran-2-yl)pyridin-2-ylamino]pyridin-4-yl}-2-(tetrahydropyran-4-yloxy)benzonitrile |
| "A87" | 5-[2-(4-Cyclopropylthiazol-2-ylamino)pyrimidin-4-yl]-2-(tetrahydropyran-4-yloxy)benzonitrile |
| "A88" | 5-{2-[5-(2-Oxa-6-azaspiro[3.3]hept-6-ylmethyl)pyridin-2-ylamino]-pyridin-4-yl}-2-(tetrahydropyran-4-yloxy)benzonitrile |
| "A89" | 5-[2-(4-Piperidin-4-ylpyrimidin-2-ylamino)pyridin-4-yl]-2-(tetrahydropyran-4-yloxy)benzonitrile |
| "A90" | 5-[2-(6-Morpholin-4-ylpyridazin-3-ylamino)pyridin-4-yl]-2-(tetrahydropyran-4-yloxy)benzonitrile |
| "A91" | 5-[2-(1',2',3',4',5',6'-Hexahydro-[2,4']bipyridinyl-6-ylamino)pyridin-4-yl]-2-(tetrahydropyran-4-yloxy)benzonitrile |

| Compound No. | Name and/or structure |
|---|---|
| "A92" | 5-{2-[6-(5,6-Dihydro-4H-pyran-2-yl)pyrazin-2-ylamino]pyridin-4-yl}-2-(tetrahydropyran-4-yloxy)benzonitrile |
| "A93" | 5-[2-(4-Methyloxazol-2-ylamino)pyrimidin-4-yl]-2-(tetrahydropyran-4-yloxy)benzonitrile |
| "A94" | 2-Cyclobutylmethoxy-5-{2-[1-(2-hydroxyethyl)-1H-pyrazol-4-yl-amino]pyrimidin-4-yl}benzonitrile |
| "A95" | 2-Cyclobutylmethoxy-5-{2-[1-((1S,2S)-2-hydroxymethylcyclopropyl-methyl)-1H-pyrazol-4-ylaminol]pyrimidin-4-yl}benzonitrile |
| "A96" | 5-[2-(6-Piperidin-4-ylpyrazin-2-ylamino)pyridin-4-yl]-2-(tetrahydropyran-4-yloxy)benzonitrile |
| "A97" | 2-Cyclobutylmethoxy-5-{2-[1-(4-hydroxycyclohexyl)-1H-pyrazol-4-ylamino]pyrimidin-4-yl}benzonitrile |
| "A98" | 2-(Tetrahydropyran-4-yloxy)-5-{2-[5-(tetrahydropyran-4-yl)pyrazin-2-ylamino]pyridin-4-yl}benzonitrile |
| "A99" | 5-[2-(5-Hydroxymethylpyrazin-2-ylamino)pyridin-4-yl]-2-(tetrahydropyran-4-yloxy)benzonitrile |
| "A100" | 2-(Tetrahydropyran-4-yloxy)-5-{2-[6-(tetrahydropyran-4-yl)pyridazin-3-ylamino]pyridin-4-yl}benzonitrile |
| "A101" | 5-{2-[1-(4-Hydroxycyclohexyl)-1H-pyrazol-4-ylamino]pyrimidin-4-yl}-2-(tetrahydropyran-4-yloxy)benzonitrile |
| "A102" | 5-[2-(3-Hydroxymethylpyrazin-2-ylamino)pyridin-4-yl]-2-(tetrahydropyran-4-yloxy)benzonitrile |
| "A103" | 2-Cyclobutylmethoxy-5-{2-[1-(2-methoxyethyl)-1H-pyrazol-4-yl-amino]pyrimidin-4-yl}benzonitrile |
| "A104" | 2-Cyclopropylmethoxy-5-[2-(1H-pyrazol-4-ylamino)pyridin-4-yl]-benzonitrile |
| "A105" | 2-Cyclopropylmethoxy-5-{2-[1-(2-methoxyethyl)-1H-pyrazol-4-ylamino]pyridin-4-yl}benzonitrile |
| "A106" | 2-Cyclopropylmethoxy-5-[2-(5-hydroxymethylpyridin-2-ylamino)-pyridin-4-yl]benzonitrile |
| "A107" | 2-Cyclopropylmethoxy-5-[2-(1-piperidin-4-yl-1H-pyrazol-3-ylamino)-pyridin-4-yl]benzonitrile |
| "A108" | 2-Cyclopropylmethoxy-5-[2-(5-morpholin-4-ylpyridin-2-ylamino)-pyridin-4-yl]benzonitrile |
| "A109" | 2-Cyclobutylmethoxy-5-[2-(1H-pyrazol-4-ylamino)pyridin-4-yl]-benzonitrile |
| "A110" | 2-Cyclobutylmethoxy-5-{2-[1-(2-methoxyethyl)-1H-pyrazol-4-ylamino]pyridin-4-yl}benzonitrile |
| "A111" | 2-Cyclobutylmethoxy-5-[2-(5-hydroxymethylpyridin-2-ylamino)-pyridin-4-yl]benzonitrile |
| "A112" | 2-Cyclobutylmethoxy-5-[2-(1-piperidin-4-yl-1H-pyrazol-4-ylamino)-pyridin-4-yl]benzonitrile |
| "A113" | 2-Cyclobutylmethoxy-5-[2-(5-morpholin-4-ylpyridin-2-ylamino)-pyridin-4-yl]benzonitrile |
| "A114" | 2-(1-Acetylpiperidin-4-ylmethoxy)-5-{2-[1-(2-methoxyethyl)-1H-pyrazol-4-ylamino]pyridin-4-yl}benzonitrile |
| "A115" | 2-(1-Acetylpiperidin-4-ylmethoxy)-5-[2-(5-hydroxymethylpyridin-2-ylamino)pyridin-4-yl]benzonitrile |
| "A116" | 2-(1-Acetylpiperidin-4-ylmethoxy)-5-[2-(1-piperidin-4-yl-1H-pyrazol-4-ylamino)pyridin-4-yl]benzonitrile |
| "A117" | 2-(1-Acetylpiperidin-4-ylmethoxy)-5-[2-(5-morpholin-4-ylpyridin-2-ylamino)pyridin-4-yl]benzonitrile |
| "A118" | 5-[2-(5-Morpholin-4-ylmethylpyridin-2-ylamino)pyridin-4-yl]-2-(tetrahydropyran-4-yloxy)benzonitrile | and pharmaceutically usable salts, tautomers and stereoisomers thereof, including mixtures thereof in all ratios.

\* \* \* \* \*

SEQUENCE LISTING

<160> NUMBER OF SEQ ID NOS: 2

<210> SEQ ID NO 1
<211> LENGTH: 23
<212> TYPE: PRT
<213> ORGANISM: Artificial Sequence
<220> FEATURE:
<223> OTHER INFORMATION: Biotin-C6-C6
<220> FEATURE:
<221> NAME/KEY: MISC_FEATURE
<222> LOCATION: (1)..(1)

<400> SEQUENCE: 1

Gly Leu Lys Lys Glu Arg Leu Leu Asp Asp Arg His Asp Ser Gly Leu
1               5                   10                  15

Asp Ser Met Lys Asp Glu Glu
            20

<210> SEQ ID NO 2
<211> LENGTH: 23
<212> TYPE: PRT
<213> ORGANISM: Artificial Sequence
<220> FEATURE:
<223> OTHER INFORMATION: Biotin-Ah-Ah
<220> FEATURE:
<221> NAME/KEY: MISC_FEATURE
<222> LOCATION: (1)..(1)

<400> SEQUENCE: 2

Ala Lys Pro Lys Gly Asn Lys Asp Tyr His Leu Gln Thr Cys Cys Gly
1               5                   10                  15

Ser Leu Ala Tyr Arg Arg Arg
            20